(12) United States Patent
Gillespie et al.

(10) Patent No.: US 6,936,457 B1
(45) Date of Patent: *Aug. 30, 2005

(54) DNA ENCODING HUMAN α AND β SUBUNITS OF NEURONAL NICOTINIC ACETYLCHOLINE RECEPTOR, CELLS TRANSFORMED THEREWITH, AND RECOMBINANT CELL LINE EXPRESSING A HUMAN α AND β SUBUNIT OF NEURONAL NICOTINIC ACETYLCHOLINE RECEPTOR

(75) Inventors: Allison Gillespie, San Diego, CA (US); Brian O. Claeps, San Diego, CA (US); Laura Elena Chavez-Noriega, San Diego, CA (US); Robert Siegel, San Diego, CA (US); Kathryn J. Elliott, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 426 days.

This patent is subject to a terminal disclaimer.

(21) Appl. No.: 09/703,951

(22) Filed: Nov. 1, 2000

Related U.S. Application Data

(63) Continuation-in-part of application No. 08/487,596, filed on Jun. 7, 1995, now Pat. No. 6,440,681, which is a continuation-in-part of application No. 08/149,503, filed on Nov. 8, 1993, now abandoned, and a continuation-in-part of application No. 08/028,031, filed on Mar. 8, 1993, now abandoned, and a continuation-in-part of application No. 07/938,154, filed on Nov. 30, 1992, now Pat. No. 5,981,193, which is a continuation-in-part of application No. 07/504,455, filed on Apr. 3, 1990, now Pat. No. 5,369,028.

(51) Int. Cl.$^7$ .............................................. C12N 1/20
(52) U.S. Cl. ................ 435/252.3; 435/69.1; 435/320.1; 435/352; 530/350; 536/23.5
(58) Field of Search ........................... 435/6, 7.1, 7.21, 435/69.1, 252.3, 320.1, 352; 436/501; 530/350; 514/2; 536/23.1, 23.5

(56) References Cited

U.S. PATENT DOCUMENTS

| 5,371,188 A | 12/1994 | Heinemann et al. ........ 530/350 |
| 5,837,489 A | * 11/1998 | Elliott et al. ................ 435/69.1 |

OTHER PUBLICATIONS

Peng–X et al., Molecular Pharmacology 45(546–554)1994.*
Quik–M et al. Journal of Neurochemistry 67(145–154)1996.*
Sambrook–J. ed. Molecular Cloning, Cold Spring Harbor Laboratory Press, 1989, pp. 16.3–16.21.*
Lukas, R. J., et al., International Union of Pharmacology. XX. . . . Receptors and Their Subunits, Pharmacological Reviews, 1999, vol. 51, No. 2, p. 397–401.
Porter, J. T., et al., Selective Excitation of Subtypes of Neocortical Interneurons by Nicontinic Receptors, The Journal of Neuroscience, Jul. 1, 1999, 19(13) p. 5228–5235.
Quick, M. et al., Modulation of α 7 Nicotinic Receptor–Mediated Calcium Influx by Nicotinic Agonists, Molecular Pharmacology, 51:499–407 (1997).
Ramirez–Latorre, J. et al., Functional Contributions of α5 Subunit to Neuronal Acetylcholine Receptor Channels, NATURE, vol. 380, Mar. 28, 1996, p. 347–351.
Whiting, P.J. and Lindstrom, J.M., "Characterization of Bovine and Human Neuronal Nicotinic Acetylcholine Receptors Using Monoclonal Antibodies", *J. Neurosci.,* 8(9):3395–3404, (1988).
Grenningloh et al., Alpha subunit variants of the human glycine receptor: primary structures, functional expression and chromosomal localization of the corresponding genes, *EMBO J.* 9(3): 771–776 (1990).
Lamar et al., Amplification of genomic sequences identifies a new gene, alpha 6, in the niocotinic acetylcholine receptor gene family, *Abstracts 20th Annual Meeting For Society For Neuroscience* 16: 681 #285.2 (1990).
Lin et al., Differential fluorescent staining of human chromosomes with daunomycin and adriamycin—the D–bands *Science 190:* 61–63 (1975).
EMBL Databank, Accession No. X68275 (Sep. 22, 1992), P. Tarroni.
PIR 38 Databank, Accession No. S27274 (Tarroni et al.).
GeneSeq 12 Databank, Accession No. 006086 (WO 90/10648).
George et al., Chapter 12: Current methods in Sequence Comparison and Analysis in *Macromolecular Sequencing and Synthesis, Selected Methods and Applications,* Alan R. Liss, Inc., pp. 127–149 (1988).
Koyama et al., Isolation of 115 human chromosome 8–specific expressed–sequence tags by exon amplification, *Genomics* 26:245–253 (1995).

* cited by examiner

*Primary Examiner*—Elizabeth Kemmerer
*Assistant Examiner*—Michael Brannock
(74) *Attorney, Agent, or Firm*—Vineet Kohli; Joanne M. Giesser

(57) ABSTRACT

Isolated nucleic acid molecules, i.e., DNA or RNA encoding human neuronal nicotinic acetylcholine receptor alpha and beta subunits, mammalian and amphibian cells containing said DNA, methods for producing α and β subunits and recombinant (i.e., isolated or substantially pure) α subunits and β subunits are provided. In addition, cells expressing various multimeric combinations of subunits (i.e., $\alpha_1$, $\alpha_2$, $\alpha_3$, $\alpha_4$, $\alpha_5$, $\alpha_6$ and/or $\alpha_7$ in combination with at least one of an α and β subunit are also provided. A recombinant, non-human cell line expressing the human $\alpha_7$ subunit of nAChR is disclosed.

8 Claims, 16 Drawing Sheets

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 2277 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 166..1755
      (D) OTHER INFORMATION: /product= "ALPHA-2 SUBUNIT"

(xi) SEQUENCE DESCRIPTION: SEQ ID NO: 1:

```
CAATGACCTG TTTTCTTCTG TAACCACAGG TTCGGTGGTG AGAGGAASCY TCGCAGAATC      60

CAGCAGAATC CTCACAGAAT CCAGCAGCAG CTCTGCTGGG GACATGGTCC ATGGTGCAAC     120

CCACAGCAAA GCCCTGACCT GACCTCCTGA TGCTCAGGAG AAGCCATGGG CCCCTCCTGT     180

CCTGTGTTCC TGTCCTTCAC AAAGCTCAGC CTGTGGTGGC TCCTTCTGAC CCCAGCAGGT     240

GGAGAGGAAG CTAAGCGCCC ACCTCCCAGG GCTCCTGGAG ACCCACTCTC CTCTCCCAGT     300

CCCACGGCAT TGCCGCAGGG AGGCTCGCAT ACCGAGACTG AGGACCGGCT CTTCAAACAC     360

CTCTTCCGGG GCTACAACCG CTGGGCGCGC CCGGTGCCCA ACACTTCAGA CGTGGTGATT     420

GTGCGCTTTG GACTGTCCAT CGCTCAGCTC ATCGATGTGG ATGAGAAGAA CCAAATGATG     480

ACCACCAACG TCTGGCTAAA ACAGGAGTGG AGCGACTACA AACTGCGCTG GAACCCCGCT     540

GATTTTGGCA ACATCACATC TCTCAGGGTC CCTTCTGAGA TGATCTGGAT CCCCGACATT     600

GTTCTCTACA ACAATGCAGA TGGGGAGTTT GCAGTGACCC ACATGACCAA GGCCCACCTC     660

TTCTCCACGG GCACTGTGCA CTGGGTGCCC CCGGCCATCT ACAAGAGCTC CTGCAGCATC     720

GACGTCACCT TCTTCCCCTT CGACCAGCAG AACTGCAAGA TGAAGTTTGG CTCCTGGACT     780

TATGACAAGG CCAAGATCGA CCTGGAGCAG ATGGAGCAGA CTGTGGACCT GAAGGACTAC     840

TGGGAGAGCG GCGAGTGGGC CATCGTCAAT GCCACGGGCA CCTACAACAG CAAGAAGTAC     900

GACTGCTGCG CCGAGATCTA CCCCGACGTC ACCTACGCCT TCGTCATCCG GCGGCTGCCG     960

CTCTTCTACA CCATCAACCT CATCATCCCC TGCCTGCTCA TCTCCTGCCT CACTGTGCTG    1020

GTCTTCTACC TGCCCTCCGA CTGCGGCGAG AAGATCACGC TGTGCATTTC GGTGCTGCTG    1080

TCACTCACCG TCTTCCTGCT GCTCATCACT GAGATCATCC CGTCCACCTC GCTGGTCATC    1140

CCGCTCATCG GCGAGTACCT GCTGTTCACC ATGATCTTCG TCACCCTGTC CATCGTCATC    1200

ACCGTCTTCG TGCTCAATGT GCACCACCGC TCCCCCAGCA CCCACACCAT GCCCCACTGG    1260

GTGCGGGGGG CCCTTCTGGG CTGTGTGCCC CGGTGGCTTC TGATGAACCG GCCCCCACCA    1320

CCCGTGGAGC TCTGCCACCC CCTACGCCTG AAGCTCAGCC CCTCTTATCA CTGGCTGGAG    1380

AGCAACGTGG ATGCCGAGGA GAGGGAGGTG GTGGTGGAGG AGGAGGACAG ATGGGCATGT    1440

GCAGGTCATG TGGCCCCCTC TGTGGGCACC CTCTGCAGCC ACGGCCACCT GCACTCTGGG    1500

GCCTCAGGTC CCAAGGCTGA GGCTCTGCTG CAGGAGGGTG AGCTGCTGCT ATCACCCCAC    1560

ATGCAGAAGG CACTGGAAGG TGTGCACTAC ATTGCCGACC ACCTGCGGTC TGAGGATGCT    1620
```

-continued

```
GACTCTTCGG TGAAGGAGGA CTGGAAGTAT GTTGCCATGG TCATCGACAG GATCTTCCTC    1680

TGGCTGTTTA TCATCGTCTG CTTCCTGGGG ACCATCGGCC TCTTTCTGCC TCCGTTCCTA    1740

GCTGGAATGA TCTGACTGCA CCTCCCTCGA GCTGGCTCCC AGGGCAAAGG GGAGGGTTCT    1800

TGGATGTGGA AGGGCTTTGA ACAATGTTTA GATTTGGAGA TGAGCCCAAA GTGCCAGGGA    1860

GAACAGCCAG GTGAGGTGGG AGGTTGGAGA GCCAGGTGAG GTCTCTCTAA GTCAGGCTGG    1920

GGTTGAAGTT TGGAGTCTGT CCGAGTTTGC AGGGTGCTGA GCTGTATGGT CCAGCAGGGG    1980

AGTAATAAGG GCTCTTCCGG AAGGGGAGGA AGCGGGAGGC AGGGCCTGCA CCTGATGTGG    2040

AGGTACAGGG CAGATCTTCC CTACCGGGGA GGGATGGATG GTTGGATACA GGTGGCTGGG    2100

CTATTCCATC CATCTGGAAG CACATTTGAG CCTCCAGGCT TCTCCTTGAC GTCATTCCTC    2160

TCCTTCCTTG CTCCAAAATG GCTCTGCACC AGCCGGCCCC CAGGAGGTCT GGCAGAGCTG    2220

AGAGCCATGG CCTGCAGGGG CTCCATATGT CCCTACGCGT GCAGCAGGCA AACAAGA      2277
```

(2) INFORMATION FOR SEQ ID NO: 2:

(i) SEQUENCE CHARACTERISTICS:
        (A) LENGTH: 529 amino acids
        (B) TYPE: amino acid
        (D) TOPOLOGY: unknown (ii) MOLECULE TYPE: protein (xi) SEQUENCE DESCRIPTION: SEQ ID NO: 2:

```
Met Gly Pro Ser Cys Pro Val Phe Leu Ser Phe Thr Lys Leu Ser Leu
1               5                   10                  15

Trp Trp Leu Leu Leu Thr Pro Ala Gly Gly Glu Glu Ala Lys Arg Pro
                20                  25                  30

Pro Pro Arg Ala Pro Gly Asp Pro Leu Ser Ser Pro Ser Pro Thr Ala
            35                  40                  45

Leu Pro Gln Gly Gly Ser His Thr Glu Thr Glu Asp Arg Leu Phe Lys
        50                  55                  60

His Leu Phe Arg Gly Tyr Asn Arg Trp Ala Arg Pro Val Pro Asn Thr
65                  70                  75                  80

Ser Asp Val Val Ile Val Arg Phe Gly Leu Ser Ile Ala Gln Leu Ile
                85                  90                  95

Asp Val Asp Glu Lys Asn Gln Met Met Thr Thr Asn Val Trp Leu Lys
            100                 105                 110

Gln Glu Trp Ser Asp Tyr Lys Leu Arg Trp Asn Pro Ala Asp Phe Gly
        115                 120                 125

Asn Ile Thr Ser Leu Arg Val Pro Ser Glu Met Ile Trp Ile Pro Asp
    130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
            180                 185                 190

Asp Gln Gln Asn Cys Lys Met Lys Phe Gly Ser Trp Thr Tyr Asp Lys
        195                 200                 205

Ala Lys Ile Asp Leu Glu Gln Met Glu Gln Thr Val Asp Leu Lys Asp
    210                 215                 220

Tyr Trp Glu Ser Gly Glu Trp Ala Ile Val Asn Ala Thr Gly Thr Tyr
225                 230                 235                 240
```

-continued

```
Asn Ser Lys Lys Tyr Asp Cys Cys Ala Glu Ile Tyr Pro Asp Val Thr
            245                 250                 255

Tyr Ala Phe Val Ile Arg Arg Leu Pro Leu Phe Tyr Thr Ile Asn Leu
            260                 265                 270

Ile Ile Pro Cys Leu Leu Ile Ser Cys Leu Thr Val Leu Val Phe Tyr
            275                 280                 285

Leu Pro Ser Asp Cys Gly Glu Lys Ile Thr Leu Cys Ile Ser Val Leu
290                 295                 300

Leu Ser Leu Thr Val Phe Leu Leu Ile Thr Glu Ile Pro Ser
305                 310                 315             320

Thr Ser Leu Val Ile Pro Leu Ile Gly Glu Tyr Leu Leu Phe Thr Met
                325                 330                 335

Ile Phe Val Thr Leu Ser Ile Val Ile Thr Val Phe Val Leu Asn Val
                340                 345                 350

His His Arg Ser Pro Ser Thr His Thr Met Pro His Trp Val Arg Gly
                355                 360                 365

Ala Leu Leu Gly Cys Val Pro Arg Trp Leu Leu Met Asn Arg Pro Pro
            370                 375                 380

Pro Pro Val Glu Leu Cys His Pro Leu Arg Leu Lys Leu Ser Pro Ser
385                 390                 395                 400

Tyr His Trp Leu Glu Ser Asn Val Asp Ala Glu Glu Arg Glu Val Val
                405                 410                 415

Val Glu Glu Asp Arg Trp Ala Cys Ala Gly His Val Ala Pro Ser
                420                 425                 430

Val Gly Thr Leu Cys Ser His Gly His Leu His Ser Gly Ala Ser Gly
            435                 440                 445

Pro Lys Ala Glu Ala Leu Leu Gln Glu Gly Leu Leu Leu Ser Pro
450                 455                 460

His Met Gln Lys Ala Leu Glu Gly Val His Tyr Ile Ala Asp His Leu
465                 470                 475                 480

Arg Ser Glu Asp Ala Asp Ser Ser Val Lys Glu Asp Trp Lys Tyr Val
                485                 490                 495

Ala Met Val Ile Asp Arg Ile Phe Leu Trp Leu Phe Ile Ile Val Cys
                500                 505                 510

Phe Leu Gly Thr Ile Gly Leu Phe Leu Pro Pro Phe Leu Ala Gly Met
            515                 520                 525

Ile
```

(2) INFORMATION FOR SEQ ID NO: 3:

(i) SEQUENCE CHARACTERISTICS:
        (A) LENGTH: 1654 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 39..1553
        (D) OTHER INFORMATION: /product= "ALPHA-3 SUBUNIT"

(xi) SEQUENCE DESCRIPTION: SEQ ID NO: 3:

```
CCGACCGTCC GGGTCCGCGG CCAGCCCGGC CACCAGCCAT GGGCTCTGGC CCGCTCTCGC      60

TGCCCCTGGC GCTGTCGCCG CCGCGGCTGC TGCTGCTGCT GCTGTCTCTG CTGCCAGTGG     120

CCAGGGCCTC AGAGGCTGAG CACCGTCTAT TTGAGCGGCT GTTTGAAGAT TACAATGAGA     180
```

```
TCATCCGGCC TGTAGCCAAC GTGTCTGACC CAGTCATCAT CCATTTCGAG GTGTCCATGT      240

CTCAGCTGGT GAAGGTGGAT GAAGTAAACC AGATCATGGA GACCAACCTG TGGCTCAAGC      300

AAATCTGGAA TGACTACAAG CTGAAGTGGA ACCCCTCTGA CTATGGTGGG GCAGAGTTCA      360

TGCGTGTCCC TGCACAGAAG ATCTGGAAGC CAGACATTGT GCTGTATAAC AATGCTGTTG      420

GGGATTTCCA GGTGGACGAC AAGACCAAAG CCTTACTCAA GTACACTGGG GAGGTGACTT      480

GGATACCTCC GGCCATCTTT AAGAGCTCCT GTAAAATCGA CGTGACCTAC TTCCCGTTTG      540

ATTACCAAAA CTGTACCATG AAGTTCGGTT CCTGGTCCTA CGATAAGGCG AAAATCGATC      600

TGGTCCTGAT CGGCTCTTCC ATGAACCTCA AGGACTATTG GGAGAGCGGC GAGTGGGCCA      660

TCATCAAAGC CCCAGGCTAC AAACACGACA TCAAGTACAG CTGCTGCGAG GAGATCTACC      720

CCGACATCAC ATACTCGCTG WWCATCCGGC GGCTGTCGTT GTTCTACACC ATCAWCCTCA      780

TCATCCGCTG GCTGATCATC TCCTTCATCA CTGTGGTCGT CTCCTACCTG CCCTCCGACT      840

GCGGCGAGAA GGTGACCCTG TGYATTTCTG TCCTCCTCTC CCTGACGGTG TTTCTCCTGG      900

TGATCACTGA GACCATCCCT TCCACCTCGC TGGTCATCCC CCTGATTGGA GAGTACCTCC      960

TGWWCACCAT GATTTGTGTA ACCTTGTCCA TCGACATCAC CGTCTGCGTG CTCAACGTGC     1020

ACTACAGAAC CCCGACGACA CACACAATGC CCTCATGGGT GAAGACTGTA TTCTTGAMCC     1080

TGCTCCCCAG GGTCATGTWC ATGACCAGGC CAACAAGCAA CGAGGGCAAC GCTCAGAAGC     1140

CGAGGCCCCT CTACGGTGCC GAGCTCTCAA ATCTGAATTG CTTCAGCCGC GCAGAGTCCA     1200

AAGGCTGCAA GGAGGGCTAC CCCTGCCAGG ACGGGATGTG TGGTTACTGC CACCACCGCA     1260

GGATAAAAAT CTCCAATTTC AGTGCTAACC TCACGAGAAG CTCTAGTTCT GAATCTGTTG     1320

ATGCTGTGCT GTCCCTCTCT GCTTTGTCAC CAGAAATCAA AGAAGCCATC CAAAGTGTCA     1380

AGTATATTGC TGAAAATATG AAAGCACAAA ATGAAGCCAA AGAGATTCAA GATGATTGGA     1440

AGTATGTTGC CATGGTGATT GATCGTATTT TTCTGTGGGT TTTCACCCTG GTGTGCATTC     1500

TAGGGACAGC AGGATTGTTT CTGCAACCCC TGATGGCCAG GGAAGATGCA TAAGCACTAA     1560

GCTGTGTGCC TGCCTGGGAG ACTTCCTTGT GTCAGGGCAG GAGGAGGCTG CTTCCTAGTA     1620

AGAACGTACT TTCTGTTATC AAGCTACCAG CTTT                                 1654
```

(2) INFORMATION FOR SEQ ID NO: 4:

(i) SEQUENCE CHARACTERISTICS:
        (A) LENGTH: 504 amino acids
        (B) TYPE: amino acid
        (D) TOPOLOGY: unknown (ii) MOLECULE TYPE: protein (xi) SEQUENCE DESCRIPTION: SEQ ID NO: 4:

```
Met Gly Ser Gly Pro Leu Ser Leu Pro Leu Ala Leu Ser Pro Pro Arg
 1               5                  10                  15

Leu Leu Leu Leu Leu Ser Leu Leu Pro Val Ala Arg Ala Ser Glu
                20                  25                  30

Ala Glu His Arg Leu Phe Glu Arg Leu Phe Glu Asp Tyr Asn Glu Ile
                35                  40                  45

Ile Arg Pro Val Ala Asn Val Ser Asp Pro Val Ile Ile His Phe Glu
            50                  55                  60

Val Ser Met Ser Gln Leu Val Lys Val Asp Glu Val Asn Gln Ile Met
65                  70                  75                  80

Glu Thr Asn Leu Trp Leu Lys Gln Ile Trp Asn Asp Tyr Lys Leu Lys
```

-continued

```
                    85                  90                  95
Trp Asn Pro Ser Asp Tyr Gly Gly Ala Glu Phe Met Arg Val Pro Ala
                100                 105                 110
Gln Lys Ile Trp Lys Pro Asp Ile Val Leu Tyr Asn Asn Ala Val Gly
            115                 120                 125
Asp Phe Gln Val Asp Lys Thr Lys Ala Leu Leu Lys Tyr Thr Gly
        130                 135                 140
Glu Val Thr Trp Ile Pro Pro Ala Ile Phe Lys Ser Ser Cys Lys Ile
145                 150                 155                 160
Asp Val Thr Tyr Phe Pro Phe Asp Tyr Gln Asn Cys Thr Met Lys Phe
                165                 170                 175
Gly Ser Trp Ser Tyr Asp Lys Ala Lys Ile Asp Leu Val Leu Ile Gly
                180                 185                 190
Ser Ser Met Asn Leu Lys Asp Tyr Trp Glu Ser Gly Glu Trp Ala Ile
            195                 200                 205
Ile Lys Ala Pro Gly Tyr Lys His Asp Ile Lys Tyr Ser Cys Cys Glu
        210                 215                 220
Glu Ile Tyr Pro Asp Ile Thr Tyr Ser Leu Xaa Ile Arg Arg Leu Ser
225                 230                 235                 240
Leu Phe Tyr Thr Ile Xaa Leu Ile Ile Arg Trp Leu Ile Ile Ser Phe
                245                 250                 255
Ile Thr Val Val Val Ser Tyr Leu Pro Ser Asp Cys Gly Glu Lys Val
                260                 265                 270
Thr Leu Cys Ile Ser Val Leu Leu Ser Leu Thr Val Phe Leu Leu Val
            275                 280                 285
Ile Thr Glu Thr Ile Pro Ser Thr Ser Leu Val Ile Pro Leu Ile Gly
        290                 295                 300
Glu Tyr Leu Leu Xaa Thr Met Ile Cys Val Thr Leu Ser Ile Asp Ile
305                 310                 315                 320
Thr Val Cys Val Leu Asn Val His Tyr Arg Thr Pro Thr Thr His Thr
                325                 330                 335
Met Pro Ser Trp Val Lys Thr Val Phe Leu Xaa Leu Leu Pro Arg Val
                340                 345                 350
Met Xaa Met Thr Arg Pro Thr Ser Asn Glu Gly Asn Ala Gln Lys Pro
            355                 360                 365
Arg Pro Leu Tyr Gly Ala Glu Leu Ser Asn Leu Asn Cys Phe Ser Arg
        370                 375                 380
Ala Glu Ser Lys Gly Cys Lys Glu Gly Tyr Pro Cys Gln Asp Gly Met
385                 390                 395                 400
Cys Gly Tyr Cys His His Arg Arg Ile Lys Ile Ser Asn Phe Ser Ala
                405                 410                 415
Asn Leu Thr Arg Ser Ser Ser Glu Ser Val Asp Ala Val Leu Ser
            420                 425                 430
Leu Ser Ala Leu Ser Pro Glu Ile Lys Glu Ala Ile Gln Ser Val Lys
        435                 440                 445
Tyr Ile Ala Glu Asn Met Lys Ala Gln Asn Glu Ala Lys Glu Ile Gln
    450                 455                 460
Asp Asp Trp Lys Tyr Val Ala Met Val Ile Asp Arg Ile Phe Leu Trp
465                 470                 475                 480
Val Phe Thr Leu Val Cys Ile Leu Gly Thr Ala Gly Leu Phe Leu Gln
            485                 490                 495
Pro Leu Met Ala Arg Glu Asp Ala
            500
```

(2) INFORMATION FOR SEQ ID NO: 5:

(i) SEQUENCE CHARACTERISTICS:
(A) LENGTH: 2363 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 173..2056
(D) OTHER INFORMATION: /product= "ALPHA-4 SUBUNIT"

(xi) SEQUENCE DESCRIPTION: SEQ ID NO: 5:

```
GCGCTCGCTG CGGCGCCGCC GCCGCNCCGC GCGCCACAGG AGAAGGCGAN CCGGGCCCGG      60
CGGCCGAAGC GGCCCGCGAG GCGCGGGAGG CATGAAGTTG GGCGCGCACG GGCCTCGAAG     120
CGGCGGGGAG CCGGGAGCCG CCCGCATCTA GAGCCCGCGA GGTGCGTGCG CCATGGAGCT     180
AGGGGGCCCC GGAGCGCCGC GGCTGCTGCC GCCGCTGCTG CTGCTTCTGG GGACCGGCCT     240
CCTGCGCGCC AGCAGCCATG TGGAGACCCG GGCCCACGCC GAGGAGCGGC TCCTGAAGAA     300
ACTCTTCTCC GGTTACAACA AGTGGTCCCG ACCCGTGGCC AACATCTCGG ACGTGGTCCT     360
CGTCCGCTTC GGCCTGTCCA TCGCTCAGCT CATTGACGTG GATGAGAAGA ACCAGATGAT     420
GACCACGAAC GTCTGGGTGA AGCAGGAGTG GCACGACTAC AAGCTGCGCT GGGACCCAGC     480
TGACTATGAG AATGTCACCT CCATCCGCAT CCCCTCCGAG CTCATCTGGC GGCCGGACAT     540
CGCCCTCTAC AACAATGCTG ACGGGGACTT CGCGGCCACC CACCTGACCA AGGCCCACCT     600
GTTCCATGAC GGGCGGGTGC AGCGGACTCC CCCGGCCATT TACAAGAGCT CCTGCAGCAT     660
CGACGTCACC TTCTTCCCCT TCGACCAGCA GAACTGCACC ATGAAATTCG GCTCCTGGAC     720
CTACGACAAG GCCAAGATCG ACCTGGTGAA CATGCACAGC CGCGTGGACC AGCTGGACTT     780
CTGGGAGAGT GGCGAGTGGG TCATCTCGGA CGCCGTGGGC ACCTACAACA CCAGGAAGTA     840
CGAGTGCTGC GCCGAGATCT ACCCGGACAT CACCTATGCC TACGCCATCC GGCGGCTGCC     900
GCTCTTCTAC ACCATCAACC TCATCATCCC CTGGCTGCTC ATCTCCTGCC TCACCGCGCT     960
GGTCTTCTAC CTGCCCTCCG AGTGTGGCGA GAAGATCACG CTGTGCATCT CCGTGCTGCT    1020
GTCGCTCACC GTCTTCCTGC TGCTCATCAC CGAGATCATC CCGTCCACCT CACTGGTCAT    1080
CCCACTCATC GGCGAGTACC TGCTGTTCAC CATGATCTTC GTCACCCTGT CCATCGCCAT    1140
CACGGTCTTC GTGCTCAACG TGCACCACCG CTCGCCACGC ACGCACACCA TGCCCACCTG    1200
GGTACGCAGG GTCTTCCTGG ACATCGTGCC ACGCCTGCTC CTCATGAAGC GGCCGTCCGT    1260
GGTCAAGGAC AATTGCCGGC GGCTCATCGA GTCCATGCAT AAGATGGCCA GTGCCCCGCG    1320
CTTCTGGCCC GAGCCAGAAG GGAGCCCCC TGCCACGAGC GGCACCCAGA GCCTGCACCC    1380
TCCCTCACCG TCCTTCTGCG TCCCCCTGGA TGTGCCGGCT GAGCCTGGGC CTTCCTGCAA    1440
GTCACCCTCC GACCAGCTCC CTCCTCAGCA GCCCCTGGAA GCTGAGAAAG CCAGCCCCCA    1500
CCCCTCGCCT GGACCCTGCC GCCCGCCCCA CGGCACCCAG GCACCAGGGC TGGCCAAAGC    1560
CAGGTCCCTC AGCGTCCAGC ACATGTCCAG CCCTGGCGAA GCGGTGGAAG CGGCGTCCG    1620
GTGCCGGTCT CGGAGCATCC AGTACTGTGT TCCCCGAGAC GATGCCGCCC CGAGGCAGA    1680
TGGCCAGGCT GCCGGCGCCC TGGCCTCTCG CAACAGCCAC TCGGCTGAGC TCCCACCCCC    1740
AGACCAGCCC TCTCCGTGCA AATGCACATG CAAGGAGGAG CCCTCTTCGG TGTCCCCGAG    1800
```

-continued

```
CGCCACGGTC AAGACCCGCA GCACCAAAGC GCCGCCGCCG CACCTGCCCC TGTCGCCGGC    1860

CCTGAGCCGG GCGGTGGAGG GCGTCCAGTA CATTGCAGAC CACCTGAAGG CCGAAGACAC    1920

AGACTTCTCG GTGAAGGAGG ACTGGAAGTA CGTGGCCATG GTCATCGACC GCATCTTCCT    1980

CTGGATGTTC ATCATCGTCT GCCTGCTGGG GACGGTGGGC CTCTTCCTGC CGCCCTGGCT    2040

GGCTGGCATG ATCTAGGAAG GGACCGGGAG CCTGCGTGGC CTGGGGCTGC CGYGCACGGG    2100

GCCAGCATCC ATGCGGCCGG CCTGGGGCCG GGCTGGCTTC TCCCTGGACT CTGTGGGGCC    2160

ACACGTTTGC CAAATTTTCC TTCCTGTTCT GTGTCTGCTG TAAGACGGCC TTGGACGGCG    2220

ACACGGCCTC TGGGGAGACC GAGTGTGGAG CTGCTTCCAG TTGGACTCTS GCCTCAGNAG    2280

GCAGCGGCTT GGAGCAGAGG TGGCGGTCGC CGCCTYCTAC CTGCAGGACT CGGGCTAAGT    2340

CCAGCTCTCC CCCTGCGCAG CCC                                            2363
```

(2) INFORMATION FOR SEQ ID NO: 6:

(i) SEQUENCE CHARACTERISTICS:
        (A) LENGTH: 627 amino acids
        (B) TYPE: amino acid
        (D) TOPOLOGY: unknown (ii) MOLECULE TYPE: protein (xi) SEQUENCE DESCRIPTION: SEQ ID NO: 6:

```
Met Glu Leu Gly Gly Pro Gly Ala Pro Arg Leu Leu Pro Pro Leu Leu
1               5                   10                  15

Leu Leu Leu Gly Thr Gly Leu Leu Arg Ala Ser Ser His Val Glu Thr
            20                  25                  30

Arg Ala His Ala Glu Glu Arg Leu Leu Lys Lys Leu Phe Ser Gly Tyr
        35                  40                  45

Asn Lys Trp Ser Arg Pro Val Ala Asn Ile Ser Asp Val Val Leu Val
    50                  55                  60

Arg Phe Gly Leu Ser Ile Ala Gln Leu Ile Asp Val Asp Glu Lys Asn
65                  70                  75                  80

Gln Met Met Thr Thr Asn Val Trp Val Lys Gln Glu Trp His Asp Tyr
                85                  90                  95

Lys Leu Arg Trp Asp Pro Ala Asp Tyr Glu Asn Val Thr Ser Ile Arg
            100                 105                 110

Ile Pro Ser Glu Leu Ile Trp Arg Pro Asp Ile Ala Leu Tyr Asn Asn
        115                 120                 125

Ala Asp Gly Asp Phe Ala Ala Thr His Leu Thr Lys Ala His Leu Phe
    130                 135                 140

His Asp Gly Arg Val Gln Arg Thr Pro Pro Ala Ile Tyr Lys Ser Ser
145                 150                 155                 160

Cys Ser Ile Asp Val Thr Phe Phe Pro Phe Asp Gln Gln Asn Cys Thr
                165                 170                 175

Met Lys Phe Gly Ser Trp Thr Tyr Asp Lys Ala Lys Ile Asp Leu Val
            180                 185                 190

Asn Met His Ser Arg Val Asp Gln Leu Asp Phe Trp Glu Ser Gly Glu
        195                 200                 205

Trp Leu Ile Ser Asp Ala Val Gly Thr Tyr Asn Thr Arg Lys Tyr Glu
    210                 215                 220

Cys Cys Ala Glu Ile Tyr Pro Asp Ile Thr Tyr Ala Tyr Ala Ile Arg
225                 230                 235                 240

Arg Leu Pro Leu Phe Tyr Thr Ile Asn Leu Ile Ile Pro Trp Leu Leu
                245                 250                 255
```

```
Ile Ser Cys Leu Thr Ala Leu Val Phe Tyr Leu Pro Ser Glu Cys Gly
            260                 265                 270

Glu Lys Ile Thr Leu Cys Ile Ser Val Leu Leu Ser Leu Thr Val Phe
            275                 280                 285

Leu Leu Leu Ile Thr Glu Ile Ile Pro Ser Thr Ser Leu Val Ile Pro
            290                 295                 300

Leu Ile Gly Glu Tyr Leu Leu Phe Thr Met Ile Phe Val Thr Leu Ser
305                 310                 315                 320

Ile Ala Ile Thr Val Phe Val Leu Asn Val His His Arg Ser Pro Arg
            325                 330                 335

Thr His Thr Met Pro Thr Trp Val Arg Arg Val Phe Leu Asp Ile Val
            340                 345                 350

Pro Arg Leu Leu Leu Met Lys Arg Pro Ser Val Val Lys Asp Asn Cys
            355                 360                 365

Arg Arg Leu Ile Glu Ser Met His Lys Met Ala Ser Ala Pro Arg Phe
            370                 375                 380

Trp Pro Glu Pro Glu Gly Glu Pro Pro Ala Thr Ser Gly Thr Gln Ser
385                 390                 395                 400

Leu His Pro Pro Ser Pro Ser Phe Cys Val Pro Leu Asp Val Pro Ala
            405                 410                 415

Glu Pro Gly Pro Ser Cys Lys Ser Pro Ser Asp Gln Leu Pro Pro Gln
            420                 425                 430

Gln Pro Leu Glu Ala Glu Lys Ala Ser Pro His Pro Ser Pro Gly Pro
            435                 440                 445

Cys Arg Pro Pro His Gly Thr Gln Ala Pro Gly Leu Ala Lys Ala Arg
            450                 455                 460

Ser Leu Ser Val Gln His Met Ser Ser Pro Gly Glu Ala Val Glu Gly
465                 470                 475                 480

Gly Val Arg Cys Arg Ser Arg Ser Ile Gln Tyr Cys Val Pro Arg Asp
            485                 490                 495

Asp Ala Ala Pro Glu Ala Asp Gly Gln Ala Ala Gly Ala Leu Ala Ser
            500                 505                 510

Arg Asn Ser His Ser Ala Glu Leu Pro Pro Asp Gln Pro Ser Pro
            515                 520                 525

Cys Lys Cys Thr Cys Lys Lys Glu Pro Ser Ser Val Ser Pro Ser Ala
            530                 535                 540

Thr Val Lys Thr Arg Ser Thr Lys Ala Pro Pro Pro His Leu Pro Leu
545                 550                 555                 560

Ser Pro Ala Leu Ser Arg Ala Val Glu Gly Val Gln Tyr Ile Ala Asp
            565                 570                 575

His Leu Lys Ala Glu Asp Thr Asp Phe Ser Val Lys Glu Asp Trp Lys
            580                 585                 590

Tyr Val Ala Met Val Ile Asp Arg Ile Phe Leu Trp Met Phe Ile Ile
            595                 600                 605

Val Cys Leu Leu Gly Thr Val Gly Leu Phe Leu Pro Pro Trp Leu Ala
            610                 615                 620

Gly Met Ile
625

(2) INFORMATION FOR SEQ ID NO: 7:

(i) SEQUENCE CHARACTERISTICS:
        (A) LENGTH: 1828 base pairs
        (B) TYPE: nucleic acid
```

```
            (C) STRANDEDNESS: both
            (D) TOPOLOGY: both (ii) MOLECULE TYPE: cDNA (ix) FEATURE:
            (A) NAME/KEY: CDS
            (B) LOCATION: 155..1561
            (D) OTHER INFORMATION: /product= "ALPHA-5 SUBUNIT"

(xi) SEQUENCE DESCRIPTION: SEQ ID NO: 7:

CCCGGCGGGA GCTGTGGCGC GGAGCGGCCC CGCTGCTGCG TCTGCCCTCG TTTTGTCTCA        60

CGACTCACAC TCAGTGCTGC ATTCCCCAAG AGTTCGCGTT CCCCGCGCGG CGGTCGAGAG       120

GCGGCTGCCC GCGGTCCCGC GCGGGCGCGG GGCG ATG GCG GCG CGG GGG TCA          172
                                      Met Ala Ala Arg Gly Ser
                                       1               5

GGG CCC CGC GCG CTC CGC CTG CTG CTC TTG GTC CAG CTG GTC GCG GGG         220
Gly Pro Arg Ala Leu Arg Leu Leu Leu Leu Val Gln Leu Val Ala Gly
             10                  15                  20

CGC TGC GGT CTA GCG GGC GCG GCG GGC GGC GCG CAG AGA GGA TTA TCT         268
Arg Cys Gly Leu Ala Gly Ala Ala Gly Gly Ala Gln Arg Gly Leu Ser
         25                  30                  35

GAA CCT TCT TCT ATT GCA AAA CAT GAA GAT AGT TTG CTT AAG GAT TTA         316
Glu Pro Ser Ser Ile Ala Lys His Glu Asp Ser Leu Leu Lys Asp Leu
     40                  45                  50

TTT CAA GAC TAC GAA AGA TGG GTT CGT CCT GTG GAA CAC CTG AAT GAC         364
Phe Gln Asp Tyr Glu Arg Trp Val Arg Pro Val Glu His Leu Asn Asp
 55                  60                  65                  70

AAA ATA AAA ATA AAA TTT GGA CTT GCA ATA TCT CAA TTG GTG GAT GTG         412
Lys Ile Lys Ile Lys Phe Gly Leu Ala Ile Ser Gln Leu Val Asp Val
                 75                  80                  85

GAT GAG AAA AAT CAG TTA ATG ACA ACA AAC GTC TGG TTG AAA CAG GAA         460
Asp Glu Lys Asn Gln Leu Met Thr Thr Asn Val Trp Leu Lys Gln Glu
             90                  95                 100

TGG ATA GAT GTA AAA TTA AGA TGG AAC CCT GAT GAC TAT GGT GGA ATA         508
Trp Ile Asp Val Lys Leu Arg Trp Asn Pro Asp Asp Tyr Gly Gly Ile
        105                 110                 115

AAA GTT ATA CGT GTT CCT TCA GAC TCT GTC TGG ACA CCA GAC ATC GTT         556
Lys Val Ile Arg Val Pro Ser Asp Ser Val Trp Thr Pro Asp Ile Val
    120                 125                 130

TTG TTT GAT AAT GCA GAT GGA CGT TTT GAA GGG ACC AGT ACG AAA ACA         604
Leu Phe Asp Asn Ala Asp Gly Arg Phe Glu Gly Thr Ser Thr Lys Thr
135                 140                 145                 150

GTC ATC AGG TAC AAT GGC ACT GTC ACC TGG ACT CCA CCG GCA AAC TAC         652
Val Ile Arg Tyr Asn Gly Thr Val Thr Trp Thr Pro Pro Ala Asn Tyr
                155                 160                 165

AAA AGT TCC TGT ACC ATA GAT GTC ACG TTT TTC CCA TTT GAC CTT CAG         700
Lys Ser Ser Cys Thr Ile Asp Val Thr Phe Phe Pro Phe Asp Leu Gln
            170                 175                 180

AAC TGT TCC ATG AAA TTT GGT TCT TGG ACT TAT GAT GGA TCA CAG GTT         748
Asn Cys Ser Met Lys Phe Gly Ser Trp Thr Tyr Asp Gly Ser Gln Val
        185                 190                 195

GAT ATA ATT CTA GAG GAC CAA GAT GTA GAC AAG AGA GAT TTT TTT GAT         796
Asp Ile Ile Leu Glu Asp Gln Asp Val Asp Lys Arg Asp Phe Phe Asp
    200                 205                 210

AAT GGA GAA TGG GAG ATT GTG AGT GCA ACA GGG AGC AAA GGA AAC AGA         844
Asn Gly Glu Trp Glu Ile Val Ser Ala Thr Gly Ser Lys Gly Asn Arg
215                 220                 225                 230

ACC GAC AGC TGT TGC TGG TAT CCG TAT GTC ACT TAC TCA TTT GTA ATC         892
Thr Asp Ser Cys Cys Trp Tyr Pro Tyr Val Thr Tyr Ser Phe Val Ile
                235                 240                 245
```

```
AAG CGC CTG CCT CTC TTT TAT ACC TTG TTC CTT ATA ATA CCC TGT ATT      940
Lys Arg Leu Pro Leu Phe Tyr Thr Leu Phe Leu Ile Ile Pro Cys Ile
        250                 255                 260

GGG CTC TCA TTT TTA ACT GTA CTT GTC TTC TAT CTT CCT TCA AAT GAA      988
Gly Leu Ser Phe Leu Thr Val Leu Val Phe Tyr Leu Pro Ser Asn Glu
            265                 270                 275

GGT GAA AAG ATT TGT CTC TGC ACT TCA GTA CTT GTG TCT TTG ACT GTC      1036
Gly Glu Lys Ile Cys Leu Cys Thr Ser Val Leu Val Ser Leu Thr Val
        280                 285                 290

TTC CTT CTG GTT ATT GAA GAG ATC ATA CCA TCA TCT TCA AAA GTC ATA      1084
Phe Leu Leu Val Ile Glu Glu Ile Ile Pro Ser Ser Ser Lys Val Ile
295                 300                 305                 310

CCT CTA ATT GGA GAG TAT CTG GTA TTT ACC ATG ATT TTT GTG ACA CTG      1132
Pro Leu Ile Gly Glu Tyr Leu Val Phe Thr Met Ile Phe Val Thr Leu
            315                 320                 325

TCA ATT ATG GTA ACC GTC TTC GCT ATC AAC ATT CAT CAT CGT TCT TCC      1180
Ser Ile Met Val Thr Val Phe Ala Ile Asn Ile His His Arg Ser Ser
        330                 335                 340

TCA ACA CAT AAT GCC ATG GCG CCT TTG GTC CGC AAG ATA TTT CTT CAC      1228
Ser Thr His Asn Ala Met Ala Pro Leu Val Arg Lys Ile Phe Leu His
            345                 350                 355

ACG CTT CCC AAA CTG CTT TGC ATG AGA AGT CAT GTA GAC AGG TAC TTC      1276
Thr Leu Pro Lys Leu Leu Cys Met Arg Ser His Val Asp Arg Tyr Phe
        360                 365                 370

ACT CAG AAA GAG GAA ACT GAG AGT GGT AGT GGA CCA AAA TCT TCT AGA      1324
Thr Gln Lys Glu Glu Thr Glu Ser Gly Ser Gly Pro Lys Ser Ser Arg
375                 380                 385                 390

AAC ACA TTG GAA GCT GCG CTC AAT TCT ATT CGC TAC ATT ACA AGA CAC      1372
Asn Thr Leu Glu Ala Ala Leu Asn Ser Ile Arg Tyr Ile Thr Arg His
            395                 400                 405

ATC ATG AAG GAA AAT GAT GTC CGT GAG GTT GTT GAA GAT TGG AAA TTC      1420
Ile Met Lys Glu Asn Asp Val Arg Glu Val Val Glu Asp Trp Lys Phe
        410                 415                 420

ATA GCC CAG GTT CTT GAT CGG ATG TTT CTG TGG ACT TTT CTT TTC GTT      1468
Ile Ala Gln Val Leu Asp Arg Met Phe Leu Trp Thr Phe Leu Phe Val
            425                 430                 435

TCA ATT GTT GGA TCT CTT GGG CTT TTT GTT CCT GTT ATT TAT AAA TGG      1516
Ser Ile Val Gly Ser Leu Gly Leu Phe Val Pro Val Ile Tyr Lys Trp
        440                 445                 450

GCA AAT ATA TTA ATA CCA GTT CAT ATT GGA AAT GCA AAT AAG TGAAGCCTCC   1568
Ala Asn Ile Leu Ile Pro Val His Ile Gly Asn Ala Asn Lys
455                 460                 465

CAAGGGACTG AAGTATACAT TTAGTTAACA CACATATATC TGATGGCACC TATAAAATTA    1628

TGAAAATGTA AGTTATGTGT TAAATTTAGT GCAAGCTTTA ACAGACTAAG TTGCTAACCT    1688

CAATTTATGT TAACAGATGA TCCATTTGAA CAGTTGGCTG TATGACTGAA GTAATAACTG    1748

ATGAGATACA TTTGATCTTG TAAAAATAGC AAAATATTAT CTGAACTGGA CTAGTGAAAA    1808

ATCTAGTATT TGTATCCTGG                                                1828
```

(2) INFORMATION FOR SEQ ID NO: 8:

(i) SEQUENCE CHARACTERISTICS:
        (A) LENGTH: 468 amino acids
        (B) TYPE: amino acid
        (D) TOPOLOGY: linear (ii) MOLECULE TYPE: protein (xi) SEQUENCE DESCRIPTION: SEQ ID NO: 8:

-continued

```
Met Ala Ala Arg Gly Ser Gly Pro Arg Ala Leu Arg Leu Leu Leu Leu
 1               5                  10                  15

Val Gln Leu Val Ala Gly Arg Cys Gly Leu Ala Gly Ala Gly Gly
             20                  25                  30

Ala Gln Arg Gly Leu Ser Glu Pro Ser Ser Ile Ala Lys His Glu Asp
         35                  40                  45

Ser Leu Leu Lys Asp Leu Phe Gln Asp Tyr Glu Arg Trp Val Arg Pro
     50                  55                  60

Val Glu His Leu Asn Asp Lys Ile Lys Ile Lys Phe Gly Leu Ala Ile
 65              70                  75                  80

Ser Gln Leu Val Asp Val Asp Glu Lys Asn Gln Leu Met Thr Thr Asn
             85                  90                  95

Val Trp Leu Lys Gln Glu Trp Ile Asp Val Lys Leu Arg Trp Asn Pro
            100                 105                 110

Asp Asp Tyr Gly Gly Ile Lys Val Ile Arg Val Pro Ser Asp Ser Val
            115                 120                 125

Trp Thr Pro Asp Ile Val Leu Phe Asp Asn Ala Asp Gly Arg Phe Glu
            130                 135                 140

Gly Thr Ser Thr Lys Thr Val Ile Arg Tyr Asn Gly Thr Val Thr Trp
145                 150                 155                 160

Thr Pro Pro Ala Asn Tyr Lys Ser Ser Cys Thr Ile Asp Val Thr Phe
                165                 170                 175

Phe Pro Phe Asp Leu Gln Asn Cys Ser Met Lys Phe Gly Ser Trp Thr
            180                 185                 190

Tyr Asp Gly Ser Gln Val Asp Ile Ile Leu Glu Asp Gln Asp Val Asp
            195                 200                 205

Lys Arg Asp Phe Phe Asp Asn Gly Glu Trp Glu Ile Val Ser Ala Thr
210                 215                 220

Gly Ser Lys Gly Asn Arg Thr Asp Ser Cys Cys Trp Tyr Pro Tyr Val
225                 230                 235                 240

Thr Tyr Ser Phe Val Ile Lys Arg Leu Pro Leu Phe Tyr Thr Leu Phe
                245                 250                 255

Leu Ile Ile Pro Cys Ile Gly Leu Ser Phe Leu Thr Val Leu Val Phe
                260                 265                 270

Tyr Leu Pro Ser Asn Glu Gly Glu Lys Ile Cys Leu Cys Thr Ser Val
            275                 280                 285

Leu Val Ser Leu Thr Val Phe Leu Leu Val Ile Glu Glu Ile Ile Pro
290                 295                 300

Ser Ser Ser Lys Val Ile Pro Leu Ile Gly Glu Tyr Leu Val Phe Thr
305                 310                 315                 320

Met Ile Phe Val Thr Leu Ser Ile Met Val Thr Val Phe Ala Ile Asn
                325                 330                 335

Ile His His Arg Ser Ser Ser Thr His Asn Ala Met Ala Pro Leu Val
            340                 345                 350

Arg Lys Ile Phe Leu His Thr Leu Pro Lys Leu Leu Cys Met Arg Ser
            355                 360                 365

His Val Asp Arg Tyr Phe Thr Gln Lys Glu Glu Thr Glu Ser Gly Ser
            370                 375                 380

Gly Pro Lys Ser Ser Arg Asn Thr Leu Glu Ala Ala Leu Asn Ser Ile
385                 390                 395                 400

Arg Tyr Ile Thr Arg His Ile Met Lys Glu Asn Asp Val Arg Glu Val
                405                 410                 415

Val Glu Asp Trp Lys Phe Ile Ala Gln Val Leu Asp Arg Met Phe Leu
```

-continued

```
                   420                 425                 430
Trp Thr Phe Leu Phe Val Ser Ile Val Gly Ser Leu Gly Leu Phe Val
            435                 440                 445

Pro Val Ile Tyr Lys Trp Ala Asn Ile Leu Ile Pro Val His Ile Gly
    450                 455                 460

Asn Ala Asn Lys
465
```

(2) INFORMATION FOR SEQ ID NO: 9:

(i) SEQUENCE CHARACTERISTICS:
        (A) LENGTH: 1743 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 143..1627
        (D) OTHER INFORMATION: /product= "ALPHA-6 SUBUNIT"

(xi) SEQUENCE DESCRIPTION: SEQ ID NO: 9:

```
CGGGTTTTGA TTTCTGAGAA GACACACACG GATTGCAGTG GGCTTCTGAT GATGTCAAGG      60

TTGGATGCAT GTGGCTGACT GATAGCTCTT TGTTTTCCAC AATCCTTTGC CTAGGAAAAA     120

GGAATCCAAG TGTGTTTTAA CC ATG CTG ACC AGC AAG GGG CAG GGA TTC CTT      172
                        Met Leu Thr Ser Lys Gly Gln Gly Phe Leu
                         1               5                  10

CAT GGG GGC TTG TGT CTC TGG CTG TGT GTG TTC ACA CCT TTC TTT AAA       220
His Gly Gly Leu Cys Leu Trp Leu Cys Val Phe Thr Pro Phe Phe Lys
             15                  20                  25

GGC TGT GTG GGC TGT GCA ACT GAG GAG AGG CTC TTC CAC AAA CTG TTT       268
Gly Cys Val Gly Cys Ala Thr Glu Glu Arg Leu Phe His Lys Leu Phe
         30                  35                  40

TCT CAT TAC AAC CAG TTC ATC AGG CCT GTG GAA AAC GTT TCC GAC CCT       316
Ser His Tyr Asn Gln Phe Ile Arg Pro Val Glu Asn Val Ser Asp Pro
     45                  50                  55

GTC ACG GTA CAC TTT GAA GTG GCC ATC ACC CAG CTG GCC AAC GTG GAT       364
Val Thr Val His Phe Glu Val Ala Ile Thr Gln Leu Ala Asn Val Asp
 60                  65                  70

GAA GTA AAC CAG ATC ATG GAA ACC AAT TTG TGG CTG CGT CAC ATC TGG       412
Glu Val Asn Gln Ile Met Glu Thr Asn Leu Trp Leu Arg His Ile Trp
 75                  80                  85                  90

AAT GAT TAT AAA TTG CGC TGG GAT CCA ATG GAA TAT GAT GGC ATT GAG       460
Asn Asp Tyr Lys Leu Arg Trp Asp Pro Met Glu Tyr Asp Gly Ile Glu
             95                 100                 105

ACT CTT CGC GTT CCT GCA GAT AAG ATT TGG AAG CCC GAC ATT GTT CTC       508
Thr Leu Arg Val Pro Ala Asp Lys Ile Trp Lys Pro Asp Ile Val Leu
         110                 115                 120

TAT AAC AAT GCT GTT GGT GAC TTC CAA GTA GAA GGC AAA ACA AAA GCT       556
Tyr Asn Asn Ala Val Gly Asp Phe Gln Val Glu Gly Lys Thr Lys Ala
     125                 130                 135

CTT CTT AAA TAC AAT GGC ATG ATA ACC TGG ACT CCA CCA GCT ATT TTT       604
Leu Leu Lys Tyr Asn Gly Met Ile Thr Trp Thr Pro Pro Ala Ile Phe
 140                 145                 150

AAG AGT TCC TGC CCT ATG GAT ATC ACC TTT TTC CCT TTT GAT CAT CAA       652
Lys Ser Ser Cys Pro Met Asp Ile Thr Phe Phe Pro Phe Asp His Gln
155                 160                 165                 170

AAC TGT TCC CTA AAA TTT GGT TCC TGG ACG TAT GAC AAA GCT GAA ATT       700
Asn Cys Ser Leu Lys Phe Gly Ser Trp Thr Tyr Asp Lys Ala Glu Ile
```

-continued

```
                175                 180                 185
GAT CTT CTA ATC ATT GGA TCA AAA GTG GAT ATG AAT GAT TTT TGG GAA    748
Asp Leu Leu Ile Ile Gly Ser Lys Val Asp Met Asn Asp Phe Trp Glu
            190                 195                 200

AAC AGT GAA TGG GAA ATC ATT GAT GCC TCT GGC TAC AAA CAT GAC ATC    796
Asn Ser Glu Trp Glu Ile Ile Asp Ala Ser Gly Tyr Lys His Asp Ile
            205                 210                 215

AAA TAC AAC TGT TGT GAA GAG ATA TAC ACA GAT ATA ACC TAT TCT TTC    844
Lys Tyr Asn Cys Cys Glu Glu Ile Tyr Thr Asp Ile Thr Tyr Ser Phe
        220                 225                 230

TAC ATT AGA AGA TTG CCG ATG TTT TAC ACG ATT AAT CTG ATC ATC CCT    892
Tyr Ile Arg Arg Leu Pro Met Phe Tyr Thr Ile Asn Leu Ile Ile Pro
235                 240                 245                 250

TGT CTC TTT ATT TCA TTT CTA ACC GTG TTG GTC TTT TAC CTT CCT TCG    940
Cys Leu Phe Ile Ser Phe Leu Thr Val Leu Val Phe Tyr Leu Pro Ser
                255                 260                 265

GAC TGT GGT GAA AAA GTG ACG CTT TGT ATT TCA GTC CTG CTT TCT CTG    988
Asp Cys Gly Glu Lys Val Thr Leu Cys Ile Ser Val Leu Leu Ser Leu
                    270                 275                 280

ACT GTG TTT TTG CTG GTC ATC ACA GAA ACC ATC CCA TCC ACA TCT CTG   1036
Thr Val Phe Leu Leu Val Ile Thr Glu Thr Ile Pro Ser Thr Ser Leu
                285                 290                 295

GTG GTC CCA CTG GTG GGT GAG TAC CTG CTG TTC ACC ATG ATC TTT GTC   1084
Val Val Pro Leu Val Gly Glu Tyr Leu Leu Phe Thr Met Ile Phe Val
300                 305                 310

ACA CTG TCC ATC GTG GTG ACT GTG TTT GTG TTG AAC ATA CAC TAC CGC   1132
Thr Leu Ser Ile Val Val Thr Val Phe Val Leu Asn Ile His Tyr Arg
315                 320                 325                 330

ACC CCA ACC ACG CAC ACA ATG CCC AGG TGG GTG AAG ACA GTT TTC CTG   1180
Thr Pro Thr Thr His Thr Met Pro Arg Trp Val Lys Thr Val Phe Leu
                335                 340                 345

AAG CTG CTG CCC CAG GTC CTG CTG ATG AGG TGG CCT CTG GAC AAG ACA   1228
Lys Leu Leu Pro Gln Val Leu Leu Met Arg Trp Pro Leu Asp Lys Thr
                350                 355                 360

AGG GGC ACA GGC TCT GAT GCA GTG CCC AGA GGC CTT GCC AGG AGG CCT   1276
Arg Gly Thr Gly Ser Asp Ala Val Pro Arg Gly Leu Ala Arg Arg Pro
            365                 370                 375

GCC AAA GGC AAG CTT GCA AGC CAT GGG GAA CCC AGA CAT CTT AAA GAA   1324
Ala Lys Gly Lys Leu Ala Ser His Gly Glu Pro Arg His Leu Lys Glu
380                 385                 390

TGC TTC CAT TGT CAC AAA TCA AAT GAG CTT GCC ACA AGC AAG AGA AGA   1372
Cys Phe His Cys His Lys Ser Asn Glu Leu Ala Thr Ser Lys Arg Arg
395                 400                 405                 410

TTA AGT CAT CAG CCA TTA CAG TGG GTG GTG GAA AAT TCG GAG CAC TCG   1420
Leu Ser His Gln Pro Leu Gln Trp Val Val Glu Asn Ser Glu His Ser
                415                 420                 425

CCT GAA GTT GAA GAT GTG ATT AAC AGT GTT CAG TTC ATA GCA GAA AAC   1468
Pro Glu Val Glu Asp Val Ile Asn Ser Val Gln Phe Ile Ala Glu Asn
                430                 435                 440

ATG AAG AGC CAC AAT GAA ACC AAG GAG GTA GAA GAT GAC TGG AAA TAC   1516
Met Lys Ser His Asn Glu Thr Lys Glu Val Glu Asp Asp Trp Lys Tyr
            445                 450                 455

GTG GCC ATG GTG GTG GAC AGA GTA TTT CTT TGG GTA TTT ATA ATT GTC   1564
Val Ala Met Val Val Asp Arg Val Phe Leu Trp Val Phe Ile Ile Val
460                 465                 470

TGT GTA TTT GGA ACT GCA GGG CTA TTT CTA CAG CCA CTA CTT GGG AAC   1612
Cys Val Phe Gly Thr Ala Gly Leu Phe Leu Gln Pro Leu Leu Gly Asn
475                 480                 485                 490

ACA GGA AAA TCT TAAAATGTAT TTTCTTTTAT GTTCAGAAAT TTACAGACAC        1664
Thr Gly Lys Ser
```

```
Thr Gly Lys Ser
            495

CATATTTGTT CTGCATTCCC TGCCACAAGG AAAGGAAAGC AAAGGCTTCC CACCCAAGTC    1724

CCCCATCTGC TAAAACCCG                                                 1743
```

(2) INFORMATION FOR SEQ ID NO: 10:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Leu Thr Ser Lys Gly Gln Gly Phe Leu His Gly Gly Leu Cys Leu
 1               5                  10                  15

Trp Leu Cys Val Phe Thr Pro Phe Phe Lys Gly Cys Val Gly Cys Ala
                20                  25                  30

Thr Glu Glu Arg Leu Phe His Lys Leu Phe Ser His Tyr Asn Gln Phe
                35                  40                  45

Ile Arg Pro Val Glu Asn Val Ser Asp Pro Val Thr Val His Phe Glu
 50                  55                  60

Val Ala Ile Thr Gln Leu Ala Asn Val Asp Glu Val Asn Gln Ile Met
 65                  70                  75                  80

Glu Thr Asn Leu Trp Leu Arg His Ile Trp Asn Asp Tyr Lys Leu Arg
                85                  90                  95

Trp Asp Pro Met Glu Tyr Asp Gly Ile Glu Thr Leu Arg Val Pro Ala
                100                 105                 110

Asp Lys Ile Trp Lys Pro Asp Ile Val Leu Tyr Asn Asn Ala Val Gly
                115                 120                 125

Asp Phe Gln Val Glu Gly Lys Thr Lys Ala Leu Leu Lys Tyr Asn Gly
                130                 135                 140

Met Ile Thr Trp Thr Pro Pro Ala Ile Phe Lys Ser Ser Cys Pro Met
145                 150                 155                 160

Asp Ile Thr Phe Phe Pro Phe Asp His Gln Asn Cys Ser Leu Lys Phe
                165                 170                 175

Gly Ser Trp Thr Tyr Asp Lys Ala Glu Ile Asp Leu Leu Ile Ile Gly
                180                 185                 190

Ser Lys Val Asp Met Asn Asp Phe Trp Glu Asn Ser Glu Trp Glu Ile
                195                 200                 205

Ile Asp Ala Ser Gly Tyr Lys His Asp Ile Lys Tyr Asn Cys Cys Glu
 210                 215                 220

Glu Ile Tyr Thr Asp Ile Thr Tyr Ser Phe Tyr Ile Arg Arg Leu Pro
225                 230                 235                 240

Met Phe Tyr Thr Ile Asn Leu Ile Ile Pro Cys Leu Phe Ile Ser Phe
                245                 250                 255

Leu Thr Val Leu Val Phe Tyr Leu Pro Ser Asp Cys Gly Glu Lys Val
                260                 265                 270

Thr Leu Cys Ile Ser Val Leu Leu Ser Leu Thr Val Phe Leu Leu Val
                275                 280                 285

Ile Thr Glu Thr Ile Pro Ser Thr Ser Leu Val Val Pro Leu Val Gly
                290                 295                 300

Glu Tyr Leu Leu Phe Thr Met Ile Phe Val Thr Leu Ser Ile Val Val
305                 310                 315                 320
```

```
Thr Val Phe Val Leu Asn Ile His Tyr Arg Thr Pro Thr Thr His Thr
                325                 330                 335

Met Pro Arg Trp Val Lys Thr Val Phe Leu Lys Leu Leu Pro Gln Val
                340                 345                 350

Leu Leu Met Arg Trp Pro Leu Asp Lys Thr Arg Gly Thr Gly Ser Asp
                355                 360                 365

Ala Val Pro Arg Gly Leu Ala Arg Arg Pro Ala Lys Gly Lys Leu Ala
                370                 375                 380

Ser His Gly Glu Pro Arg His Leu Lys Glu Cys Phe His Cys His Lys
385                 390                 395                 400

Ser Asn Glu Leu Ala Thr Ser Lys Arg Arg Leu Ser His Gln Pro Leu
                405                 410                 415

Gln Trp Val Val Glu Asn Ser Glu His Ser Pro Glu Val Glu Asp Val
                420                 425                 430

Ile Asn Ser Val Gln Phe Ile Ala Glu Asn Met Lys Ser His Asn Glu
                435                 440                 445

Thr Lys Glu Val Glu Asp Asp Trp Lys Tyr Val Ala Met Val Val Asp
                450                 455                 460

Arg Val Phe Leu Trp Val Phe Ile Ile Val Cys Val Phe Gly Thr Ala
465                 470                 475                 480

Gly Leu Phe Leu Gln Pro Leu Leu Gly Asn Thr Gly Lys Ser
                485                 490
```

(2) INFORMATION FOR SEQ ID NO: 11:

(i) SEQUENCE CHARACTERISTICS:
        (A) LENGTH: 1876 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 73..1581
        (D) OTHER INFORMATION: /product= "ALPHA-7 SUBUNIT"

(xi) SEQUENCE DESCRIPTION: SEQ ID NO: 11:

```
GGCCGCAGGC GCAGGCCCGG GCGACAGCCG AGACGTGGAG CGCGCCGGCT CGCTGCAGCT    60

CCGGGACTCA ACATGCGCTG CTCGCCGGGA GGCGTCTGGC TGGCGCTGGC CGCGTCGCTC   120

CTGCACGTGT CCCTGCAAGG CGAGTTCCAG AGGAAGCTTT ACAAGGAGCT GGTCAAGAAC   180

TACAATCCCT TGGAGAGGCC CGTGGCCAAT GACTCGCAAC CACTCACCGT CTACTTCTCC   240

CTGAGCCTCC TGCAGATCAT GGACGTGGAT GAGAAGAACC AAGTTTTAAC CACCAACATT   300

TGGCTGCAAA TGTCTTGGAC AGATCACTAT TTACAGTGGA ATGTGTCAGA ATATCCAGGG   360

GTGAAGACTG TTCGTTTCCC AGATGGCCAG ATTTGGAAAC CAGACATTCT TCTCTATAAC   420

AGTGCTGATG AGCGCTTTGA CGCCACATTC CACACTAACG TGTTGGTGAA TTCTTCTGGG   480

CATTGCCAGT ACCTGCCTCC AGGCATATTC AAGAGTTCCT GCTACATCGA TGTACGCTGG   540

TTTCCCTTTG ATGTGCAGCA CTGCAAACTG AAGTTTGGGT CCTGGTCTTA CGGAGGCTGG   600

TCCTTGGATC TGCAGATGCA GGAGGCAGAT ATCAGTGGCT ATATCCCCAA TGGAGAATGG   660

GACCTAGTGG GAATCCCCGG CAAGAGGAGT GAAAGGTTCT ATGAGTGCTG CAAAGAGCCC   720

TACCCCGATG TCACCTTCAC AGTGACCATG CGCCGCAGGA CGCTCTACTA TGGCCTCAAC   780

CTGCTGATCC CCTGTGTGCT CATCTCCGCC CTCGCCCTGC TGGTGTTCCT GCTTCCTGCA   840
```

-continued

```
GATTCCGGGG AGAAGATTTC CCTGGGGATA ACAGTCTTAC TCTCTCTTAC CGTCTTCATG    900

CTGCTCGTGG CTGAGATCAT GCCCGCAACA TCCGATTCGG TACCATTGAT AGCCCAGTAC    960

TTCGCCAGCA CCATGATCAT CGTGGGCCTC TCGGTGGTGG TGACGGTGAT CGTGCTGCAG   1020

TACCACCACC ACGACCCCGA CGGGGGCAAG ATGCCCAAGT GGACCAGAGT CATCCTTCTG   1080

AACTGGTGCG CGTGGTTCCT SCGAATGAAG AGGCCCGGGG AGGACAAGGT GCGCCCGGCC   1140

TGCCAGCACA AGCAGCGGCG CTGCAGCCTG GCCAGTGTGG AGATGAGCGC CGTGGCGCCG   1200

CCGCCCGCCA GCAACGGGAA CCTGCTGTAC ATCGGCTTCC GCGGCCTGGA CGGCGTGCAC   1260

TGTGTCCCGA CCCCCGACTC TGGGGTAGTG TGTGGCCGCA TGGCCTGCTC CCCCACGCAC   1320

GATGAGCACC TCCTGCACGG CGGGCAACCC CCCGAGGGGG ACCCGGACTT GGCCAAGATC   1380

CTGGAGGAGG TCCGCTACAT TGCCAATCGC TTCCGCTGCC AGGACGAAAG CGAGGCGGTC   1440

TGCAGCGAGT GGAAGTTCGC CGCCTGTGTG GTGGACCGCC TGTGCCTCAT GGCCTTCTCG   1500

GTCTTCACCA TCATCTGCAC CATCGGCATC CTGATGTCGG CTCCCAACTT CGTGGAGGCC   1560

GTGTCCAAAG ACTTTGCGTA ACCACGCCTG GTTCTGTACA TGTGGAAAAC TCACAGATGG   1620

GCAAGGCCTT TGGCTTGGCG AGATTTGGGG GTGCTAATCC AGGACAGCAT TACACGCCAC   1680

AACTCCAGTG TTCCCTTCTG GCTGTCAGTC GTGTTGCTTA CGGTTTCTTT GTTACTTTAG   1740

GTAGTAGAAT CTCAGCACTT TGTTTCATAT TCTCAGATGG GCTGATAGAT ATCCTTGGCA   1800

CATCCGTACC ATCGGTCAGC AGGGCCACTG AGTAGTCATT TTGCCCATTA GCCCACTGCC   1860

TGGAAAGCCC TTCGGA                                                   1876
```

(2) INFORMATION FOR SEQ ID NO: 12:

(i) SEQUENCE CHARACTERISTICS:
        (A) LENGTH: 502 amino acids
        (B) TYPE: amino acid
        (D) TOPOLOGY: unknown (ii) MOLECULE TYPE: protein (xi) SEQUENCE DESCRIPTION: SEQ ID NO: 12:

```
Met Arg Cys Ser Pro Gly Gly Val Trp Leu Ala Leu Ala Ala Ser Leu
1               5                  10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
```

```
                    165                 170                 175
Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
            260                 265                 270

Thr Val Phe Met Leu Leu Val Ala Glu Ile Met Pro Ala Thr Ser Asp
            275                 280                 285

Ser Val Pro Leu Ile Ala Gln Tyr Phe Ala Ser Thr Met Ile Ile Val
            290                 295                 300

Gly Leu Ser Val Val Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
                340                 345                 350

Val Arg Pro Ala Cys Gln His Lys Gln Arg Arg Cys Ser Leu Ala Ser
                355                 360                 365

Val Glu Met Ser Ala Val Ala Pro Pro Ala Ser Asn Gly Asn Leu
370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
                420                 425                 430

Leu Ala Lys Ile Leu Glu Glu Val Arg Tyr Ile Ala Asn Arg Phe Arg
                435                 440                 445

Cys Gln Asp Glu Ser Glu Ala Val Cys Ser Glu Trp Lys Phe Ala Ala
        450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
            500

(2) INFORMATION FOR SEQ ID NO: 13:

(i) SEQUENCE CHARACTERISTICS:
        (A) LENGTH: 2448 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 265..1773
```

(D) OTHER INFORMATION: /product= "BETA-2 SUBUNIT"

(xi) SEQUENCE DESCRIPTION: SEQ ID NO: 13:

```
CTCCTCCCCC TCACCGTCCC AATTGTATTC CCTGGAAGAG CAGCCGGAAA AGCCTCCGCC            60

TGCTCATACC AGGATAGGCA AGAAGCTGGT TTCTCCTCGC AGCCGGCTCC CTGAGGCCCA           120

GGAACCACCG CGGCGGCCGG CACCACCTGG ACCCAGCTCC AGGCGGGCGC GGCTTCAGCA           180

CCACGGACAG CGCCCCACCC GCGGCCCTCC CCCCGGCGGC GCGCTCCAGC CGGTGTAGGC           240

GAGGCAGCGA GCTATGCCCG CGGC ATG GCC CGG CGC TGC GGC CCC GTG GCG             291
                           Met Ala Arg Arg Cys Gly Pro Val Ala
                            1               5

CTG CTC CTT GGC TTC GGC CTC CTC CGG CTG TGC TCA GGG GTG TGG GGT            339
Leu Leu Leu Gly Phe Gly Leu Leu Arg Leu Cys Ser Gly Val Trp Gly
 10              15                  20                  25

ACG GAT ACA GAG GAG CGG CTG GTG GAG CAT CTC CTG GAT CCT TCC CGC            387
Thr Asp Thr Glu Glu Arg Leu Val Glu His Leu Leu Asp Pro Ser Arg
                     30                  35                  40

TAC AAC AAG CTT ATC CGC CCA GCC ACC AAT GGC TCT GAG CTG GTG ACA            435
Tyr Asn Lys Leu Ile Arg Pro Ala Thr Asn Gly Ser Glu Leu Val Thr
                 45                  50                  55

GTA CAG CTT ATG GTG TCA CTG GCC CAG CTC ATC AGT GTG CAT GAG CGG            483
Val Gln Leu Met Val Ser Leu Ala Gln Leu Ile Ser Val His Glu Arg
             60                  65                  70

GAG CAG ATC ATG ACC ACC AAT GTC TGG CTG ACC CAG GAG TGG GAA GAT            531
Glu Gln Ile Met Thr Thr Asn Val Trp Leu Thr Gln Glu Trp Glu Asp
         75                  80                  85

TAT CGC CTC ACC TGG AAG CCT GAA GAG TTT GAC AAC ATG AAG AAA GTT            579
Tyr Arg Leu Thr Trp Lys Pro Glu Glu Phe Asp Asn Met Lys Lys Val
 90                  95                 100                 105

CGG CTC CCT TCC AAA CAC ATC TGG CTC CCA GAT GTG GTC CTG TAC AAC            627
Arg Leu Pro Ser Lys His Ile Trp Leu Pro Asp Val Val Leu Tyr Asn
                    110                 115                 120

AAT GCT GAC GGC ATG TAC GAG GTG TCC TTC TAT TCC AAT GCC GTG GTC            675
Asn Ala Asp Gly Met Tyr Glu Val Ser Phe Tyr Ser Asn Ala Val Val
                125                 130                 135

TCC TAT GAT GGC AGC ATC TTC TGG CTG CCG CCT GCC ATC TAC AAG AGC            723
Ser Tyr Asp Gly Ser Ile Phe Trp Leu Pro Pro Ala Ile Tyr Lys Ser
            140                 145                 150

GCA TGC AAG ATT GAA GTA AAG CAC TTC CCA TTT GAC CAG CAG AAC TGC            771
Ala Cys Lys Ile Glu Val Lys His Phe Pro Phe Asp Gln Gln Asn Cys
155                 160                 165

ACC ATG AAG TTC CGT TCG TGG ACC TAC GAC CGC ACA GAG ATC GAC TTG            819
Thr Met Lys Phe Arg Ser Trp Thr Tyr Asp Arg Thr Glu Ile Asp Leu
170                 175                 180                 185

GTG CTG AAG AGT GAG GTG GCC AGC CTG GAC GAC TTC ACA CCT AGT GGT            867
Val Leu Lys Ser Glu Val Ala Ser Leu Asp Asp Phe Thr Pro Ser Gly
                190                 195                 200

GAG TGG GAC ATC GTG GCG CTG CCG GGC CGG CGC AAC GAG AAC CCC GAC            915
Glu Trp Asp Ile Val Ala Leu Pro Gly Arg Arg Asn Glu Asn Pro Asp
            205                 210                 215

GAC TCT ACG TAC GTG GAC ATC ACG TAT GAC TTC ATC ATT CGC CGC AAG            963
Asp Ser Thr Tyr Val Asp Ile Thr Tyr Asp Phe Ile Ile Arg Arg Lys
        220                 225                 230

CCG CTC TTC TAC ACC ATC AAC CTC ATC ATC CCC TGT GTG CTC ATC ACC           1011
Pro Leu Phe Tyr Thr Ile Asn Leu Ile Ile Pro Cys Val Leu Ile Thr
    235                 240                 245

TCG CTA GCC ATC CTT GTC TTC TAC CTG CCA TCC GAC TGT GGC GAG AAG           1059
Ser Leu Ala Ile Leu Val Phe Tyr Leu Pro Ser Asp Cys Gly Glu Lys
250                 255                 260                 265
```

```
ATG ACG TTG TGC ATC TCA GTG CTG CTG GCG CTC ACG GTC TTC CTG CTG      1107
Met Thr Leu Cys Ile Ser Val Leu Leu Ala Leu Thr Val Phe Leu Leu
            270                 275                 280

CTC ATC TCC AAG ATC GTG CCT CCC ACC TCC CTC GAC GTG CCG CTC GTC      1155
Leu Ile Ser Lys Ile Val Pro Pro Thr Ser Leu Asp Val Pro Leu Val
            285                 290                 295

GGC AAG TAC CTC ATG TTC ACC ATG GTG CTT GTC ACC TTC TCC ATC GTC      1203
Gly Lys Tyr Leu Met Phe Thr Met Val Leu Val Thr Phe Ser Ile Val
            300                 305                 310

ACC AGC GTG TGC GTG CTC AAC GTG CAC CAC CGC TCG CCC ACC ACG CAC      1251
Thr Ser Val Cys Val Leu Asn Val His His Arg Ser Pro Thr Thr His
    315                 320                 325

ACC ATG GCG CCC TGG GTG AAG GTC GTC TTC CTG GAG AAG CTG CCC GCG      1299
Thr Met Ala Pro Trp Val Lys Val Val Phe Leu Glu Lys Leu Pro Ala
330                 335                 340                 345

CTG CTC TTC ATG CAG CAG CCA CGC CAT CAT TGC GCC CGT CAG CGC CTG      1347
Leu Leu Phe Met Gln Gln Pro Arg His His Cys Ala Arg Gln Arg Leu
                350                 355                 360

CGC CTG CGG CGA CGC CAG CGT GAG CGC GAG GGC GCT GGA GCC CTC TTC      1395
Arg Leu Arg Arg Arg Gln Arg Glu Arg Glu Gly Ala Gly Ala Leu Phe
            365                 370                 375

TTC CGC GAA GCC CCA GGG GCC GAC TCC TGC ACG TGC TTC GTC AAC CGC      1443
Phe Arg Glu Ala Pro Gly Ala Asp Ser Cys Thr Cys Phe Val Asn Arg
        380                 385                 390

GCG TCG GTG CAG GGG TTG GCC GGG GCC TTC GGG GCT GAG CCT GCA CCA      1491
Ala Ser Val Gln Gly Leu Ala Gly Ala Phe Gly Ala Glu Pro Ala Pro
    395                 400                 405

GTG GCG GGC CCC GGG CGC TCA GGG GAG CCG TGT GGC TGT GGC CTC CGG      1539
Val Ala Gly Pro Gly Arg Ser Gly Glu Pro Cys Gly Cys Gly Leu Arg
410                 415                 420                 425

GAG GCG GTG GAC GGC GTG CGC TTC ATC GCA GAC CAC ATG CGG AGC GAG      1587
Glu Ala Val Asp Gly Val Arg Phe Ile Ala Asp His Met Arg Ser Glu
                430                 435                 440

GAC GAT GAC CAG AGC GTG AGT GAG GAC TGG AAG TAC GTC GCC ATG GTG      1635
Asp Asp Asp Gln Ser Val Ser Glu Asp Trp Lys Tyr Val Ala Met Val
            445                 450                 455

ATC GAC CGC CTC TTC CTC TGG ATC TTT GTC TTT GTC TGT GTC TTT GGC      1683
Ile Asp Arg Leu Phe Leu Trp Ile Phe Val Phe Val Cys Val Phe Gly
        460                 465                 470

ACC ATC GGC ATG TTC CTG CAG CCT CTC TTC CAG AAC TAC ACC ACC ACC      1731
Thr Ile Gly Met Phe Leu Gln Pro Leu Phe Gln Asn Tyr Thr Thr Thr
    475                 480                 485

ACC TTC CTC CAC TCA GAC CAC TCA GCC CCC AGC TCC AAG TGAGGCCCTT       1780
Thr Phe Leu His Ser Asp His Ser Ala Pro Ser Ser Lys
490                 495                 500

CCTCATCTCC ATGCTCTTTC ACCCTGCCAC CCTCTGCTGC ACAGTAGTGT TGGGTGGAGG    1840

ATGGACGAGT GAGCTACCAG GAAGAGGGGC GCTGCCCCCA CAGATCCATC CTTTTGCTTC    1900

ATCTGGAGTC CCTCCTCCCC CACGCCTCCA TCCACACACA GCAGCTCCAA CCTGGAGGCT    1960

GGACCAACTG CTTTGTTTTG GCTGCTCTCC ATCTCTTGTA CCAGCCCAGG CAATAGTGTT    2020

GAGGAGGGGA GCAAGGCTGC TAAGTGGAAG ACAGAGATGG CAGAGCCATC CACCCTGAGG    2080

AGTGACGGGC AAGGGCCAG GAAGGGGACA GGATTGTCTG CTGCCTCCAA GTCATGGGAG     2140

AAGAGGGGTA TAGGACAAGG GGTGGAAGGG CAGGAGCTCA CACCGCACCG GGCTGGCCTG    2200

ACACAATGGT AGCTCTGAAG GGAGGGGAAG AGAGAGGCCT GGGTGTGACC TGACACCTGC    2260

CGCTGCTTGA GTGGACAGCA GCTGGACTGG GTGGGCCCCA CAGTGGTCAG CGATTCCTGC    2320
```

```
CAAGTAGGGT TTAGCCGGGC CCCATGGTCA CAGACCCCTG GGGGAGGCTT CCAGCTCAGT      2380

CCCACAGCCC CTTGCTTCTA AGGGATCCAG AGACCTGCTC CAGATCCTCT TTCCCCACTG      2440

AAGAATTC                                                              2448
```

(2) INFORMATION FOR SEQ ID NO: 14:

(i) SEQUENCE CHARACTERISTICS:
        (A) LENGTH: 502 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Ala Arg Arg Cys Gly Pro Val Ala Leu Leu Leu Gly Phe Gly Leu
 1               5                  10                  15

Leu Arg Leu Cys Ser Gly Val Trp Gly Thr Asp Thr Glu Glu Arg Leu
            20                  25                  30

Val Glu His Leu Leu Asp Pro Ser Arg Tyr Asn Lys Leu Ile Arg Pro
        35                  40                  45

Ala Thr Asn Gly Ser Glu Leu Val Thr Val Gln Leu Met Val Ser Leu
    50                  55                  60

Ala Gln Leu Ile Ser Val His Glu Arg Glu Gln Ile Met Thr Thr Asn
65                  70                  75                  80

Val Trp Leu Thr Gln Glu Trp Glu Asp Tyr Arg Leu Thr Trp Lys Pro
                85                  90                  95

Glu Glu Phe Asp Asn Met Lys Lys Val Arg Leu Pro Ser Lys His Ile
            100                 105                 110

Trp Leu Pro Asp Val Val Leu Tyr Asn Asn Ala Asp Gly Met Tyr Glu
        115                 120                 125

Val Ser Phe Tyr Ser Asn Ala Val Val Ser Tyr Asp Gly Ser Ile Phe
    130                 135                 140

Trp Leu Pro Pro Ala Ile Tyr Lys Ser Ala Cys Lys Ile Glu Val Lys
145                 150                 155                 160

His Phe Pro Phe Asp Gln Gln Asn Cys Thr Met Lys Phe Arg Ser Trp
                165                 170                 175

Thr Tyr Asp Arg Thr Glu Ile Asp Leu Val Leu Lys Ser Glu Val Ala
            180                 185                 190

Ser Leu Asp Asp Phe Thr Pro Ser Gly Glu Trp Asp Ile Val Ala Leu
        195                 200                 205

Pro Gly Arg Arg Asn Glu Asn Pro Asp Asp Ser Thr Tyr Val Asp Ile
    210                 215                 220

Thr Tyr Asp Phe Ile Ile Arg Arg Lys Pro Leu Phe Tyr Thr Ile Asn
225                 230                 235                 240

Leu Ile Ile Pro Cys Val Leu Ile Thr Ser Leu Ala Ile Leu Val Phe
                245                 250                 255

Tyr Leu Pro Ser Asp Cys Gly Glu Lys Met Thr Leu Cys Ile Ser Val
            260                 265                 270

Leu Leu Ala Leu Thr Val Phe Leu Leu Ile Ser Lys Ile Val Pro
        275                 280                 285

Pro Thr Ser Leu Asp Val Pro Leu Val Gly Lys Tyr Leu Met Phe Thr
    290                 295                 300

Met Val Leu Val Thr Phe Ser Ile Val Thr Ser Val Cys Val Leu Asn
305                 310                 315                 320

Val His His Arg Ser Pro Thr Thr His Thr Met Ala Pro Trp Val Lys
```

```
                    325                 330                 335
Val Val Phe Leu Glu Lys Leu Pro Ala Leu Leu Phe Met Gln Gln Pro
            340                 345                 350

Arg His His Cys Ala Arg Gln Arg Leu Arg Leu Arg Arg Arg Gln Arg
            355                 360                 365

Glu Arg Glu Gly Ala Gly Ala Leu Phe Phe Arg Glu Ala Pro Gly Ala
            370                 375                 380

Asp Ser Cys Thr Cys Phe Val Asn Arg Ala Ser Val Gln Gly Leu Ala
385                 390                 395                 400

Gly Ala Phe Gly Ala Glu Pro Ala Pro Val Ala Gly Pro Gly Arg Ser
            405                 410                 415

Gly Glu Pro Cys Gly Cys Gly Leu Arg Glu Ala Val Asp Gly Val Arg
            420                 425                 430

Phe Ile Ala Asp His Met Arg Ser Glu Asp Asp Gln Ser Val Ser
            435                 440                 445

Glu Asp Trp Lys Tyr Val Ala Met Val Ile Asp Arg Leu Phe Leu Trp
450                 455                 460

Ile Phe Val Phe Val Cys Val Phe Gly Thr Ile Gly Met Phe Leu Gln
465                 470                 475                 480

Pro Leu Phe Gln Asn Tyr Thr Thr Thr Thr Phe Leu His Ser Asp His
            485                 490                 495

Ser Ala Pro Ser Ser Lys
            500
```

(2) INFORMATION FOR SEQ ID NO: 15:

(i) SEQUENCE CHARACTERISTICS:
        (A) LENGTH: 1927 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 98..1474
        (D) OTHER INFORMATION: /product= "BETA-3 SUBUNIT"

(xi) SEQUENCE DESCRIPTION: SEQ ID NO: 15:

```
TCGGAACCCC TGTATTTTCT TTTCAAAACC CCCTTTTCCA GTGGAAATGC TCTGTTGTTA      60

AAAAGGAAGA AACTGTCTTT CTGAAACTGA CATCACG ATG CTC CCA GAT TTT ATG     115
                                        Met Leu Pro Asp Phe Met
                                          1               5

CTG GTT CTC ATC GTC CTT GGC ATC CCT TCC TCA GCC ACC ACA GGT TTC     163
Leu Val Leu Ile Val Leu Gly Ile Pro Ser Ser Ala Thr Thr Gly Phe
        10                  15                  20

AAC TCA ATC GCC GAA AAT GAA GAT GCC CTC CTC AGA CAT TTG TTC CAA     211
Asn Ser Ile Ala Glu Asn Glu Asp Ala Leu Leu Arg His Leu Phe Gln
        25                  30                  35

GGT TAT CAG AAA TGG GTC CGC CCT GTA TTA CAT TCT AAT GAC ACC ATA     259
Gly Tyr Gln Lys Trp Val Arg Pro Val Leu His Ser Asn Asp Thr Ile
    40                  45                  50

AAA GTA TAT TTT GGA TTG AAA ATA TCC CAG CTT GTA GAT GTG GAT GAA     307
Lys Val Tyr Phe Gly Leu Lys Ile Ser Gln Leu Val Asp Val Asp Glu
55                  60                  65                  70

AAG AAT CAG CTG ATG ACA ACC AAT GTG TGG CTC AAA CAG GAA TGG ACA     355
Lys Asn Gln Leu Met Thr Thr Asn Val Trp Leu Lys Gln Glu Trp Thr
            75                  80                  85
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GAC | CAC | AAG | TTA | CGC | TGG | AAT | CCT | GAT | GAT | TAT | GGT | GGG | ATC | CAT | TCC | 403  |
| Asp | His | Lys | Leu | Arg | Trp | Asn | Pro | Asp | Asp | Tyr | Gly | Gly | Ile | His | Ser |      |
|     |     |     | 90  |     |     |     | 95  |     |     |     |     | 100 |     |     |     |      |
| ATT | AAA | GTT | CCA | TCA | GAA | TCT | CTG | TGG | CTT | CCT | GAC | ATA | GTT | CTC | TTT | 451  |
| Ile | Lys | Val | Pro | Ser | Glu | Ser | Leu | Trp | Leu | Pro | Asp | Ile | Val | Leu | Phe |      |
|     |     | 105 |     |     |     |     | 110 |     |     |     |     | 115 |     |     |     |      |
| GAA | AAT | GCT | GAC | GGC | CGC | TTC | GAA | GGC | TCC | CTG | ATG | ACC | AAG | GTC | ATC | 499  |
| Glu | Asn | Ala | Asp | Gly | Arg | Phe | Glu | Gly | Ser | Leu | Met | Thr | Lys | Val | Ile |      |
|     | 120 |     |     |     |     | 125 |     |     |     |     | 130 |     |     |     |     |      |
| GTG | AAA | TCA | AAC | GGA | ACT | GTT | GTC | TGG | ACC | CCT | CCC | GCC | AGC | TAC | AAA | 547  |
| Val | Lys | Ser | Asn | Gly | Thr | Val | Val | Trp | Thr | Pro | Pro | Ala | Ser | Tyr | Lys |      |
| 135 |     |     |     | 140 |     |     |     | 145 |     |     |     |     |     | 150 |     |      |
| AGC | TCC | TGC | ACC | ATG | GAC | GTC | ACG | TTT | TTC | CCG | TTC | GAC | CGA | CAG | AAC | 595  |
| Ser | Ser | Cys | Thr | Met | Asp | Val | Thr | Phe | Phe | Pro | Phe | Asp | Arg | Gln | Asn |      |
|     |     |     |     | 155 |     |     |     |     | 160 |     |     |     |     | 165 |     |      |
| TGC | TCC | ATG | AAG | TTT | GGA | TCC | TGG | ACT | TAT | GAT | GGC | ACC | ATG | GTT | GAC | 643  |
| Cys | Ser | Met | Lys | Phe | Gly | Ser | Trp | Thr | Tyr | Asp | Gly | Thr | Met | Val | Asp |      |
|     |     | 170 |     |     |     |     | 175 |     |     |     |     | 180 |     |     |     |      |
| CTC | ATT | TTG | ATC | AAT | GAA | AAT | GTC | GAC | AGA | AAA | GAC | TTC | TTC | GAT | AAC | 691  |
| Leu | Ile | Leu | Ile | Asn | Glu | Asn | Val | Asp | Arg | Lys | Asp | Phe | Phe | Asp | Asn |      |
|     | 185 |     |     |     |     | 190 |     |     |     |     | 195 |     |     |     |     |      |
| GGA | GAA | TGG | GAA | ATA | CTG | AAT | GCA | AAG | GGG | ATG | AAG | GGG | AAC | AGA | AGG | 739  |
| Gly | Glu | Trp | Glu | Ile | Leu | Asn | Ala | Lys | Gly | Met | Lys | Gly | Asn | Arg | Arg |      |
| 200 |     |     |     |     | 205 |     |     |     |     | 210 |     |     |     |     |     |      |
| GAC | GGC | GTG | TAC | TCC | TAT | CCC | TTT | ATC | ACG | TAT | TCC | TTC | GTC | CTG | AGA | 787  |
| Asp | Gly | Val | Tyr | Ser | Tyr | Pro | Phe | Ile | Thr | Tyr | Ser | Phe | Val | Leu | Arg |      |
| 215 |     |     |     |     | 220 |     |     |     |     | 225 |     |     |     |     | 230 |      |
| CGC | CTG | CCT | TTA | TTC | TAT | ACC | CTC | TTT | CTC | ATC | ATC | CCC | TGC | CTG | GGG | 835  |
| Arg | Leu | Pro | Leu | Phe | Tyr | Thr | Leu | Phe | Leu | Ile | Ile | Pro | Cys | Leu | Gly |      |
|     |     |     |     | 235 |     |     |     |     | 240 |     |     |     |     | 245 |     |      |
| CTG | TCT | TTC | CTA | ACA | GTT | CTT | GTG | TTC | TAT | TTA | CCT | TCG | GAT | GAA | GGA | 883  |
| Leu | Ser | Phe | Leu | Thr | Val | Leu | Val | Phe | Tyr | Leu | Pro | Ser | Asp | Glu | Gly |      |
|     |     |     | 250 |     |     |     |     | 255 |     |     |     |     | 260 |     |     |      |
| GAA | AAA | CTT | TCA | TTA | TCC | ACA | TCG | GTC | TTG | GTT | TCT | CTG | ACA | GTT | TTC | 931  |
| Glu | Lys | Leu | Ser | Leu | Ser | Thr | Ser | Val | Leu | Val | Ser | Leu | Thr | Val | Phe |      |
|     |     | 265 |     |     |     |     | 270 |     |     |     |     | 275 |     |     |     |      |
| CTT | TTA | GTG | ATT | GAA | GAA | ATC | ATC | CCA | TCG | TCT | TCC | AAA | GTC | ATT | CCT | 979  |
| Leu | Leu | Val | Ile | Glu | Glu | Ile | Ile | Pro | Ser | Ser | Ser | Lys | Val | Ile | Pro |      |
|     | 280 |     |     |     |     | 285 |     |     |     |     | 290 |     |     |     |     |      |
| CTC | ATT | GGA | GAG | TAC | CTG | CTG | TTC | ATC | ATG | ATT | TTT | GTG | ACC | CTG | TCC | 1027 |
| Leu | Ile | Gly | Glu | Tyr | Leu | Leu | Phe | Ile | Met | Ile | Phe | Val | Thr | Leu | Ser |      |
| 295 |     |     |     |     | 300 |     |     |     |     | 305 |     |     |     |     | 310 |      |
| ATC | ATT | GTT | ACC | GTG | TTT | GTC | ATT | AAC | GTT | CAC | CAC | AGA | TCT | TCT | TCC | 1075 |
| Ile | Ile | Val | Thr | Val | Phe | Val | Ile | Asn | Val | His | His | Arg | Ser | Ser | Ser |      |
|     |     |     |     | 315 |     |     |     |     | 320 |     |     |     |     | 325 |     |      |
| ACG | TAC | CAC | CCC | ATG | GCC | CCC | TGG | GTT | AAG | AGG | CTC | TTT | CTG | CAG | AAA | 1123 |
| Thr | Tyr | His | Pro | Met | Ala | Pro | Trp | Val | Lys | Arg | Leu | Phe | Leu | Gln | Lys |      |
|     |     |     | 330 |     |     |     |     | 335 |     |     |     |     | 340 |     |     |      |
| CTT | CCA | AAA | TTA | CTT | TGC | ATG | AAA | GAT | CAT | GTG | GAT | CGC | TAC | TCA | TCC | 1171 |
| Leu | Pro | Lys | Leu | Leu | Cys | Met | Lys | Asp | His | Val | Asp | Arg | Tyr | Ser | Ser |      |
|     |     | 345 |     |     |     |     | 350 |     |     |     |     | 355 |     |     |     |      |
| CCA | GAG | AAA | GAG | GAG | AGT | CAA | CCA | GTA | GTG | AAA | GGC | AAA | GTC | CTC | GAA | 1219 |
| Pro | Glu | Lys | Glu | Glu | Ser | Gln | Pro | Val | Val | Lys | Gly | Lys | Val | Leu | Glu |      |
|     | 360 |     |     |     |     | 365 |     |     |     |     | 370 |     |     |     |     |      |
| AAA | AAG | AAA | CAG | AAA | CAG | CTT | AGT | GAT | GGA | GAA | AAA | GTT | CTA | GTT | GCT | 1267 |
| Lys | Lys | Lys | Gln | Lys | Gln | Leu | Ser | Asp | Gly | Glu | Lys | Val | Leu | Val | Ala |      |
| 375 |     |     |     | 380 |     |     |     | 385 |     |     |     |     |     | 390 |     |      |
| TTT | TTG | GAA | AAA | GCT | GCT | GAT | TCC | ATT | AGA | TAC | ATT | TCC | AGA | CAT | GTG | 1315 |
| Phe | Leu | Glu | Lys | Ala | Ala | Asp | Ser | Ile | Arg | Tyr | Ile | Ser | Arg | His | Val |      |
|     |     |     | 395 |     |     |     |     | 400 |     |     |     |     | 405 |     |     |      |

```
AAG AAA GAA CAT TTT ATC AGC CAG GTA GTA CAA GAC TGG AAA TTT GTA        1363
Lys Lys Glu His Phe Ile Ser Gln Val Val Gln Asp Trp Lys Phe Val
            410                 415                 420

GCT CAA GTT CTT GAC CGA ATC TTC CTG TGG CTC TTT CTG ATA GTG TCA        1411
Ala Gln Val Leu Asp Arg Ile Phe Leu Trp Leu Phe Leu Ile Val Ser
            425                 430                 435

GCA ACA GGC TCG GTT CTG ATT TTT ACC CCT GCT TTG AAG ATG TGG CTA        1459
Ala Thr Gly Ser Val Leu Ile Phe Thr Pro Ala Leu Lys Met Trp Leu
            440                 445                 450

CAT AGT TAC CAT TAGGAATTTC AAAAGACATA AGTACTAAAT TACACCTTAG            1511
His Ser Tyr His
455

ACCTGACATC TGGCTATCAC ACAGACAGAA TCCAAATGCA TGTGCTTGTT CTACGAACCC      1571

CGAATGCGTT GTCTTTGTGG AAATGGAACA TCTCCTCATG GGAGAAACTC TGGTAAATGT      1631

GCTCATTTGT GGTTGCCATG AGAGTGAGCT GCTTTTAAAG AAAGTGGAGC CTCCTCAGAC      1691

CCCTGCCTTG GCTTTCCCAG ACATTCAGGG AGGGATCATA GGTCCAGGCT TGAGCTCACA      1751

TGTGGCCAGA GTGCACAAAA AGCTGTTGCT ACTTGGTGGA GGAACACCTC CTAGAAGCAG      1811

CAGGCCTCGG TGGTGGGGGA GGGGGGATTC ACCTGGAATT AAGGAAGTCT CGGTGTCGAG      1871

CTATCTGTGT GGGCAGAGCC TGGATCTCCC ACCCTGCACT GGCCTCCTTG GTGCCG         1927

(2) INFORMATION FOR SEQ ID NO: 16:

(i) SEQUENCE CHARACTERISTICS:
        (A) LENGTH: 458 amino acids
        (B) TYPE: amino acid
        (D) TOPOLOGY: linear (ii) MOLECULE TYPE: protein (xi) SEQUENCE DESCRIPTION: SEQ ID NO: 16:

Met Leu Pro Asp Phe Met Leu Val Leu Ile Val Leu Gly Ile Pro Ser
 1               5                  10                  15

Ser Ala Thr Thr Gly Phe Asn Ser Ile Ala Glu Asn Glu Asp Ala Leu
                20                  25                  30

Leu Arg His Leu Phe Gln Gly Tyr Gln Lys Trp Val Arg Pro Val Leu
            35                  40                  45

His Ser Asn Asp Thr Ile Lys Val Tyr Phe Gly Leu Lys Ile Ser Gln
        50                  55                  60

Leu Val Asp Val Asp Glu Lys Asn Gln Leu Met Thr Thr Asn Val Trp
65                  70                  75                  80

Leu Lys Gln Glu Trp Thr Asp His Lys Leu Arg Trp Asn Pro Asp Asp
                85                  90                  95

Tyr Gly Gly Ile His Ser Ile Lys Val Pro Ser Glu Ser Leu Trp Leu
            100                 105                 110

Pro Asp Ile Val Leu Phe Glu Asn Ala Asp Gly Arg Phe Glu Gly Ser
        115                 120                 125

Leu Met Thr Lys Val Ile Val Lys Ser Asn Gly Thr Val Val Trp Thr
    130                 135                 140

Pro Pro Ala Ser Tyr Lys Ser Ser Cys Thr Met Asp Val Thr Phe Phe
145                 150                 155                 160

Pro Phe Asp Arg Gln Asn Cys Ser Met Lys Phe Gly Ser Trp Thr Tyr
                165                 170                 175

Asp Gly Thr Met Val Asp Leu Ile Leu Ile Asn Glu Asn Val Asp Arg
            180                 185                 190
```

```
Lys Asp Phe Phe Asp Asn Gly Glu Trp Glu Ile Leu Asn Ala Lys Gly
        195                 200                 205

Met Lys Gly Asn Arg Arg Asp Gly Val Tyr Ser Tyr Pro Phe Ile Thr
    210                 215                 220

Tyr Ser Phe Val Leu Arg Arg Leu Pro Leu Phe Tyr Thr Leu Phe Leu
225                 230                 235                 240

Ile Ile Pro Cys Leu Gly Leu Ser Phe Leu Thr Val Leu Val Phe Tyr
                245                 250                 255

Leu Pro Ser Asp Glu Gly Glu Lys Leu Ser Leu Ser Thr Ser Val Leu
            260                 265                 270

Val Ser Leu Thr Val Phe Leu Leu Val Ile Glu Glu Ile Ile Pro Ser
            275                 280                 285

Ser Ser Lys Val Ile Pro Leu Ile Gly Glu Tyr Leu Leu Phe Ile Met
        290                 295                 300

Ile Phe Val Thr Leu Ser Ile Ile Val Thr Val Phe Val Ile Asn Val
305                 310                 315                 320

His His Arg Ser Ser Ser Thr Tyr His Pro Met Ala Pro Trp Val Lys
                325                 330                 335

Arg Leu Phe Leu Gln Lys Leu Pro Lys Leu Leu Cys Met Lys Asp His
            340                 345                 350

Val Asp Arg Tyr Ser Ser Pro Glu Lys Glu Glu Ser Gln Pro Val Val
            355                 360                 365

Lys Gly Lys Val Leu Glu Lys Lys Gln Lys Gln Leu Ser Asp Gly
            370                 375                 380

Glu Lys Val Leu Val Ala Phe Leu Glu Lys Ala Ala Asp Ser Ile Arg
385                 390                 395                 400

Tyr Ile Ser Arg His Val Lys Lys Glu His Phe Ile Ser Gln Val Val
                405                 410                 415

Gln Asp Trp Lys Phe Val Ala Gln Val Leu Asp Arg Ile Phe Leu Trp
            420                 425                 430

Leu Phe Leu Ile Val Ser Ala Thr Gly Ser Val Leu Ile Phe Thr Pro
            435                 440                 445

Ala Leu Lys Met Trp Leu His Ser Tyr His
            450                 455

(2) INFORMATION FOR SEQ ID NO: 17:

(i) SEQUENCE CHARACTERISTICS:
        (A) LENGTH: 1915 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 87..1583
        (D) OTHER INFORMATION: /product= "BETA-4 SUBUNIT"

(xi) SEQUENCE DESCRIPTION: SEQ ID NO: 17:

CCGGCGCTCA CTCGACCGCG CGGCTCACGG GTGCCCTGTG ACCCCACAGC GGAGCTCGCG      60

GCGGCTGCCA CCCGGCCCCG CCGGCCATGA GGGCGCGCGCC TTCCCTGGTC CTTTTCTTCC    120

TGGTCGCCCT TTGCGGGCGC GGGAACTGCC GCGTGGCCAA TGCGGAGGAA AAGCTGATGG    180

ACGACCTTCT GAACAAAACC CGTTACAATA ACCTGATCCG CCCAGCCACC AGCTCCTCAC    240

AGCTCATCTC CATCAAGCTG CAGCTCTCCC TGGCCCAGCT TATCAGCGTG AATGAGCGAG    300
```

-continued

```
AGCAGATCAT GACCACCAAT GTCTGGCTGA AACAGGAATG GACTGATTAC CGCCTGACCT    360

GGAACAGCTC CCGCTACGAG GGTGTGAACA TCCTGAGGAT CCCTGCAAAG CGCATCTGGT    420

TGCCTGACAT CGTGCTTTAC AACAACGCCG ACGGGACCTA TGAGGTGTCT GTCTACACCA    480

ACTTGATAGT CCGGTCCAAC GGCAGCGTCC TGTGGCTGCC CCCTGCCATC TACAAGAGCG    540

CCTGCAAGAT TGAGGTGAAG TACTTTCCCT TCGACCAGCA GAACTGCACC CTCAAGTTCC    600

GCTCCTGGAC CTATGACCAC ACGGAGATAG ACATGGTCCT CATGACGCCC ACAGCCAGCA    660

TGGATGACTT TACTCCCAGT GGTGAGTGGG ACATAGTGGC CCTCCCAGGG AGAAGGACAG    720

TGAACCCACA AGACCCCAGC TACGTGGACG TGACTTACGA CTTCATCATC AAGCGCAAGC    780

CTCTGTTCTA CACCATCAAC CTCATCATCC CCTGCGTGCT CACCACCTTG CTGGCCATCC    840

TCGTCTTCTA CCTGCCATCC GACTGCGGCG AGAAGATGAC ACTGTGCATC TCAGTGCTGC    900

TGGCACTGAC ATTCTTCCTG CTGCTCATCT CCAAGATCGT GCCACCCACC TCCCTCGATG    960

TGCCTCTCAT CGGCAAGTAC CTCATGTTCA CCATGGTGCT GGTCACCTTC TCCATCGTCA   1020

CCAGCGTCTG TGTGCTCAAT GTGCACCACC GCTCGCCCAG CACCCACACC ATGGCACCCT   1080

GGGTCAAGCG CTGCTTCCTG CACAAGCTGC CTACCTTCCT CTTCATGAAG CGCCCTGGCC   1140

CCGACAGCAG CCCGGCCAGA GCCTTCCCGC CCAGCAAGTC ATGCGTGACC AAGCCCGAGG   1200

CCACCGCCAC CTCCACCAGC CCCTCCAACT TCTATGGGAA CTCCATGTAC TTTGTGAACC   1260

CCGCCTCTGC AGCTTCCAAG TCTCCAGCCG GCTCTACCCC GGTGGCTATC CCCAGGGATT   1320

TCTGGCTGCG GTCCTCTGGG AGGTTCCGAC AGGATGTGCA GGAGGCATTA GAAGGTGTCA   1380

GCTTCATCGC CCAGCACATG AAGAATGACG ATGAAGACCA GAGTGTCGTT GAGGACTGGA   1440

AGTACGTGGC TATGGTGGTG GACCGGCTGT TCCTGTGGGT GTTCATGTTT GTGTGCGTCC   1500

TGGGCACTGT GGGGCTCTTC CTGCCGCCCC TCTTCCAGAC CCATGCAGCT TCTGAGGGGC   1560

CCTACGCTGC CCAGCGTGAC TGAGGGCCCC CTGGGTTGTG GGGTGAGAGG ATGTGAGTGG   1620

CCGGGTGGGC ACTTTGCTGC TTCTTTCTGG GTTGTGGCCG ATGAGGCCCT AAGTAAATAT   1680

GTGAGCATTG GCCATCAACC CCATCAAACC AGCCACAGCC GTGGAACAGG CAAGGATGGG   1740

GGCCTGGCCT GTCCTCTCTG AATGCCTTGG AGGGATCCCA GGAAGCCCCA GTAGGAGGGA   1800

GCTTCAGACA GTTCAATTCT GGCCTGTCTT CCTTCCCTGC ACCGGGCAAT GGGGATAAAG   1860

ATGACTTCGT AGCAGCACCT ACTATGCTTC AGGCATGGTG CCGGCCTGCC TCTCC        1915
```

(2) INFORMATION FOR SEQ ID NO: 18:

(i) SEQUENCE CHARACTERISTICS:
        (A) LENGTH: 498 amino acids
        (B) TYPE: amino acid
        (D) TOPOLOGY: unknown (ii) MOLECULE TYPE: protein (xi) SEQUENCE DESCRIPTION: SEQ ID NO: 18:

```
Met Arg Arg Ala Pro Ser Leu Val Leu Phe Phe Leu Val Ala Leu Cys
 1               5                  10                  15

Gly Arg Gly Asn Cys Arg Val Ala Asn Ala Glu Glu Lys Leu Met Asp
            20                  25                  30

Asp Leu Leu Asn Lys Thr Arg Tyr Asn Asn Leu Ile Arg Pro Ala Thr
        35                  40                  45

Ser Ser Ser Gln Leu Ile Ser Ile Lys Leu Gln Leu Ser Leu Ala Gln
    50                  55                  60

Leu Ile Ser Val Asn Glu Arg Glu Gln Ile Met Thr Thr Asn Val Trp
```

```
                65                    70                    75                    80
Leu Lys Gln Glu Trp Thr Asp Tyr Arg Leu Thr Trp Asn Ser Ser Arg
                    85                    90                    95

Tyr Glu Gly Val Asn Ile Leu Arg Ile Pro Ala Lys Arg Ile Trp Leu
                    100                   105                   110

Pro Asp Ile Val Leu Tyr Asn Asn Ala Asp Gly Thr Tyr Glu Val Ser
                    115                   120                   125

Val Tyr Thr Asn Leu Ile Val Arg Ser Asn Gly Ser Val Leu Trp Leu
                    130                   135                   140

Pro Pro Ala Ile Tyr Lys Ser Ala Cys Lys Ile Glu Val Lys Tyr Phe
145                 150                   155                   160

Pro Phe Asp Gln Gln Asn Cys Thr Leu Lys Phe Arg Ser Trp Thr Tyr
                    165                   170                   175

Asp His Thr Glu Ile Asp Met Val Leu Met Thr Pro Thr Ala Ser Met
                    180                   185                   190

Asp Asp Phe Thr Pro Ser Gly Glu Trp Asp Ile Val Ala Leu Pro Gly
                    195                   200                   205

Arg Arg Thr Val Asn Pro Gln Asp Pro Ser Tyr Val Asp Val Thr Tyr
            210                   215                   220

Asp Phe Ile Ile Lys Arg Lys Pro Leu Phe Tyr Thr Ile Asn Leu Ile
225                 230                   235                   240

Ile Pro Cys Val Leu Thr Thr Leu Leu Ala Ile Leu Val Phe Tyr Leu
                    245                   250                   255

Pro Ser Asp Cys Gly Glu Lys Met Thr Leu Cys Ile Ser Val Leu Leu
                    260                   265                   270

Ala Leu Thr Phe Phe Leu Leu Leu Ile Ser Lys Ile Val Pro Pro Thr
                    275                   280                   285

Ser Leu Asp Val Pro Leu Ile Gly Lys Tyr Leu Met Phe Thr Met Val
            290                   295                   300

Leu Val Thr Phe Ser Ile Val Thr Ser Val Cys Val Leu Asn Val His
305                 310                   315                   320

His Arg Ser Pro Ser Thr His Thr Met Ala Pro Trp Val Lys Arg Cys
                    325                   330                   335

Phe Leu His Lys Leu Pro Thr Phe Leu Phe Met Lys Arg Pro Gly Pro
                    340                   345                   350

Asp Ser Ser Pro Ala Arg Ala Phe Pro Pro Ser Lys Ser Cys Val Thr
                    355                   360                   365

Lys Pro Glu Ala Thr Ala Thr Ser Thr Ser Pro Ser Asn Phe Tyr Gly
            370                   375                   380

Asn Ser Met Tyr Phe Val Asn Pro Ala Ser Ala Ser Lys Ser Pro
385                 390                   395                   400

Ala Gly Ser Thr Pro Val Ala Ile Pro Arg Asp Phe Trp Leu Arg Ser
                    405                   410                   415

Ser Gly Arg Phe Arg Gln Asp Val Gln Glu Ala Leu Glu Gly Val Ser
                    420                   425                   430

Phe Ile Ala Gln His Met Lys Asn Asp Glu Asp Gln Ser Val Val
                    435                   440                   445

Glu Asp Trp Lys Tyr Val Ala Met Val Val Asp Arg Leu Phe Leu Trp
            450                   455                   460

Val Phe Met Phe Val Cys Val Leu Gly Thr Val Gly Leu Phe Leu Pro
465                 470                   475                   480
```

-continued

```
Pro Leu Phe Gln Thr His Ala Ala Ser Glu Gly Pro Tyr Ala Ala Gln
            485                 490                 495
Arg Asp
```

DNA ENCODING HUMAN α AND β SUBUNITS OF NEURONAL NICOTINIC ACETYLCHOLINE RECEPTOR, CELLS TRANSFORMED THEREWITH, AND RECOMBINANT CELL LINE EXPRESSING A HUMAN α AND β SUBUNIT OF NEURONAL NICOTINIC ACETYLCHOLINE RECEPTOR

This application is a continuation-in-part of U.S. application Ser. No. 08/487,596 filed Jun. 7, 1995, now issued as U.S. Pat. No. 6,440,681 which is now pending, and which is a continuation-in-part of U.S. application Ser. No. 08/149,503, filed Nov. 8, 1993, now abandoned; and a continuation-in-part of U.S. application Ser. No. 08/028,031, filed Mar. 8, 1993, now abandoned; and a continuation-in-part of U.S. application Ser. No. 07/938,154, filed Nov. 30, 1992, now issued as U.S. Pat. No. 5,981,193, which is a continuation-in-part of U.S. application Ser. No. 07/504,455, filed Apr. 3, 1990, now issued as U.S. Pat. No. 5,369,028, each of which is hereby incorporated by reference herein in their entirety.

This invention relates to DNA encoding human neuronal nicotinic acetylcholine receptor protein subunits, as well as the proteins themselves. In particular, human neuronal nicotinic acetylcholine receptor α-subunit-encoding DNA, α-subunit proteins, β-subunit-encoding DNA, β-subunit proteins, and combinations thereof are provided. A non-human cell line expressing a human α-subunit protein is also disclosed.

BACKGROUND OF THE INVENTION

Ligand-gated ion channels provide a means for communication between cells of the central nervous system. These channels convert a signal (e.g., a chemical referred to as a neurotransmitter) that is released by one cell into an electrical signal that propagates along a target cell membrane. A variety of neurotransmitters and neurotransmitter receptors exist in the central and peripheral nervous systems. Five families of ligand-gated receptors, including the nicotinic acetylcholine receptors (NAChRs) of neuromuscular and neuronal origins, have been identified (Stroud et al. (1990) Biochemistry 29:11009–11023). There is, however, little understanding of the manner in which the variety of receptors generates different responses to neurotransmitters or to other modulating ligands in different regions of the nervous system.

The nicotinic acetylcholine receptors (NAChRs) are multisubunit proteins of neuromuscular and neuronal origins. These receptors form ligand-gated ion channels that mediate synaptic transmission between nerve and muscle and between neurons upon interaction with the neurotransmitter acetylcholine (ACh). Since various nicotinic acetylcholine receptor (NAChR) subunits exist, a variety of NAChR compositions (i.e., combinations of subunits) exist. The different NAChR compositions exhibit different specificities for various ligands and are thereby pharmacologically distinguishable. Thus, the nicotinic acetylcholine receptors expressed at the vertebrate neuromuscular junction in vertebrate sympathetic ganglia and in the vertebrate central nervous system have been distinguished on the basis of the effects of various ligands that bind to different NAChR compositions. For example, the elapid α-neurotoxins that block activation of nicotinic acetylcholine receptors at the neuromuscular junction do not block activation of some neuronal nicotinic acetylcholine receptors that are expressed on several different neuron-derived cell lines.

Muscle NAChR is a glycoprotein composed of five subunits with the stoichiometry $\alpha_2\beta(\gamma \text{ or } \in)\delta$. Each of the subunits has a mass of about 50–60 kilodaltons (kd) and is encoded by a different gene. The $\alpha_2\beta(\gamma \text{ or } \in)\delta$ complex forms functional receptors containing two ligand binding sites and a ligand-gated transmembrane channel. Upon interaction with a cholinergic agonist, muscle nicotinic AChRs conduct sodium ions. The influx of sodium ions rapidly short-circuits the normal ionic gradient maintained across the plasma membrane, thereby depolarizing the membrane. By reducing the potential difference across the membrane, a chemical signal is transduced into an electrical signal that signals muscle contraction at the neuromuscular junction.

Functional muscle nicotinic acetylcholine receptors have been formed with αβδγ subunits, αβγ subunits, αβδ subunits, βδγ subunits or αδ subunits, but not with only one subunit (see e.g., Kurosaki et al. (1987) FEBS Lett. 214:253–258; Camacho et al. (1993) J. Neuroscience 13:605–613). In contrast, functional neuronal AChRs (nAChRs) can be formed from α subunits alone or combinations of α and β subunits. The larger α subunit is generally believed to be the ACh-binding subunit and the lower molecular weight β subunit is generally believed to be the structural subunit, although it has not been definitively demonstrated that the β subunit does not have the ability to bind ACh. Each of the subunits which participate in the formation of a functional ion channel are, to the extent they contribute to the structure of the resulting channel, "structural" subunits, regardless of their ability (or inability) to bind ACh. Neuronal AChRs (nAChRs), which are also ligand-gated ion channels, are expressed in ganglia of the autonomic nervous system and in the central nervous system (where they mediate signal transmission), in post-synaptic locations (where they modulate transmission), and in pre- and extra-synaptic locations (where they may have additional functions).

DNA encoding NAChRs has been isolated from several sources. Based on the information available from such work, it has been evident for some time that NAChRs expressed in muscle, in autonomic ganglia, and in the central nervous system are functionally diverse. This functional diversity could be due, at least in part, to the large number of different NAChR subunits which exist. There is an incomplete understanding, however, of how (and which) NAChR subunits combine to generate unique NAChR subtypes, particularly in neuronal cells. Indeed, there is evidence that only certain NAChR subtypes may be involved in diseases such as Alzheimer's disease. Moreover, it is not clear whether NAChRs from analogous tissues or cell types are similar across species.

Accordingly, there is a need for the isolation and characterization of DNAs encoding each human neuronal NAChR subunit, recombinant cells containing such subunits and receptors prepared therefrom. In order to study the function of human neuronal AChRs and to obtain disease-specific pharmacologically active agents, there is also a need to obtain isolated (preferably purified) human neuronal nicotinic AChRs, and isolated (preferably purified) human neuronal nicotinic AChR subunits. In addition, there is also a need to develop assays to identify such pharmacologically active agents.

The availability of such DNAs, cells, receptor subunits and receptor compositions will eliminate the uncertainty of speculating as to human nNAChR structure and function based on predictions drawn from non-human nNAChR data, or human or non-human muscle or ganglia NAChR data.

Therefore, it is an object herein to isolate and characterize DNA encoding subunits of human neuronal nicotinic acetylcholine receptors. It is also an object herein to provide methods for recombinant production of human neuronal nicotinic acetylcholine receptor subunits. It is also an object herein to provide purified receptor subunits and to provide methods for screening compounds to identify compounds that modulate the activity of human neuronal AChRs.

Likewise, it is an object of the present invention to provide a recombinant non-human cell line transformed with a heterologous nucleic acid molecule that encodes a human α subunit of neuronal nAChR.

These and other objects will become apparent to those of skill in the art upon further study of the specification and claims.

BRIEF DESCRIPTION OF THE INVENTION

In accordance with the present invention, there are provided isolated DNAs encoding novel human alpha and beta subunits of neuronal NAChRs. Also provided is a non-human cell line that expresses a human $\alpha_7$ subunit of neuronal nAChR. In particular, isolated DNA encoding human $\alpha_4$, $\alpha_7$, and $\beta_4$ subunits of neuronal NAChRs are provided. Messenger RNA and polypeptides encoded by the above-described DNA are also provided.

Further in accordance with the present invention, there are provided recombinant human neuronal nicotinic AChR subunits, including $\alpha_4$, $\alpha_7$, and $\beta_4$ subunits, as well as methods for the production thereof. In addition, recombinant human neuronal nicotinic acetylcholine receptors containing at least one human neuronal nicotinic AChR subunit are also provided, as well as methods for the production thereof. Further provided are recombinant neuronal nicotinic AChRs that contain a mixture of one or more NAChR subunits encoded by a host cell, and one or more nNAChR subunits encoded by heterologous DNA or RNA (i.e., DNA or RNA as described herein that has been introduced into the host cell), as well as methods for the production thereof.

Plasmids containing DNA encoding the above-described subunits are also provided. Recombinant cells containing the above-described DNA, mRNA or plasmids are also provided herein. Such cells are useful, for example, for replicating DNA, for producing human NAChR subunits and recombinant receptors, and for producing cells that express receptors containing one or more human subunits.

Also provided in accordance with the present invention are methods for identifying cells that express functional nicotinic acetylcholine receptors. Methods for identifying compounds which modulate the activity of NAChRs are also provided. Invention methods employ that isolated DNAS, encoding human α and β subunits of neuronal AChRs and polypeptides encoded thereby.

The DNA, mRNA, vectors, receptor subunits, receptor subunit combinations and cells provided herein permit production of selected neuronal nicotinic AChR receptor subtypes and specific combinations thereof, as well as antibodies to said receptor subunits. This provides a means to prepare synthetic or recombinant receptors and receptor subunits that are substantially free of contamination from many other receptor proteins whose presence can interfere with analysis of a single NAChR subtype. The availability of desired receptor subtypes makes it possible to observe the effect of a drug substance on a particular receptor subtype and to thereby perform initial in vitro screening of the drug substance in a test system that is specific for humans and specific for a human neuronal nicotinic AChR subtype.

The availability of subunit-specific antibodies makes possible the application of the technique of immunohistochemistry to monitor the distribution and expression density of various subunits (e.g., in normal vs diseased brain tissue). Such antibodies could also be employed for diagnostic and therapeutic applications.

The ability to screen drug substances in vitro to determine the effect of the drug on specific receptor compositions should permit the development and screening of receptor subtype-specific or disease-specific drugs. Also, testing of single receptor subunits or specific receptor subtype combinations with a variety of potential agonists or antagonists provides additional information with respect to the function and activity of the individual subunits and should lead to the identification and design of compounds that are capable of very specific interaction with one or more of the receptor subunits or receptor subtypes. The resulting drugs should exhibit fewer unwanted side effects than drugs identified by screening with cells that express a variety of subtypes.

Further in relation to drug development and therapeutic treatment of various disease states, the availability of DNAs encoding human nNACHR subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

DETAILED DESCRIPTION OF THE FIGURES

FIG. 1 presents a restriction map of two pCMV promoter-based vectors, pCMV-T7-2 and pCMV-T7-3.

FIG. 2 presents a restriction map of a pCMV promoter based vector, pcDNA3-KE$\alpha_7$RBS.

Figure 9A:
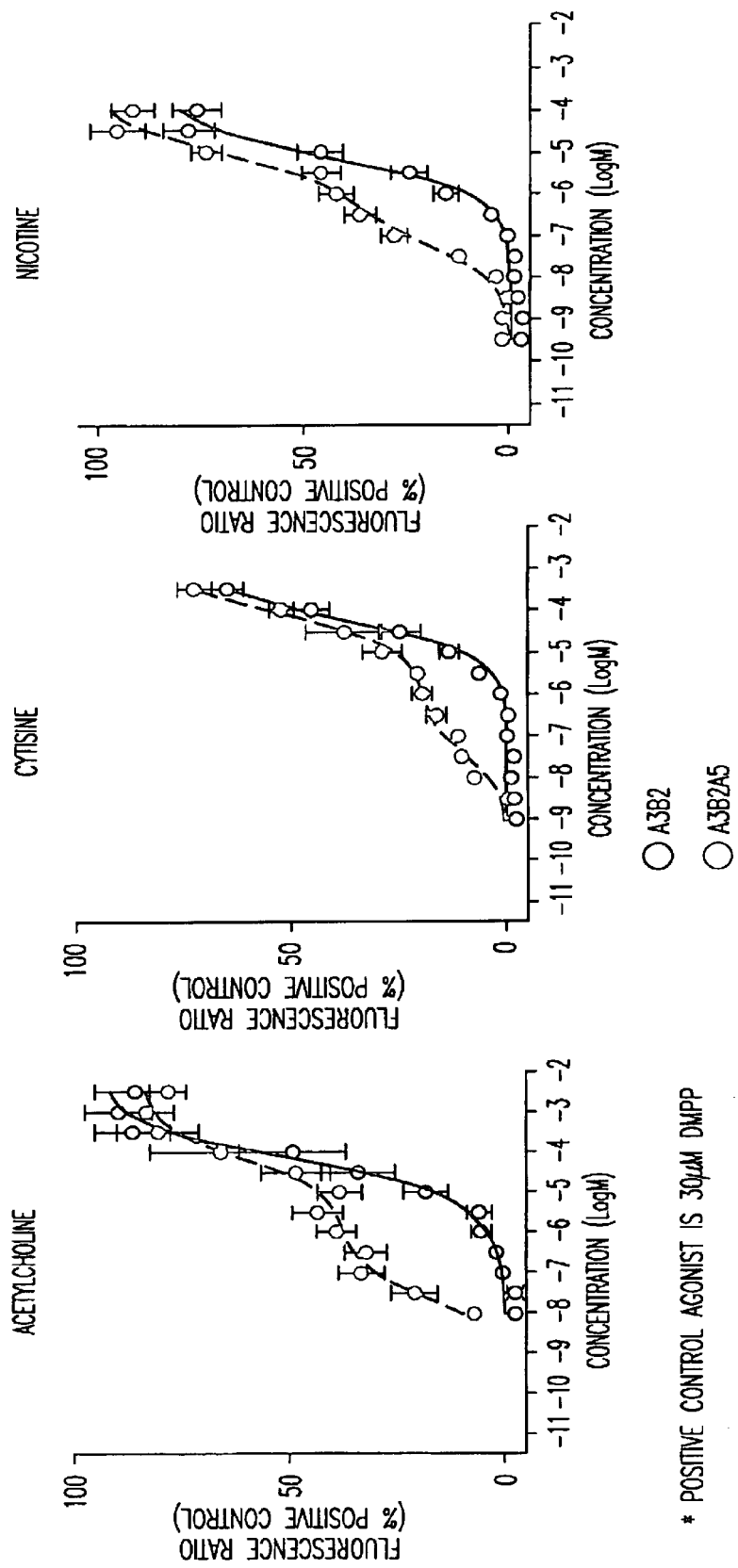
Figure 9B:
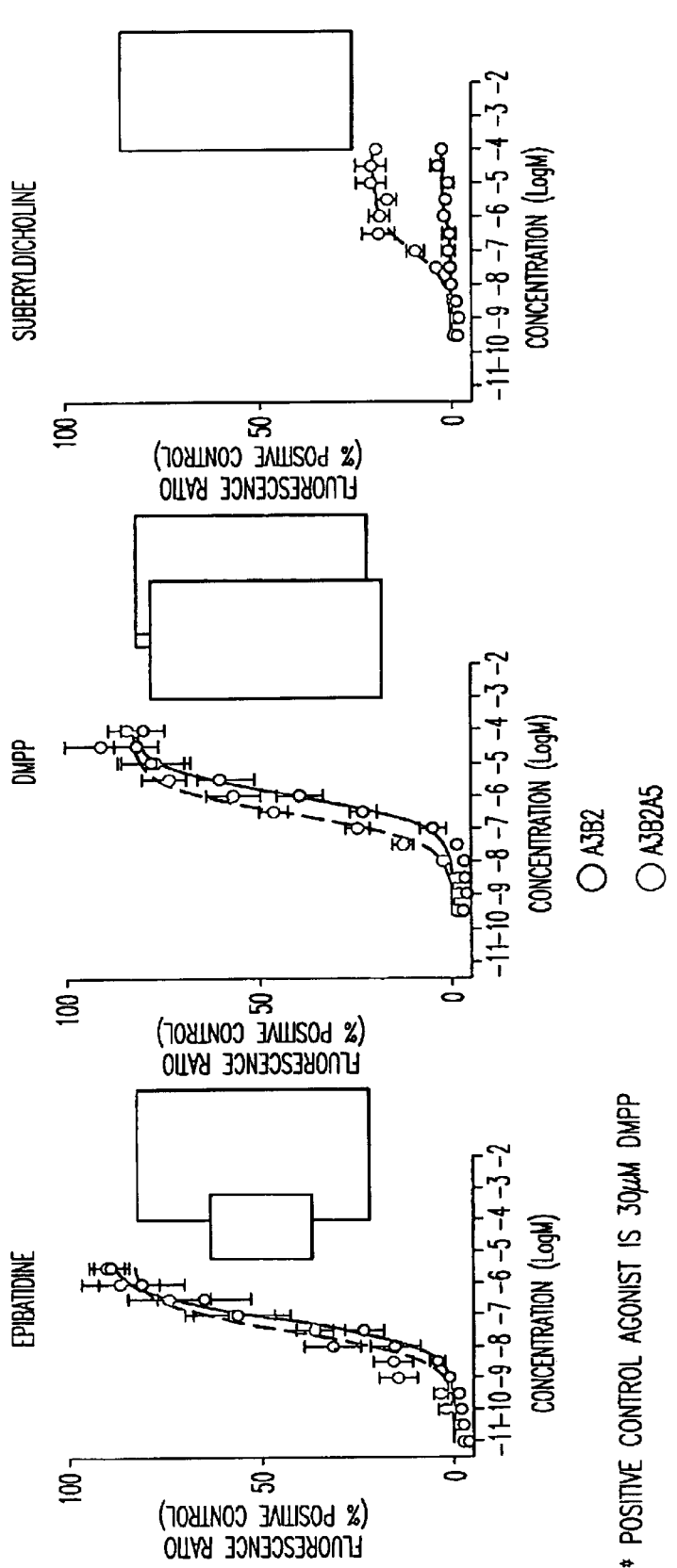

FIGS. 9a–b compares agonist-induced dose-response curves of the alpha3beta2alpha5 expressing cells and alpha3beta2 expressing cells and specifically shows that their profile differs from that of an alpha3beta2 subunit combination.

Figure 10A:
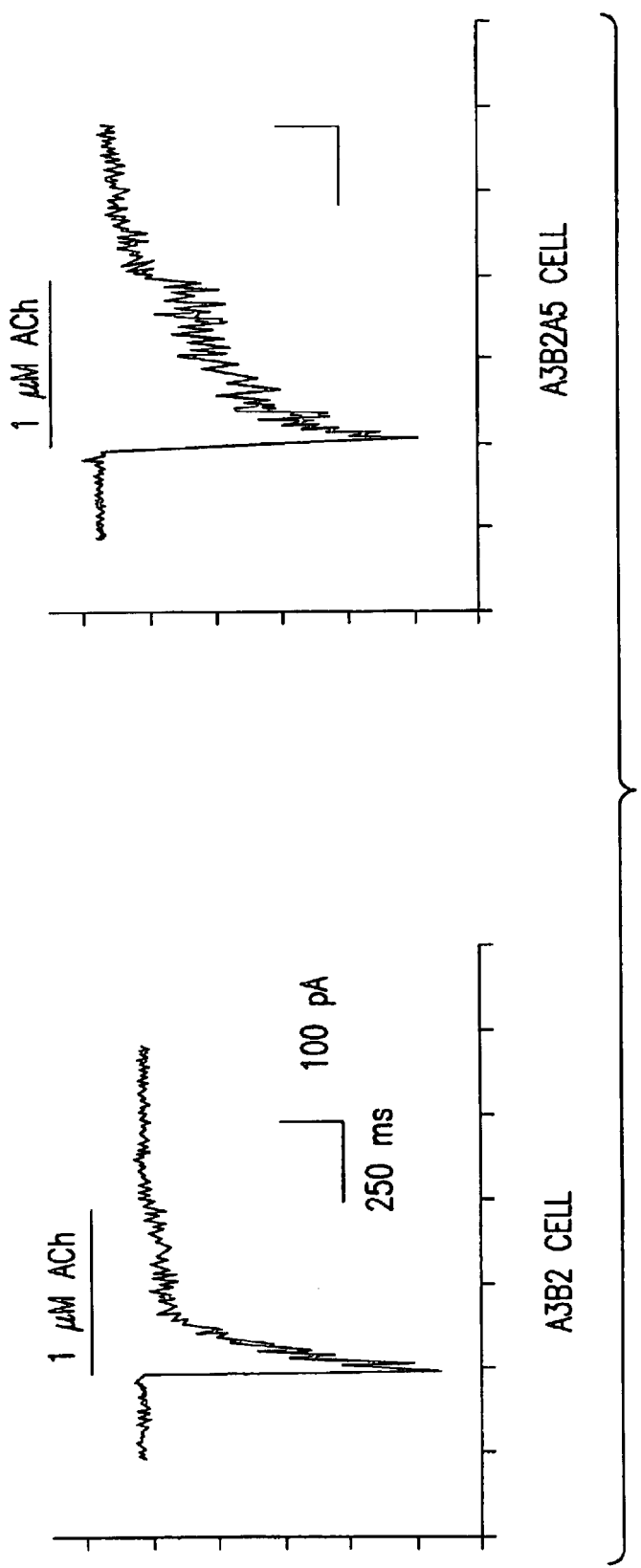
Figure 10B:
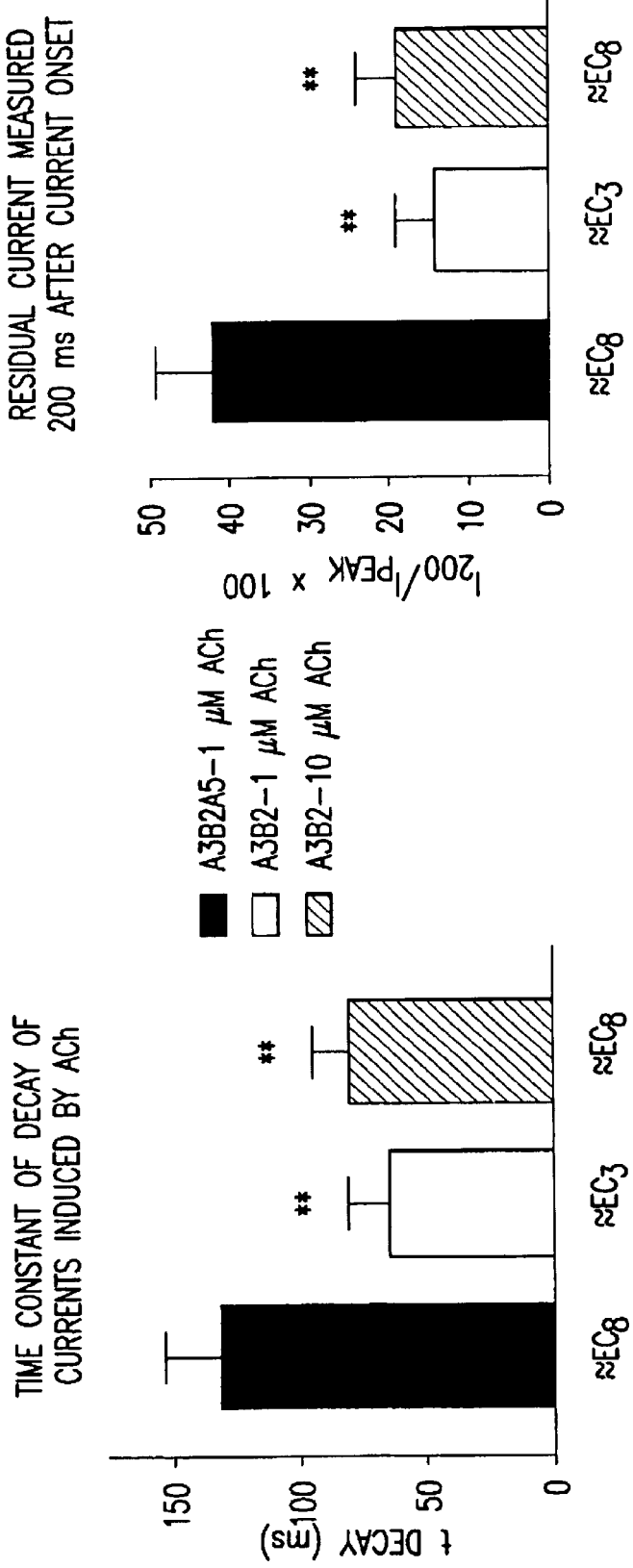

FIG. 10 depicts a comparison in the kinetics of decay of currents induced by acetylcholine between A3B2A5 cells and A3B2 cells.

Figure 11:
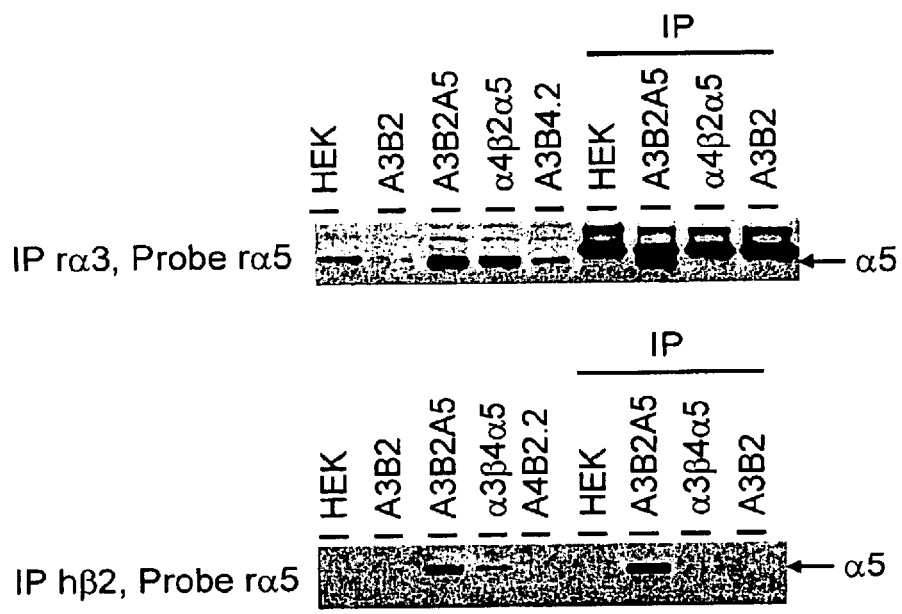

FIG. 11 confirms the association of the alpha3 and beta 2 with alpha 5 subunits in cell line A3B2A5.

Figure 12:
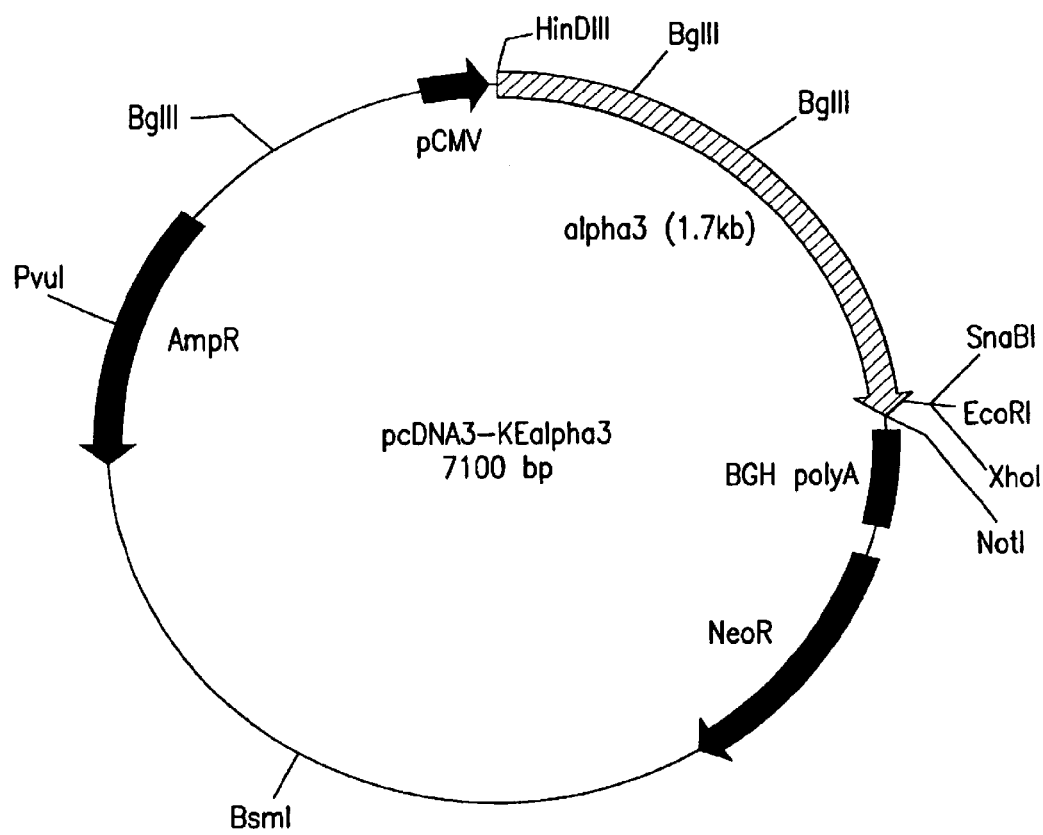

FIG. 12 depicts the expression construct for alpha 3—pc DNA3-KEalpha3

Figure 13:
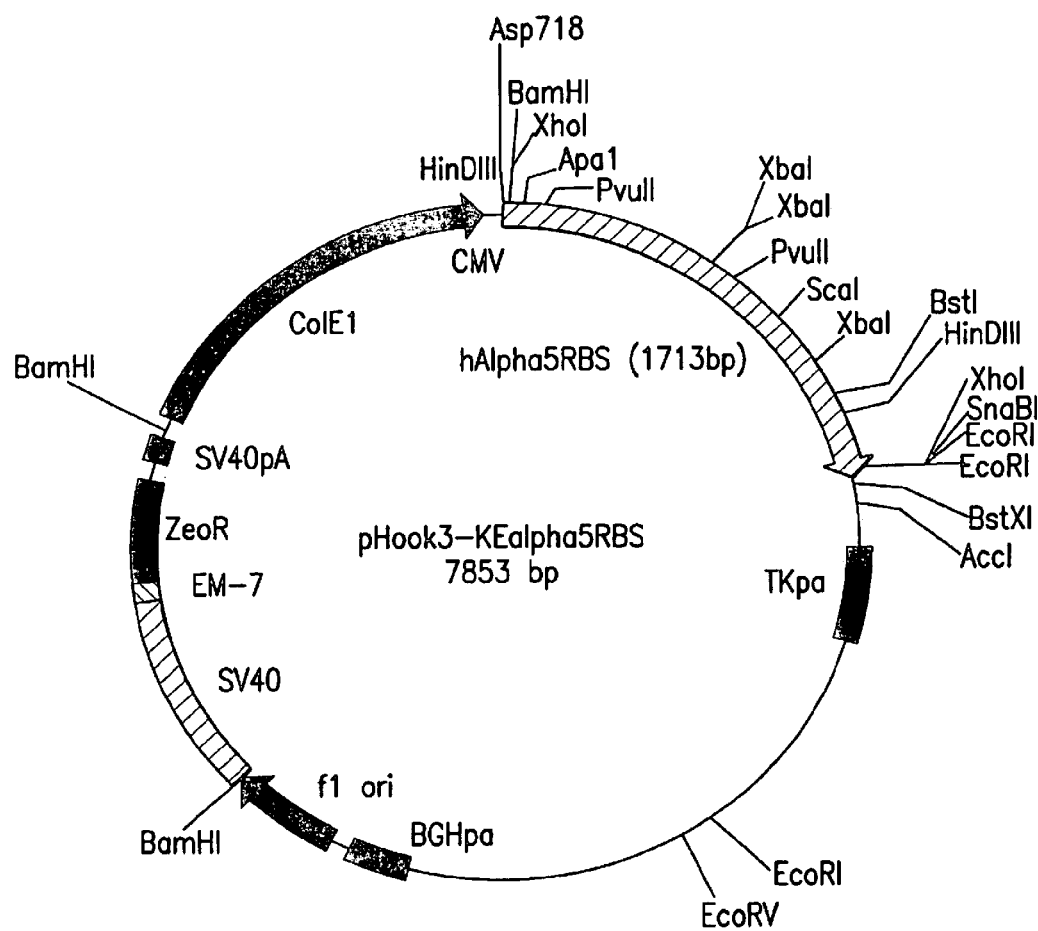

FIG. 13 depicts the expression construct for alpha 5—pHook3-KEalpha5RBS

Figure 14:
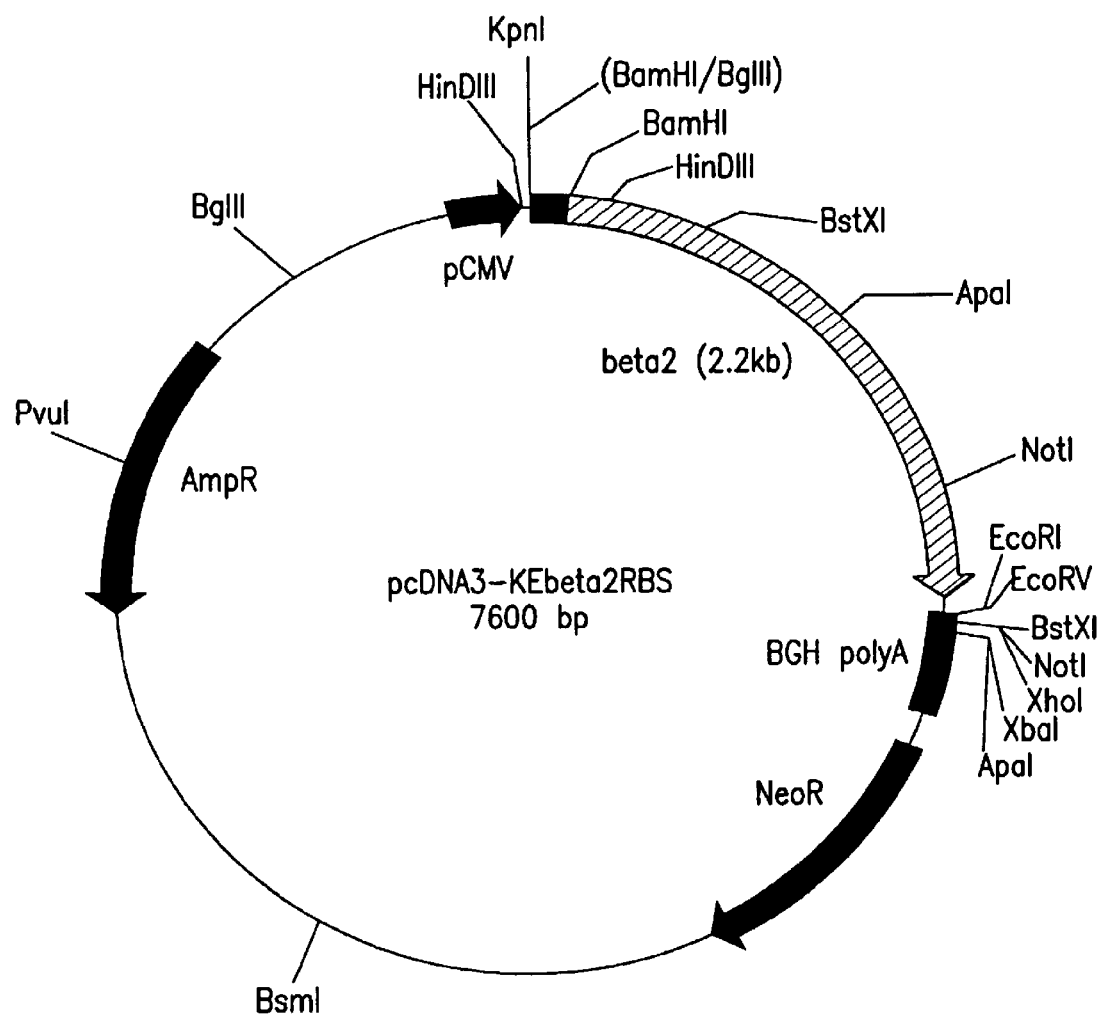

FIG. 14 depicts the expression construct for beta 2—pc DNA3-KEbeta2RBS

DETAILED DESCRIPTION OF THE INVENTION

In accordance with the present invention, we have isolated and characterized DNAs encoding novel human alpha and beta subunits of neuronal nAChR. Specifically, isolated DNAs encoding human $\alpha_4$, $\alpha_7$, and $\beta_4$ subunits of neuronal Anchors are described herein. Recombinant messenger RNA (mRNA) and recombinant polypeptides encoded by the above-described DNA are also provided.

In accordance with the present invention, we have developed methods for identifying compounds that modulate the activity of nAChRs, which employ DNAs encoding human $\alpha$ and $\beta$ subunits of neuronal nAChRs and polypeptides encoded thereby. Specifically, screening methods employing DNAs encoding human $\alpha_2$, $\alpha_3$, $\alpha_4$, $\alpha_5$, $\alpha_6$, $\alpha_7$, $\beta_2$, $\beta_3$, $\beta_4$, subunits of neuronal NAChRs is described herein.

Also described are isolated cells experiencing various multimeric combinations of human $\alpha$ and $\beta$ subunits of neuronal nAChRs, i.e., 3-, 4- and 5-way combinations. A non-human cell line expressing human $\alpha_7$ subunit is also described herein.

As used herein, isolated (or substantially pure) as a modifier of DNA, RNA, polypeptides or proteins means that the DNA, RNA, polypeptides or proteins so designated have been separated from their in vivo cellular environments through the efforts of human beings. Thus as used herein, isolated (or substantially pure) DNA refers to DNAs purified according to standard techniques employed by those skilled in the art (see, e.g., Maniatis et al. (1982) *Molecular Cloning: A Laboratory Manual*, Cold Spring Harbor Laboratory Press, Cold Spring Harbor, N.Y.).

Similarly, as used herein, "recombinant" as a modifier of DNA, RNA, polypeptides or proteins means that the DNA, RNA, polypeptides or proteins so designated have been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

As used herein, a human alpha subunit gene is a gene that encodes an alpha subunit of a human neuronal nicotinic acetylcholine receptor. The alpha subunit is a subunit of the nAChR to which ACh binds. Assignment of the name "alpha" to a putative nNACHR subunit, according to Deneris et al. [Tips (1991) 12:34–40] is based on the conservation of adjacent cysteine residues in the presumed extracellular domain of the subunit that are the homologues of cysteines 192 and 193 of the Torpedo alpha subunit (see Noda et al. (1982) Nature 299:793–797). As used herein, an alpha subunit subtype refers to a human nNAChR subunit that is encoded by DNA that hybridizes under high stringency conditions to at least one of the nNAChR alpha subunit-encoding DNAs (or deposited clones) disclosed herein. An alpha subunit also binds to ACh under physiological conditions and at physiological concentrations and, in the optional presence of a beta subunit (i.e., some alpha subunits are functional alone, while others require the presence of a beta subunit), generally forms a functional AChR as assessed by methods described herein or known to those of skill in this art.

Also contemplated are alpha subunits encoded by DNAs that encode alpha subunits as defined above, but that by virtue of degeneracy of the genetic code do not necessarily hybridize to the disclosed DNA or deposited clones under specified hybridization conditions. Such subunits also form a functional receptor, as assessed by the methods described herein or known to those of skill in the art, generally with one or more beta subunit subtypes. Typically, unless an alpha subunit is encoded by RNA that arises from alternative splicing (i.e., a splice variant), alpha-encoding DNA and the alpha subunit encoded thereby share substantial sequence homology with at least one of the alpha subunit DNAs (and proteins encoded thereby) described or deposited herein. It is understood that DNA or RNA encoding a splice variant may overall share less than 90% homology with the DNA or RNA provided herein, but include regions of nearly 100% homology to a DNA fragment or deposited clone described herein, and encode an open reading frame that includes start and stop codons and encodes a functional alpha subunit.

As used herein, a splice variant refers to variant NAChR subunit-encoding nucleic acid(s) produced by differential processing of primary transcript(s) of genomic DNA, resulting in the production of more than one type of mRNA. cDNA derived from differentially processed genomic DNA will encode NAChR subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10} [Na^+])+0.41(\% G+C)-600/1,$$

where 1 is the length of the hybrids in nucleotides. $T_m$ decreases approximately 1°–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhardt's solution, 5×SSPE. 0.2% SDS at 42° C., followed by washing in 0.1×SSPE, and 0.1% SDS at 65° C.;

(2) MODERATE STRINGENCY refers to conditions equivalent to hybridization in 50% formamide, 5× Denhardt's solution, 5×SSPE, 0.2% SDS at 42° C., followed by washing in 0.2×SSPE, 0.2% SDS, at 65° C.; and (3) LOW STRINGENCY refers to conditions equivalent to hybridization in 10% formamide, 5× Denhardt's solution, 6×SSPE, 0.2% SDS, followed by washing in 1×SSPE, 0.2% SDS, at 50° C.

It is understood that these conditions may be duplicated using a variety of buffers and temperatures and that they are not necessarily precise.

Denhardt's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of NaH$_2$ PO$_4$ and 7.4 g EDTA in 800 ml of water, adjusting the pH to 7.4, and then adding water to 1 liter. Denhardt's solution (see, Denhardt (1966) Biochem. Biophys. Res. Commun. 23:641) can be prepared, for example, as a 50× stock solution by mixing 5 g Ficoll (Type 400, Pharmacia LKB Biotechnology, INC., Piscataway N.J.), 5 g of polyvinylpyrrolidone, 5 g bovine serum albumin (Fraction V; Sigma, St. Louis Mo.) water to 500 ml and filtering to remove particulate matter.

The phrase "substantial sequence homology" is used herein in reference to the nucleotide sequence of DNA, the ribonucleotide sequence of RNA, or the amino acid sequence of protein, that have slight and non-consequential sequence variations from the actual sequences disclosed herein. Species having substantial sequence homology are considered to be equivalent to the disclosed sequences and as such are within the scope of the appended claims. In this regard, "slight and non-consequential sequence variations" mean that "homologous" sequences, i.e., sequences that have substantial homology with the DNA, RNA, or proteins disclosed and claimed herein, are functionally equivalent to the sequences disclosed and claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

In practice, the term substantially the same sequence means that DNA or RNA encoding two proteins hybridize under conditions of high stringency and encode proteins that have the same sequence of amino acids or have changes in sequence that do not alter their structure or function. As used herein, substantially identical sequences of nucleotides share at least about 90% identity, and substantially identical amino acid sequences share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

As used herein, "$\alpha_2$ subunit DNA" refers to DNA that encodes a human neuronal nicotinic acetylcholine receptor subunit of the same name, and to DNA that hybridizes under conditions of high stringency to the DNA of SEQ. ID. No:1, or to the DNA of deposited clone having ATCC Accession No. 68277, or to DNA that encodes the amino acid sequence set forth in SEQ. ID. No:2. Typically, unless an $\alpha_2$ subunit arises as a splice variant, an $\alpha_2$ DNA shares substantial sequence homology (greater than about 90%) with the $\alpha_2$ DNA described herein. DNA or RNA encoding a splice variant may share less than 90% overall sequence homology with the DNA or RNA described herein, but such a splice variant would include regions of nearly 100% homology to the above-described DNA.

As used herein, "$\alpha_3$ subunit DNA" refers to DNA that encodes a neuronal subunit of the same name, and to DNA that hybridizes under conditions of high stringency to the DNA of SEQ. ID. No:3, or to the DNA of deposited clone having ATCC Accession No. 68278, or to DNA that encodes the amino acid sequence set forth in SEQ. ID. No:4 Typically, unless an $\alpha_3$ arises as a splice variant, an $\alpha_3$ DNA shares substantial sequence homology (greater than about 90%) with the $\alpha_3$ DNA described herein. DNA or RNA encoding a splice variant may share less than 90% overall sequence homology with the DNA or RNA provided herein, but such a splice variant would include regions of nearly 100% homology to the above described DNA.

As used herein, "$\alpha_5$ subunit DNA" refers to DNA that encodes a human neuronal nicotinic acetylcholine receptor subunit of the same name, as described, for example, by Chini et al. (1992) Proc. Natl. Acad. Sci. U.S.A. 89:1572–1576.

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid composotions disclosed and claimed herein. In particular, functionally equivalent DNAs encode human-derived proteins that are the same as those disclosed herein or that have conservative amino acid variations, such as substitution on a non-polar residue for another non-polar residue or a charged residue for a similarly chared residue. These changes include those recognized by those of skill in the art as those that do not substantially alter the tertiary structure of the protein.

As used herein, "$\alpha_4$ subunit DNA" refers to DNA encoding a neuronal nicotinic acetylcholine receptor subunit of the same name. Such DNA can be characterized in a number of ways, for example said DNA may encode the amino acid sequence set forth in SEQ. ID. No:6, or said DNA may encode the amino acid sequence encoded by clone HnAChRα4.2, deposited under ATCC Accession No. 69239, or the 5' nucleotides of said DNA may encode the amino acid sequence encoded by clone HnAChRα4.1, deposited under ATCC Accession No. 69152.

Presently preferred $\alpha_4$-encoding DNAs can be characterized as follows said DNA may hybridize to the coding sequence set forth in SEQ. ID. No:5 (preferably to substantially the entire coding sequence thereof, i.e., nucleotides 184–2067) under high stringency conditions, or said DNA may hybridize under high stringency conditions to the sequence (preferably to substantially the entire sequence) of the $\alpha_4$-encoding insert of clone HnAChRα4.2, deposited under ATCC Accession No. 69239, or the 5' nucleotides of said DNA may hybridize under high stringency conditions to the sequence of the $\alpha_4$-encoding insert of clone HnAChRα4.1, deposited under ATCC Accession No. 69152.

Especially preferred $\alpha_4$-encoding DNAs of the invention are characterized as follows DNA having substantially the same nucleotide sequence as the coding region set forth in SEQ. ID. No:5 (i.e., nucleotides 184–2067 thereof), or DNA having substantially the same nucleotide sequence as the $\alpha_4$-encoding insert of clone HnAChR$\alpha$4.2, deposited under ATCC Accession No. 69239, or the 5' nucleotides of said DNA have substantially the same sequence as the $\alpha_4$-encoding insert of clone HnAChR$\alpha$4.1, deposited under ATCC Accession No. 69152.

Typically, unless an $\alpha_4$ subunit arises as a splice variant, $\alpha_4$-encoding DNA will share substantial sequence homology (i.e., greater than about 90%), with the $\alpha_4$ DNAs described or deposited herein. DNA or RNA encoding a splice variant may share less than 90% overall sequence homology with the DNA or RNA provided herein, but such a splice variant would include regions of nearly 100% homology to the above-described DNAs.

As used herein, "$\alpha_3$ subunit DNA" referes to DNA that encodes a human neuronal nicotinic acetylcholine receptor subunit of the same name, and to DNA that hyridizes under conditions of high stringency to the DNA of SEQ ID No. 7, or to DNA that encodes the amino acid sequence set forth in SEQ ID No. 8. Typically, unles an $\alpha_5$ subunit arises as a splice variant, an $\alpha_5$ DNA shares substantial sequence homology (greater than about 90%) with the $\alpha_5$ DNA described herein. DNA or RNA encoding a splice variant may share less than 90% overall sequence homology with the DNA or RNA described herein, but such a splice variant would include regions of nearly 100% homology to the above-described DNA. Human $\alpha_5$ subunit DNA has been described in the art, for example, by Chini et al. (1992) Proc. Natl. Acad. Sci. USA 89: 1572–1576.

As used herein, "$\alpha_6$ subunit DNA" refers to DNA that encodes a neuronal subunit of the same name, and to DNA that hybridizes under conditions of high stringency to the DNA of SEQ ID No. 9, or to DNA that encodes the amino acid sequence set forth in SEQ ID No. 10. Typically, unless and $\alpha_6$ arises as a splice variant, an $\alpha_6$ DNA shares substantial sequence homology (greater than about 90%) with the $\alpha_6$ DNA described herein. DNA or RNA encoding a splice variant may share less than 90% overall sequence homology with the DNA or RNA provided herein, but such a splice variant would include regions of neraly 100% homology to the above described DNA.

As used herein, "$\alpha_7$ subunit DNA" refers to DNA encoding a neuronal nicotinic acetylcholine receptor subunit of the same name. Such DNA can be characterized in a number of ways, for example, the nucleotides of said DNA may encode the amino acid sequence set forth in SEQ ID No: 12. Presently preferred $\alpha_7$-encoding DNAs can be characterized as DNA which hybridizes under high stringency conditions to the coding sequence set forth in SEQ ID No: 11 (preferably to substantially the entire coding sequence thereof, i.e., nucleotides 73–1581). Especially preferred $\alpha_7$-encoding DNAs of the invention are characterized as having substantially the same nucleotide sequence as the coding sequence set forth in SEQ ID No: 11 (i.e., nucleotides 73–1581 thereof).

Typically, unless an $\alpha_7$ subunit arises as a splice variant, $\alpha_7$-encoding DNA will share substantial sequence homology (greater than about 90%) with the $\alpha_7$ DNAs described or deposited herein. DNA or RNA encoding a splice variant may share less than 90% overall sequence homology with the DNA or RNA provided herein, but such DNA would include regions of nearly 100% homology to the above-described DNA.

The $\alpha_7$ subunits derived from the above-described DNA are expected to bind to the neurotoxin $\alpha$-bungarotoxin ($\alpha$-bgtx). The activity of AChRs that contain $\alpha$7 subunits should be inhibited upon interaction with $\alpha$-bgtx. Amino acid residues 210 through 217, as set forth in SEQ. ID. No:8, are believed to be important elements in the binding of $\alpha$-bgtx (see, for example, Chargeux et al. Trends Pharmacol Sci. (1992) 13:299–301).

As used herein, a human beta subunit gene is a gene that encodes a beta subunit of a human neuronal nicotinic acetylcholine receptor. Assignment of the name "beta" to a putative nNAChR subunit, according to Deneris et al. supra, is based on the lack of adjacent cysteine residues (which are characteristic of alpha subunits). The beta subunit is frequently referred to as the structural NAChR subunit (although it is possible that beta subunits also have ACh binding properties). Combination of beta subunit(s) with appropriate alpha subunit(s) leads to the formation of a functional receptor. As used herein, a beta subunit subtype refers to a nNAChR subunit that is encoded by DNA that hybridizes under high stringency conditions to at least one of the nNAChR-encoding DNAs (or deposited clones) disclosed herein. A beta subunit forms a functional NAChR, as assessed by methods described herein or known to those of skill in this art, with appropriate alpha subunit subtype(s).

Also contemplated are beta subunits encoded by DNAs that encode beta subunits as defined above, but that by virtue of degeneracy of the genetic code do not necessarily hybridize to the disclosed DNA or deposited clones under the specified hybridization conditions. Such subunits also form functional receptors, as assessed by the methods described herein or known to those of skill in the art, in combination with appropriate alpha subunit subtype(s). Typically, unless a beta subunit is encoded by RNA that arises as a splice variant, beta-encoding DNA and the beta subunit encoded thereby share substantial sequence homology with the beta-encoding DNA and beta subunit protein described herein. It is understood that DNA or RNA encoding a splice variant may share less than 90% overall homology with the DNA or RNA provided herein, but such DNA will include regions of nearly 100% homology to the DNA described herein.

As used herein, "$\beta_2$ subunit DNA" refers to DNA that encodes a neuronal subunit of the same name and, to DNA that hybridizes under conditions of high stringency to the DNA of SEQ ID No. 13, or to the DNA of deposited clone HnAChR$\beta$2, having ATCC Accession No. 68279, or to DNA encoding the amino acid sequence set forth in SEQ ID No. 14. Typically, unless a $\beta_2$ subunit arises as a splice variant, a $\beta_2$ DNA shares substantial sequence homology (greater than about 90%) with the $\beta_2$ DNA described herein. DNA or RNA encoding a splice variant may share overall less than 90% homology with the DNA or RNA provided herein, but such a splice variant would include regions of nearly 100% homology to the above-described DNA.

As used herein, "$\beta_3$ subunit DNA" refers to DNA that encodes a neuronal subunit of the same name and, to DNA that hybridizes under conditions of high stringency to the DNA of SEQ ID No. 15, or to DNA encoding the amino acid sequence set forth in SEQ ID No. 16. Typically, unless a $\beta_3$ subunit arises as a splice variant, a $\beta_2$ DNA shares substantial sequence homology (greater than about 90%) with the $\beta_3$ DNA described herein. DNA or RNA encoding a splice variant may share overall less than 90% homology with the DNA or RNA provided herein, but such a splice variant would include regions of nearly 100% homology to the above-described DNA.

As used herein, "$\beta_4$ subunit DNA" refers to DNA encoding a neuronal nicotinic acetylcholine receptor subunit of the same name. Such DNA can be characterized in a number of ways, for example, the nucleotides of said DNA may encode the amino acid sequence set forth in SEQ. ID. No:18. Presently preferred $\beta_4$-encoding DNAs can be characterized as DNA which hybridizes under high stringency conditions to the coding sequence set forth in SEQ. ID. No:17 (preferably to substantially the entire coding sequence thereof, i.e., nucleotides 87–1583). Especially preferred $\beta_4$-encoding DNAs of the invention are characterized as having substantially the same nucleotide sequence as set forth in SEQ. ID. No:17.

Typically, unless a $\beta_4$ subunit arises as a splice variant, $\beta_4$-encoding DNA will share substantial sequence homology (greater than about 90%) with the $\beta_4$ DNAs described or deposited herein. DNA or RNA encoding a splice variant may share less than 90% overall sequence homology with the DNA or RNA provided herein, but such DNA would include regions of nearly 100% homology to the above-described DNA.

DNA encoding human neuronal nicotinic AChR alpha and beta subunits may be isolated by screening suitable human cDNA or human genomic libraries under suitable hybridization conditions with DNA disclosed herein (including nucleotides derived from any of SEQ. ID. Nos:1, 3, 5, 7, 9, 11, 13, 15 or 17, or with any of the deposited clones referred to herein. Suitable libraries can be prepared from neuronal tissue samples, hippocampus tissue, or cell lines, such as the human neuroblastoma cell line IMR32 (ATCC Accession No. CCL127), and the like. The library is preferably screened with a portion of DNA including the entire subunit-encoding sequence thereof, or the library may be screened with a suitable probe.

As used herein, a probe is single-stranded DNA or RNA that has a sequence of nucleotides that includes at least 14 contiguous bases that are the same as (or the complement of) any 14 bases set forth in any of SEQ. ID. Nos:1, 3, 5, 7, 9, or 11, or in the subunit encoding DNA in any of the deposited clones described herein (e.g., ATCC accession no. 69239 or 69152). Preferred regions from which to construct probes include 5' and/or 3' coding sequences, sequences predicted to encode transmembrane domains, sequences predicted to encode the cytoplasmic loop, signal sequences, acetylcholine (ACh) and $\alpha$-bungarotoxin ($\alpha$-bgtx) binding sites, and the like. Amino acids 210–220 are typically involved in ACh and $\alpha$-bgtx binding. The approximate amino acid residues which comprise such regions for other preferred probes are set forth in the following table:

| Sub-unit | Signal Sequence | TMD1* | TMD2 | TMD3 | TMD4 | Cytoplasmic Loop |
|---|---|---|---|---|---|---|
| $\alpha_2$ | 1–55 | 264–289 | 297–320 | 326–350 | 444–515 | 351–443 |
| $\alpha_3$ | 1–30 | 240–265 | 273–296 | 302–326 | 459–480 | 327–458 |
| $\alpha_4$ | 1–33 | 241–269 | 275–289 | 303–330 | 593–618 | 594–617 |
| $\alpha_5$ | 1–22 | 250–275 | 282–304 | 310–335 | 422–437 | 336–421 |
| $\alpha_6$ | 1–30 | 240–265 | 272–294 | 301–326 | 458–483 | 327–457 |
| $\alpha_7$ | 1–23 | 229–256 | 262–284 | 290–317 | 462–487 | 318–461 |
| $\beta_2$ | 1–25 | 234–259 | 267–288 | 295–320 | 453–477 | 321–452 |
| $\beta_3$ | 1–20 | 232–258 | 265–287 | 293–318 | 421–446 | 319–420 |
| $\beta_4$ | 1–23 | 234–258 | 264–285 | 290–319 | 454–478 | 320–453 |

*TMD = transmembrane domain

Alternatively, portions of the DNA can be used as primers to amplify selected fragments in a particular library.

After screening the library, positive clones are identified by detecting a hybridization signal; the identified clones are characterized by restriction enzyme mapping and/or DNA sequence analysis, and then examined, by comparison with the sequences set forth herein or with the deposited clones described herein, to ascertain whether they include DNA encoding a complete alpha or beta subunit. If the selected clones are incomplete, they may be used to rescreen the same or a different library to obtain overlapping clones. If desired, the library can be rescreened with positive clones until overlapping clones that encode an entire alpha or beta subunit are obtained. If the library is a cDNA library, then the overlapping clones will include an open reading frame. If the library is genomic, then the overlapping clones may include exons and introns. In both instances, complete clones may be identified by comparison with the DNA and encoded proteins provided herein.

Complementary DNA clones encoding various subtypes of human nNAChR alpha and beta subunits have been isolated. Each subtype of the subunit appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate splice variants of human NAChR subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns that correspond to different splice variants of transcripts encoding human NAChR subunits.

It has been found that not all subunit subtypes are expressed in all neural tissues or in all portions of the brain. Thus, in order to isolate cDNA encoding particular subunit subtypes or splice variants of such subtypes, it is preferable to screen libraries prepared from different neuronal or neural tissues. Preferred libraries for obtaining DNA encoding each subunit include: hippocampus to isolate human $\alpha_4$- and $\alpha_5$-encoding DNA; IMR32 to isolate human $\alpha_3$-, $\alpha_5$-, $\alpha_7$- and $\beta_4$-encoding DNA, thalamus to isolate $\alpha_2$ and $\beta$-encoding DNA; and the like.

It appears that the distribution of expression of human neuronal nicotinic AChRs differs from the distribution of such receptors in rat. For example, RNA encoding the rat $\alpha_4$ subunit is abundant in rat thalamus, but is not abundant in rat hippocampus (see, e.g., Wada et al. (1989) J. Comp. Neurol 284:314–335). No $\alpha_4$-encoding clones could be obtained, however, from a human thalamus library. Instead, human $\alpha_4$ clones were ultimately obtained from a human hippocampus library. Thus, the distribution of $\alpha_4$ nNAChR subunit in humans and rats appears to be quite different.

Rat $\alpha_3$ subunit appears to be a CNS-associated subunit that is abundantly expressed in the thalamus and weakly expressed in the brain stem (see, e.g., Boulter et al. (1986) Nature 319:368–374; Boulter et al. (1987) Proc. Natl. Acad. Sci. USA 84:7763–7767; and Wada et al. (1989) J. Comp. Neurol 284:314–335). In efforts to clone DNA encoding the human nicotinic AChR $\alpha_3$ subunit, however, several human libraries, including a thalamus library, were unsuccessfully screened. Surprisingly, clones encoding human $\alpha_3$ subunit were ultimately obtained from a brain stem library and from IMR32 cells that reportedly express few, if any, functional nicotinic acetylcholine receptors (see, e.g., Gotti et al. ((1986) Biochem. Biophys. Res. Commun. 137:1141–1147, and Clementi et al. (1986) J. Neurochem. 47:291–297).

Rat $\alpha_7$ subunit transcript reportedly is abundantly ex-pressed in the hippocampus (see Seguela et al. (1993) J. Neurosci. 13:596–604). Efforts to clone DNA encoding a human $\alpha_7$ subunit from a human hippocampus library ($1 \times 10^6$ recombinants) were unsuccessful. Surprisingly, clones encoding a human NAChR $\alpha_7$ subunit were ultimately obtained from an IMR32 cell cDNA library.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the level of skill of the art.

An expression vector includes vectors capable of expressing DNAs that are operatively linked with regulatory sequences, such as promoter regions, that are capable of affecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention AChR subunits in eukaryotic host cells, particularly mammalian cells, include SV40 promoter-based expression vectors, such as pZeoSV (Invitrogen, San Diego, Calif.) CMV; cytomegalovirus (CMV) promoter-based vectors such as, pcDNA1, pcDNA3, pCEP4, (Invitrogen, San Diego, Calif.); and MMTV promoter-based vector such as pMAMneo (Clentech, Inc.) and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors.

Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove or alter 5' untranslated portions of the clones to remove extra, potential alternative translation initiation (i.e., start) codons or other sequences that interfere with or reduce expression, either at the level of transcription or translation. Alternatively, consensus ribosome binding sites (see, for example, Kozak (1991) J. Biol. Chem. 266:19867–19870) can be inserted immediately 5' of the start codon to enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCDNA1 (Invitrogen, San Diego, Calif.), and MMTV promoter-based vectors such as pMSG (Catalog No. 27-4506-01 from Pharmacia, Piscataway, N.J.).

Full-length DNAs encoding human neuronal NAChR subunits have been inserted into vector pCMV-T7, a pUC19-based mammalian cell expression vector containing the CMV promoter/enhancer, SV40 splice/donor sites located immediately downstream of the promoter, a polylinker downstream of the splice/donor sites, followed by an SV40 polyadenylation signal. Placement of NAChR subunit DNA between the CMV promoter and SV40 polyadenylation signal provides for constitutive expression of the foreign DNA in a mammalian host cell transfected with the construct. For inducible expression of human NAChR subunit-encoding DNA in a mammalian cell, the DNA can be inserted into a plasmid such as PMSG. This plasmid contains the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200). Full-length human DNA clones encoding human $\alpha_3$, $\alpha_4$, $\alpha_7$, $\beta_2$ and $\beta_4$ have also been subcloned into pIBI24 (International Biotechnologies, Inc., New Haven, Conn.) or pCMV-T7-2 for synthesis of in vitro transcripts.

In accordance with another embodiment of the present invention, there are provided cells containing the above-described polynucleic acids (i.e., DNA or mRNA). Such host cells as bacterial, yeast and mammalian cells can be used for replicating DNA and producing nAChR subunit(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/02311, PCT/US91/05625 and PCT/US92/11090, and in co-pending U.S. application Ser. Nos. 07/504,455, 07/563,751 and 07/812,254. The subject matter of these applications are hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subunit(s) encoded by the DNA is (are) expressed. Preferred cells include mammalian cells (e.g., HEK 293, CHO and Ltk⁻ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polymorpha*, and the like), mammalian expression systems, including commercially available systems and other such systems known to those of skill in the art, for expression of DNA encoding the human neuronal nicotinic AChR subunits provided herein are presently preferred. *Xenopus* oocytes are preferred for expression of RNA transcripts of the DNA.

In preferred embodiments, DNA is ligated into a vector, and introduced into suitable host cells to produce transformed cell lines that express a specific human nNAChR receptor subtype, or specific combinations of subtypes. The resulting cell lines can then be produced in quantity for reproducible quantitative analysis of the effects of drugs on receptor function. In other embodiments, mRNA may be produced by in vitro transcription of DNA encoding each subunit. This mRNA, either from a single subunit clone or from a combination of clones, can then be injected into *Xenopus* oocytes where the RNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Cloned full-length DNA encoding any of the subunits of human neuronal nicotinic AChR may be introduced into a plasmid vector for expression in a eukaryotic cell. Such DNA may be genomic DNA or cDNA. Host cells may be transfected with one or a combination of plasmids, each of which encodes at least one human neuronal nicotinic AChR subunit.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human neuronal nicotinic AChRs comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney cells, African green monkey cells and other such cells known to those of skill in the art), amphibian cells (e.g., *Xenopus laevis* oocytes), yeast cells (e.g., *Saccharomyces cerevisiae, Pichia pastoris*), and the like. Exemplary cells for expressing injected RNA transcripts include *Xenopus laevis* oocytes. Cells that are preferred for transfection of DNA are known to those of skill in the art or may be empirically identified, and include HEK 293 (which are available from ATCC under accession #CRL 1573; Ltk⁻ cells (which are available from ATCC under accession #CCL1.3); COS-7 cells (which are available from ATCC under accession #CRL 1651); and DG44 cells (dhrf⁻ CHO cells; see, e.g., Urlaub et al. (1986) Cell. Molec. Genet. 12:555). Presently preferred cells include DG44 cells and HEK 293 cells, particularly HEK 293 cells that have been adapted for growth in suspension and that can be frozen in liquid nitrogen and then thawed and regrown. HEK 293 cells are described, for example, in U.S. Pat. No. 5,024,939 to Gorman (see, also, Stillman et al. (1985) Mol. Cell. Biol. 5:2051–2060).

DNA may be stably incorporated into cells or may be transiently introduced using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To produce such cells, the cells should be transfected with a sufficient concentration of subunit-encoding nucleic acids to form human neuronal nicotinic AChRs that contain the human subunits encoded by heterologous DNA. The precise amounts and ratios of DNA encoding the subunits may be empirically determined and optimized for a particular combination of subunits, cells and assay conditions. Recombinant cells that express neuronal nicotinic AChR containing subunits encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human neuronal nicotinic AChR subunits may be purified using protein purification methods known to those of skill in the art. For example, antibodies or other ligands that specifically bind to one or more of the subunits may be used for affinity purification of the subunit or human neuronal nicotinic AChRs containing the subunits.

In accordance with one embodiment of the present invention, methods for producing cells that express human neuronal nicotinic AChR subunits and functional receptors are also provided. In one such method, host cells are transfected with DNA encoding at least one alpha subunit of a neuronal nicotinic acetylcholine receptor and at least one beta subunit of a neuronal nicotinic acetylcholine receptor. Using methods such as northern blot or slot blot analysis, transfected cells that contain alpha and/or beta subunit encoding DNA or RNA can be selected. Transfected cells are also analyzed to identify those that express NAChR protein. Analysis can be carried out, for example, by measuring the ability of cells to bind acetylcholine, nicotine, or a nicotine agonist, compared to the nicotine binding ability of untransfected host cells or other suitable control cells, by electrophysiologically monitoring the currents through the cell membrane in response to a nicotine agonist, and the like.

In particularly preferred aspects, eukaryotic cells which contain heterologous DNAs express such DNA and form recombinant functional neuronal nicotinic AChR(s). In more preferred aspects, recombinant neuronal nicotinic AChR activity is readily detectable because it is a type that is absent from the untransfected host cell or is of a magnitude not exhibited in the untransfected cell. Such cells that contain recombinant receptors could be prepared, for example, by causing cells transformed with DNA encoding the human neuronal nicotinic AChR $\alpha_3$ and $\beta_4$ subunits to express the corresponding proteins. The resulting synthetic or recombinant receptor would contain only the $\alpha_3$ and $\beta_4$ nNAChR subunits. Such a receptor would be useful for a variety of applications, e.g., as part of an assay system free of the interferences frequently present in prior art assay systems employing non-human receptors or human tissue preparations. Furthermore, testing of single receptor subunits with a variety of potential agonists or antagonists would provide additional information with respect to the function and activity of the individual subunits. Such information may lead to the identification of compounds which are capable of very specific interaction with one or more of the receptor subunits. Such specificity may prove of great value in medical application.

Thus, DNA encoding one or more human neuronal nicotinic AChR subunits may be introduced into suitable host cells (e.g., eukaryotic or prokaryotic cells) for expression of individual subunits and functional NAChRs. Preferably combinations of alpha and beta subunits may be introduced into cells: such combinations include combinations of any one or more of $\alpha_1$, $\alpha_2$, $\alpha_3$, $\alpha_4$, $\alpha_5$ and $\alpha_7$ with $\beta_2$ or $\beta_4$. Sequence information for $\alpha_1$ is presented in Biochem. Soc. Trans. (1989) 17:219–220; sequence information for $\alpha_5$ is presented in Proc. Natl. Acad. Sci. USA (1992) 89:1572–1576; and sequence information for $\alpha_2$, $\alpha_3$, $\alpha_4$, $\alpha_7$, $\beta_2$ and $\beta_4$ is presented in the Sequence Listing provided herewith. Presently preferred combinations of subunits include any one or more of $\alpha_1$, $\alpha_2$, $\alpha_3$ or $\alpha_5$ with $\beta_4$; or $\alpha_4$ or $\alpha_7$ in combination with either $\beta_2$ or $\beta_4$. It is recognized that some of the subunits may have ion transport function in the absence of additional subunits. For example, the $\alpha_7$ subunit is functional in the absence of any added beta subunit.

In acordance with the above, also disclosed are cells transfected or transformed with DNA or RNA encoding multimeric human NAChR subunit combinations. These include but are not limited to the following:

Multimeric Subunit Combinations $\alpha 2\beta 4\alpha 6$
$\alpha 3\beta 4\alpha 6$
$\alpha 4\beta 4\alpha 5$
$\alpha 4\beta 4\alpha 6$
$\alpha 4\beta 2\alpha 5$
$\alpha 4\beta 2\beta 3$
$\alpha 3\beta 2\alpha 6\beta 3$
$\alpha 2\beta 4\alpha 5$
$\alpha 2\beta 2\alpha 5$
$\alpha 3\beta 2\alpha 5$
$\alpha 3\beta 4\alpha 5$ Also contemplated are cells expressing one or more $\alpha$ subunit with more than one $\alpha$ subunit. These include but are not limited to the following subunit combinations:

$\alpha X\beta 2\beta 4$ (where X defines one or more of the alpha sununits disclosed herein)
$\alpha X\beta 2\beta 3\beta 4$
$\alpha 2\beta 2\alpha 6$
$\alpha 3\beta 2\alpha 6$
$\alpha 4\beta 2\alpha 6$
aXb2b3 (where X defines one or more of the alpha subunits disclosed herein)

Stable cell lines expressing any of the above referenced multimeric subunit combinations are also a feature of the invention.

As used herein, "$\beta_2$ subunit DNA" refers to DNA that encodes a neuronal subunit of the same name and, to DNA that hybridizes under conditions of high stringency to the DNA of SEQ. ID. No:9, or to the DNA of deposited clone HnACh$\beta$62, having ATCC Accession No. 68279, or to DNA encoding the amino acid sequence set forth in SEQ. ID. No:10. Typically, unless a $\beta_2$ subunit arises as a splice variant, a $\beta_2$ DNA shares substantial sequence homology (greater than about 90%) with the $\beta_2$ DNA described herein. DNA or RNA encoding a splice variant may share overall less than 90% homology with the DNA or RNA provided herein, but such a splice variant would include regions of nearly 100% homology to the above-described DNA.

In certain embodiments, eukaryotic cells with heterologous human neuronal nicotinic AChRs are produced by introducing into the cell a first composition, which contains at least one RNA transcript that is translated in the cell into a subunit of a human neuronal nicotinic AChR. In preferred embodiments, the subunits that are translated include an alpha subunit of a human neuronal nicotinic AChR. More preferably, the composition that is introduced contains an RNA transcript which encodes an alpha subunit and also contains an RNA transcript which encodes a beta subunit of a human neuronal nicotinic AChR. RNA transcripts can be obtained from cells transfected with DNAs encoding human neuronal nicotinic acetylcholine receptor subunits or by in vitro transcription of subunit-encoding DNAs. Methods for in vitro transcription of cloned DNA and injection of the resulting mRNA into eukaryotic cells are well known in the art.

Amphibian oocytes are particularly preferred for expression of in vitro transcripts of the human nNAChR DNA clones provided herein. See, for example, Dascal (1989) CRC Crit. Rev. Biochem. 22:317–387, for a review of the use of *Xenopus* oocytes to study ion channels.

Thus, pairwise (or stepwise) introduction of DNA or RNA encoding alpha and beta subtypes into cells is possible. The resulting cells may be tested by the methods provided herein or known to those of skill in the art to detect functional AChR activity. Such testing will allow the identification of pairs of alpha and beta subunit subtypes that produce functional AChRs, as well as individual subunits that produce functional AChRs.

An alternative embodiment is drawn to a non-human cell line that stably expresses the $\alpha_7$ nAChR. Preferably, the non-human cell line expressing the human $\alpha_7$ nAChR subunit is a rat cell line, i.e., the GH$_4$C$_1$ cell line.

As used herein, GH$_4$C$_1$ cells are derived from rat pituitary tumor tissue and are transfected with DNA or RNA encoding the human $\alpha_7$ nAChR.

As used herein, activity of a human neuronal nicotinic AChR refers to any activity characteristic of an NAChR. Such activity can typically be measured by one or more in vitro methods, and frequently corresponds to an in vivo activity of a human neuronal nicotinic AChR. Such activity may be measured by any method known to those of skill in the art, such as, for example, measuring the amount of current which flows through the recombinant channel in response to a stimulus.

Methods to determine the presence and/or activity of human neuronal nicotinic AChRs include assays that measure nicotine binding, $^{86}$Rb ion-flux, $Ca^{2+}$ influx, the electrophysiological response of cells, the electrophysiological response of oocytes transfected with RNA from the cells, and the like. In particular, methods are provided herein for the measurement or detection of an AChR-mediated response upon contact of cells containing the DNA or mRNA with a test compound.

As used herein, a recombinant or heterologous human neuronal nicotinic AChR refers to a receptor that contains one or more subunits encoded by heterologous DNA that has been introduced into and expressed in cells capable of expressing receptor protein. A recombinant human neuronal nicotinic AChR may also include subunits that are produced by DNA endogenous to the host cell. In certain embodiments, recombinant or heterologous human neuronal nicotinic AChR may contain only subunits that are encoded by heterologous DNA.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human neuronal nicotinic AChR subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human neuronal nicotinic AChR subunits, or may contain a mixture of subunits encoded by the host cell and subunits encoded by heterologous DNA or mRNA. Recombinant receptors may be homogeneous or may be a mixture of subtypes. Mixtures of DNA or mRNA encoding receptors from various species, such as rats and humans, may also be introduced into the cells. Thus, a cell can be prepared that expresses recombinant receptors containing only $\alpha_3$ and $\beta_4$ subunits, or any other combination of alpha and beta subunits provided herein. For example, $\alpha_4$ and/or $\alpha_7$ subunits of the present invention can be co-expressed with $\beta_2$ and/or $\beta_4$ receptor subunits; similarly, $\beta_4$ subunits according to the present invention can be co-expressed with $\alpha_2$, $\alpha_3$, $\alpha_4$, $\alpha_5$ and/or $\alpha_7$ receptor subunits. As noted previously, some of the nNAChR subunits may be capable of forming functional receptors in the absence of other subunits, thus co-expression is not always required to produce functional receptors.

As used herein, a functional neuronal nicotinic AChR is a receptor that exhibits an activity of neuronal nicotinic AChRs as assessed by any in vitro or in vivo assay disclosed herein or known to those of skill in the art. Possession of any such activity that may be assessed by any method known to those of skill in the art and provided herein is sufficient to designate a receptor as functional. Methods for detecting NAChR protein and/or activity include, for example, assays that measure nicotine binding, $^{86}$Rb ion-flux, $Ca^{2+}$ influx, the electrophysiological response of cells containing heterologous DNA or mRNA encoding one or more receptor subunit subtypes, and the like. Since all combinations of alpha and beta subunits may not form functional receptors, numerous combinations of alpha and beta subunits should be tested in order to fully characterize a particular subunit and cells which produce same. Thus, as used herein, "functional" with respect to a recombinant or heterologous human neuronal nicotinic AChR means that the receptor channel is able to provide for and regulate entry of human neuronal nicotinic AChR-permeable ions, such as, for example, $Na^+$, $K^+$, $Ca^{2+}$ or $Ba^{2+}$, in response to a stimulus and/or bind ligands with affinity for the receptor. Preferably such human neuronal nicotinic AChR activity is distinguishable, such as by electrophysiological, pharmacological and other means known to those of skill in the art, from any endogenous nicotinic AChR activity that may be produced by the host cell.

In accordance with a particular embodiment of the present invention, recombinant human neuronal nicotinic AChR-expressing mammalian cells or oocytes can be contacted with a test compound, and the modulating effect(s) thereof can then be evaluated by comparing the AChR-mediated response in the presence and absence of test compound, or by comparing the AChR-mediated response of test cells, or control cells (i.e., cells that do not express nNAChRs), to the presence of the compound.

As used herein, a compound or signal that "modulates the activity of a neuronal nicotinic AChR" refers to a compound or signal that alters the activity of NAChR so that activity of the NAChR is different in the presence of the compound or signal than in the absence of the compound or signal. In particular, such compounds or signals include agonists and antagonists. The term agonist refers to a substance or signal, such as ACh, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human neuronal nicotinic AChR activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express functional human neuronal nicotinic AChRs. In this situation, the response of test cell to test compound is compared to the response (or lack of response) of receptor-negative (control) cell to test compound, when cells or cultures of each type of cell are exposed to substantially the same reaction conditions in the presence of compound being assayed.

The functional recombinant human neuronal nicotinic AChR includes at least an alpha subunit, or an alpha subunit and a beta subunit of a human neuronal nicotinic AChR. Eukaryotic cells expressing these subunits have been prepared by injection of RNA transcripts and by transfection of DNA. Such cells have exhibited nicotinic AChR activity attributable to human neuronal nicotinic AChRs that contain one or more of the heterologous human neuronal nicotinic AChR subunits. For example, *Xenopus laevis* oocytes that had been injected with in vitro transcripts of the DNA encoding human neuronal nicotinic AChR $\alpha_3$ and $\beta_4$ subunits exhibited AChR agonist induced currents; whereas cells that had been injected with transcripts of either the $\alpha_3$ or $\beta_4$ subunit alone did not. In addition, HEK 293 cells that had been co-transfected with DNA encoding human neuronal NAChR $\alpha_3$ and $\beta_4$ subunits exhibited AChR agonist-induced increases in intracellular calcium concentration, whereas control HEK 293 cells (i.e., cells that had not been transfected with $\alpha_3$- and $\beta_4$-encoding DNA) did not exhibit any AChR agonist-induced increases in intracellular calcium concentration.

With respect to measurement of the activity of functional heterologous human neuronal nicotinic AChRs, endogenous AChR activity and, if desired, activity of AChRs that contain a mixture of endogenous host cell subunits and heterologous subunits, should, if possible, be inhibited to a significant extent by chemical, pharmacological and electrophysiological means.

Deposits

The deposited clones have been deposited at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. Patent based on this or any application claiming priority to or incorporating this application by reference thereto, all restrictions upon availability of the deposited material will be irrevocably removed.

The invention will now be described in greater detail with reference to the following non-limiting examples.

EXAMPLE 1

Isolation of DNA Encoding Human nNAChR Subunits

A. DNA Encoding a Human nNAChR $\beta_4$ Subunit

Random primers were used in synthesizing cDNA from RNA isolated from the IMR32 human neuroblastoma cell line (the cells had been treated with dibutyryl cAMP and bromodeoxyuridine prior to constructing the library). The library constructed from the cDNAs was screened with a fragment of a rat nicotinic AChR $\beta_4$ subunit cDNA. Hybridization was performed at 42° C. in 5×SSPE, 5× Denhardt's solution, 50% formamide, 200 µg/ml herring sperm DNA and 0.2% SDS. Washes were performed in 0.1×SSPE, 0.2% SDS at 65° C. Five clones were identified that hybridized to the probe.

The five clones were plaque-purified and characterized by restriction enzyme mapping and DNA sequence analysis. The insert DNA of one of the five clones contained the complete coding sequence of a $\beta_4$ subunit of a human nicotinic AChR (see nucleotides 87–1583 of SEQ. ID. No:11). The amino acid sequence deduced from the nucleotide sequence of the full-length clone has ~81% identity with the amino acid sequence deduced from the rat nicotinic AChR $\beta_4$ subunit DNA. Several regions of the deduced rat and human $\beta_4$ amino acid sequences are notably dissimilar: amino acids 1–23 (the human sequence has only ~36% identity with respect to the rat sequence), 352–416 (the human sequence has only ~48% identity with respect to the rat sequence), and 417–492 (the human sequence has only ~78% identity with respect to the rat sequence). Furthermore, amino acids 376–379 in the rat $\beta_4$ subunit are not contained in the human $\beta_4$ subunit.

B. DNA Encoding a Human nNAChR $\alpha_7$ Subunit

An amplified IMR32 cell cDNA library (1×10$^6$ recombinants; cells treated with dibutyryl cAMP and bromodeoxyuridine) was screened with a fragment of a rat nicotinic AChR $\alpha_7$ subunit cDNA. The hybridization conditions were identical to those described above for screening an IMR32 cell cDNA library with the rat $\beta_4$ subunit DNA. Washes were performed in 0.2×SSPE, 0.2% SDS at 65° C. Seven positive clones were identified by hybridization to the labeled rat DNA probe. Six of the clones were plaque-purified and characterized by restriction enzyme mapping and DNA sequence analysis. One of the clones contains the complete coding sequence of a human AChR receptor $\alpha_7$ subunit gene (see nucleotides 73–1581 of SEQ. ID. No:7).

C. DNA Encoding a Human nNAChR $\alpha_4$ Subunit

Random primers were used in synthesizing cDNA from RNA isolated from human hippocampus tissue. cDNAs larger than 2.0 kb were inserted into the λgt10 phage vector to create a cDNA library. Approximately 1×10$^6$ recombinants were screened with a fragment of a DNA encoding a rat nicotinic AChR $\alpha_4$ subunit using the same hybridization and washing conditions as described above for screening an IMR32 cell cDNA library for $\alpha_7$ subunit cDNAs. Three clones hybridized strongly to the probe. Two of these three clones, designated KE$\alpha$4.1 and KE$\alpha$4.2, have been deposited with the American Type Culture Collection (ATCC, Rockville, Md.) and assigned accession nos. 69152 and 69239, respectively.

Characterization of the plaque-purified clones revealed that one of the clones, KE$\alpha$4.2, contains the complete coding sequence of a human nicotinic AChR $\alpha$4 subunit gene (coding sequence of this human $\alpha_4$ subunit cDNA is provided as nucleotides 184–2067 in SEQ. ID. No:5). Comparison of the 5' ends of the coding sequences of the human and rat $\alpha$4 subunit cDNAs reveals that the rat sequence contains an 18-nucleotide segment that is not present in the human sequence.

D. DNA Encoding Human nNAChR $\alpha_2$, $\alpha_3$, & $\beta_2$ Subunits

Plasmids containing DNA that encodes and/or that can be used to isolate DNA that encodes human neuronal nicotinic acetylcholine receptor $\alpha_2$, $\alpha_3$ and $\beta_2$ subunits have been deposited with the American Type Culture Collection (ATCC). The clone names and deposit accession numbers are:

| Subunit | Clone Name | ATCC Accession No. |
|---------|------------|--------------------|
| $\alpha_2$ | HnAChR$\alpha$2 | 68277 |
| $\alpha_3$ | HnACHR$\alpha$3 | 68278 |
| $\beta_2$ | HnAChR$\beta$2 | 68279 |

In addition, DNA sequences that encode full-length $\alpha_2$, $\alpha_3$ and $\beta_2$ subunits are set forth in SEQ. ID. Nos:1, 3 and 9, respectively.

EXAMPLE 2

I. Preparation of Constructs for the Expression of Recombinant Human Neuronal Nicotinic AChR Subunits Isolated cDNAs encoding human neuronal nicotinic AChR subunits were incorporated into vectors for use in expressing the subunits in mammalian host cells and for use in generating in vitro transcripts of the DNAs to be expressed in *Xenopus* oocytes. Several different vectors were utilized in preparing the constructs as follows.

A. Construct for Expression of a Human nNAChR $\alpha_3$ Subunit

Figure 1A:
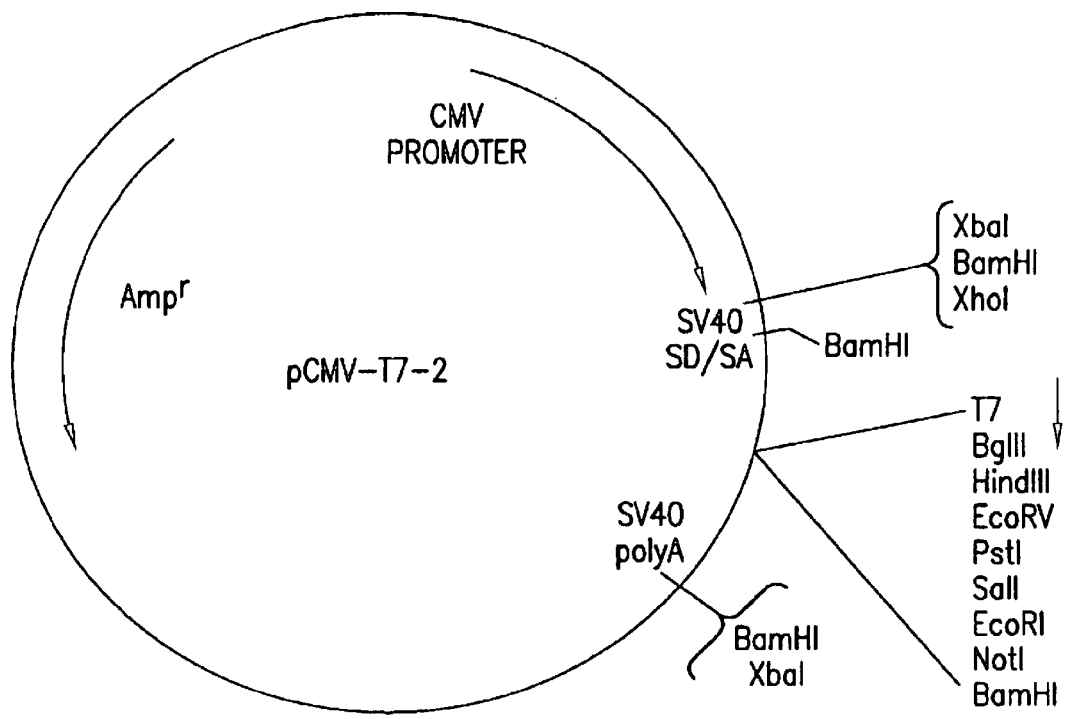
Figure 1B:
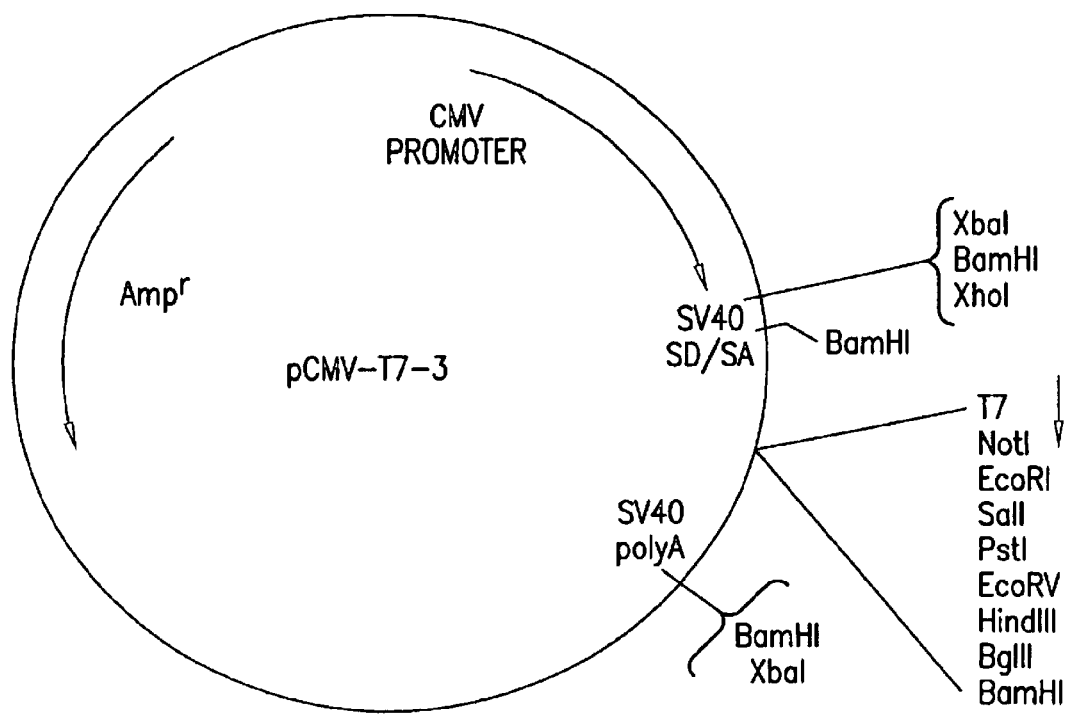
Figure 2:
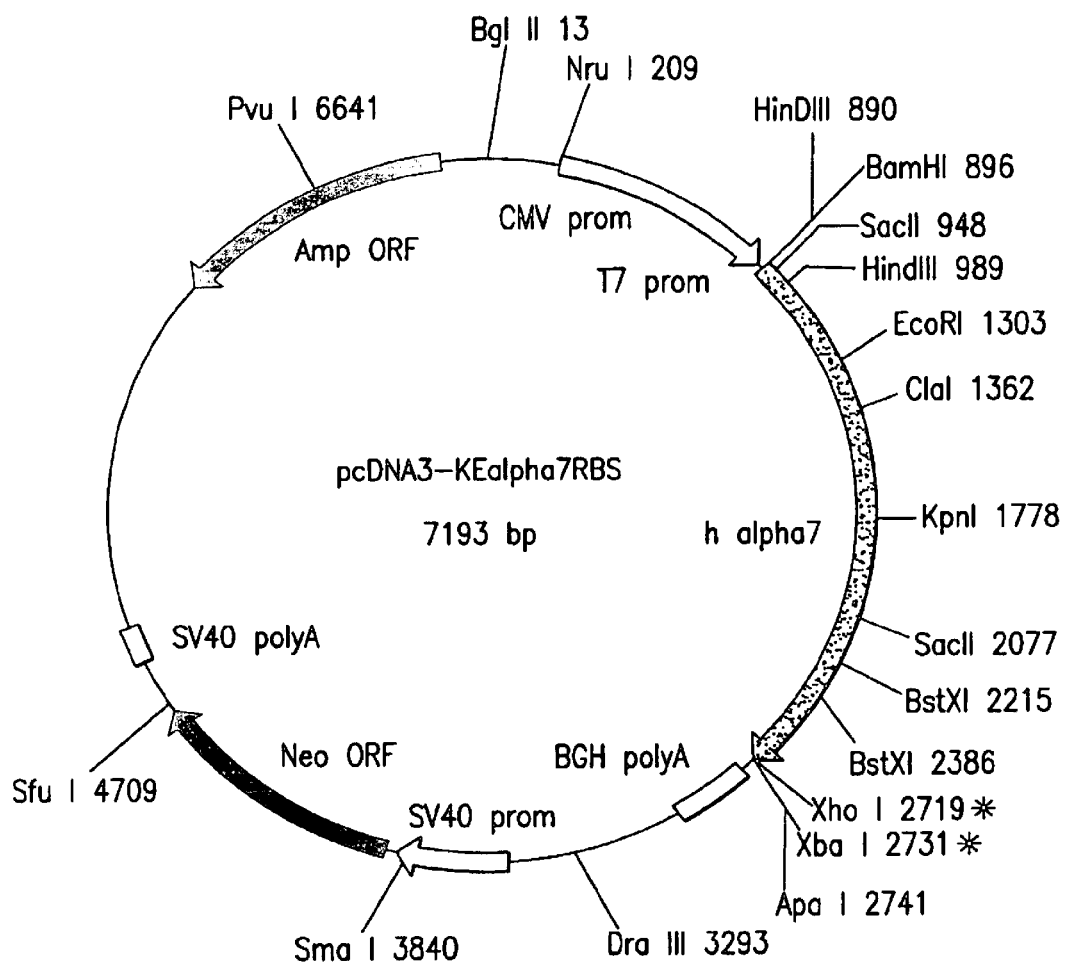

DNA encoding a human neuronal nicotinic AChR $\alpha_3$ subunit was subcloned into the pCMV-T7-2 general expression vector to create pCMV-KE$\alpha$3. Plasmid pCMV-T7-2 (see FIG. 1) is a pUC19-based vector that contains a CMV promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. FIG. 1 also shows a restriction map of pCMV-T7-3. This plasmid is identical to pCMV-T7-2 except that the restriction sites in the polylinker are in the opposite order as compared to the order in which they occur in pCMV-T7-2.

A 1.7 kb SfiI (blunt-ended)/EcoRI DNA fragment containing nucleotides 27–1759 of SEQ. ID. No:3 (i.e., the entire $\alpha_3$ subunit coding sequence plus 12 nucleotides of 5' untranslated sequence and 206 nucleotides of 3' untranslated sequence) was ligated to EcoRV/EcoRI-digested pCMV-T7-2 to generate pCMV-KE$\alpha$3. Plasmid pCMV-KE$\alpha$3 was used for expression of the $\alpha_3$ subunit in mammalian cells and for generating in vitro transcripts of the $\alpha_3$ subunit DNA.

B. Constructs for Expression of a Human nNAChR $\beta_4$ Subunit

A 1.9 kb EcoRI DNA fragment containing nucleotides 1–1915 of SEQ. ID. No:11 (i.e., the entire $\beta_4$ subunit coding sequence plus 86 nucleotides of 5' untranslated sequence and 332 nucleotides of 3' untranslated sequence) was ligated to EcoRI-digested pGEM7Zf(+) (Promega Catalog #P2251; Madison, Wis.). The resulting construct, KE$\beta$4.6/pGEM, contains the T7 bacteriophage RNA polymerase promoter in operative association with two tandem $\beta_4$ subunit DNA inserts (in the same orientation) and was used in generating in vitro transcripts of the DNA.

The same 1.9 kb EcoRI DNA fragment containing nucleotides 1–1915 of SEQ. ID. No:11 was ligated as a single insert to EcoRI-digested pCMV-T7-3 to generate pCMV-KE$\beta$4. Plasmid pCMV-KE$\beta_4$ was used for expression of the $\beta_4$ subunit in mammalian cells and for generating in vitro transcripts of the $\beta_4$ subunit DNA.

C. Constructs for Expression of a Human nNAChR $\alpha_7$ Subunit

Two pCMV-T7-2-based constructs were prepared for use in recombinant expression of a human neuronal nicotinic AChR $\alpha_7$ subunit. The first construct, pCMV-KE$\alpha$7.3, was prepared by ligating a 1.9 kb XhoI DNA fragment containing nucleotides 1–1876 of SEQ. ID. No:7 (i.e., the entire $\alpha_7$ subunit coding sequence plus 72 nucleotides of 5' untranslated sequence and 295 nucleotides of 3' untranslated sequence) to SalI-digested pCMV-T7-3. The second construct, pCMV-KE$\alpha$7, was prepared by replacing the 5' untranslated sequence of the 1.9 kb XhoI $\alpha_7$ subunit DNA fragment described above with a consensus ribosome binding site (5'-GCCACC-3'; see Kozak (1987) Nucl. Acids Res. 15:8125–8148). The resulting modified fragment was ligated as a 1.8 kb BglII/XhoI fragment with BglII/SalI-digested pCMV-T7-2 to generate pCMV-KE$\alpha$7. Thus, in pCMV-KE$\alpha$7, the translation initiation codon of the coding sequence of the $\alpha_7$ subunit cDNA is preceded immediately by a consensus ribosome binding site.

D. Constructs for Expression of a Human nNAChR $\beta_2$ Subunit

DNA fragments encoding portions of a human neuronal nicotinic AChR $\beta_2$ subunit were ligated together to generate a full-length $\beta_2$ subunit coding sequence contained in plasmid pIBI124 (International Biotechnologies, Inc. (IBI), New Haven, Conn.). The resulting construct, H$\beta$2.1F, contains nucleotides 1–2450 of SEQ. ID. No:9 (i.e., the entire $\beta_2$ subunit coding sequence, plus 266 nucleotides of 5' untranslated sequence and 675 nucleotides of 3' untranslated sequence) in operative association with the T7 promoter. Therefore, H$\beta$2.1F was used for synthesis of in vitro transcripts from the $\beta_2$ subunit DNA.

Since the 5' untranslated sequence of the $\beta_2$ subunit DNA contains a potential alternative translation initiation codon (ATG) beginning 11 nucleotides upstream (nucleotides 256–258 in SEQ. ID. No:9) of the correct translation initiation codon (nucleotides 267–269 in SEQ. ID. No:9), and because the use of the upstream ATG sequence to initiate translation of the $\beta_2$ DNA would result in the generation of an inoperative peptide (because the upstream ATG is not in the correct reading frame), an additional $\beta_2$-encoding construct was prepared as follows. A 2.2 kb KspI/EcoRI DNA fragment containing nucleotides 262–2450 of SEQ. ID. No:9 was ligated to pCMV-T7-2 in operative association with the T7 promoter of the plasmid to create pCMV-KE$\beta$2. The $\beta_2$ subunit DNA contained in pCMV-KE$\beta$2 retains only 5 nucleotides of 5' untranslated sequence upstream of the correct translation initiation codon.

EXAMPLE 3

Expression of Recombinant Human Nicotinic AChR in Oocytes

*Xenopus* oocytes were injected with in vitro transcripts prepared from constructs containing DNA encoding $\alpha_3$, $\alpha_7$, $\beta_2$ and $\beta_4$ subunits. Electrophysiological measurements of the oocyte transmembrane currents were made using the two-electrode voltage clamp technique (see, e.g., Stuhmer (1992) *Meth. Enzymol.* 207:319–339).

1. Preparation of in vitro Transcripts

Recombinant capped transcripts of pCMV-KE$\alpha$3, pCMV-KE$\beta$2, KE$\beta$4.6/pGEM and pCMV-KE$\beta$4 were synthesized from linearized plasmids using the mCAP RNA Capping Kit (Cat. #200350 from Stratagene, Inc., La Jolla, Calif.). Recombinant capped transcripts of pCMV-KE$\alpha$7, pCMV-KE$\alpha$7.3 and H$\beta$2.1F were synthesized from linearized plasmids using the MEGAscript T7 in vitro transcription kit according to the capped transcript protocol provided by the manufacturer (Catalog #1334 from AMBION, Inc., Austin, Tex.). The mass of each synthesized transcript was determined by UV absorbance and the integrity of each transcript was determined by electrophoresis through an agarose gel.

2. Electrophysiology

*Xenopus* oocytes were injected with either 12.5, 50 or 125 ng of human nicotinic AChR subunit transcript per oocyte. The preparation and injection of oocytes were carried out as described by Dascal (1987) in *Crit. Rev. Biochem.* 22:317–387. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 mM HEPES, pH 7.3) containing 1 $\mu$M atropine with or without 100 $\mu$M d-tubocurarine. Cells were voltage-clamped at −60 to −80 mV. Data were acquired with Axotape software at 2–5 Hz. The agonists acetylcholine (ACh), nicotine, and cytisine were added at concentrations ranging from 0.1 $\mu$M to 100 $\mu$M. The results of electrophysiological analyses of the oocytes are summarized in Table 1.

TABLE 1

| Template, ng RNA Injected | Number of oocytes responding | Current Agonists | Amplitude |
|---|---|---|---|
| pCMV-KEα3, 12.5 ng | 0 of 8 | ACh, Nicotine | |
| KEβ4.6/pGEM, 12.5 ng | 0 of 9 | ACh, Nicotine | |
| pCMV-KEα3, 12.5 ng + KEβ4.6/pGEM, 12.5 ng | 4 of 5 | ACh, Nicotine | 20–550 nA |
| pCMV-KEα3, 12.5 ng + KEβ4.6/pGEM, 12.5 ng | 3 of 4 | ACh, Cytisine, Nicotine | 20–300 nA |
| pCMV-KEα3, 125 ng + and pCMV-KEβ4, 125 ng | 5 of 5 | Ch, Nicotine, Cytisine | 200–500 nA |
| pCMV-KEα3, 125 ng + pCMV-KEβ4, 125 ng | 6 of 6 | ACh, Nicotine, Cytisine | 100–400 nA |
| pCMV-KEα7.3, 125 ng | 3 of 15 | Ach | ~20 nA |
| pCMV-KEα7, 125 ng | 11 of 11 | Ach | 20–250 nA |
| pCMV-KEα3, 12.5 ng + pCMV-KEβ2, 12.5 ng | 2 of 9 | ACh, Nicotine | <10 nA |
| pCMV-KEα3, 125 ng + pCMV-KEβ2, 125 ng | 0 of 9 | ACh, Nicotine | |
| pCMV-KEα3, 125 ng + Hβ2.1 F, 125 ng | 13 of 16 | Ach (100 $\mu$M) ACh (300 $\mu$M) | ~20 nA ~80 nA | a. Oocytes Injected with $\alpha_3$ and/or $\beta_4$ Transcripts

Oocytes that had been injected with 12.5 ng of the $\alpha_3$ transcript or 12.5 ng of the $\beta_4$ transcript did not respond to application of up to 100 $\mu$M ACh, nicotine or cytisine. Thus, it appears that these subunits do not form functional homomeric nicotinic AChR channels. By contrast, oocytes injected with 12.5 or 125 ng of the $\alpha_3$ transcript and 12.5 ng or 125 ng of the $\beta_4$ transcript exhibited detectable inward currents in response to ACh, nicotine, and cytisine at the tested concentrations (0.1 $\mu$M to 10 $\mu$M). Some differences in the kinetics of the responses to cytisine compared to nicotine and ACh were observed. The relative potency of the agonists appeared to be cytisine>ACh>nicotine, which differs from the results of similar studies of oocytes injected with transcripts of the rat nicotinic AChR $\alpha_3$ and $\beta_4$ subunits (see, for example, Luetje et al. (1991) *J. Neurosci.* 11:837–845).

The responses to ACh and nicotine were reproducibly blocked by d-tubocurarine. For example, complete blockage of the response to ACh was observed in the presence of 100 $\mu$M d-tubocurarine. The inhibition appeared to be reversible. The responses to ACh, nicotine and cytisine were also at least partially blocked by 100 nM mecamylamine.

The current response of $\alpha_3$-$\beta_4$-injected oocytes to 10 $\mu$M ACh was also examined in terms of membrane voltage. In these experiments, voltage steps were applied to the cells in the presence of ACh. The graph of current vs. voltage appeared typical of responses observed for $Na^+$, $K^+$-permeable channels. For example, the zero current level (reversal potential) is less than −40 mV. The contribution of $Ca^{++}$ flux to the total current can be ascertained by varying the calcium concentration in the external medium and taking multiple current measurements at different holding potentials around the reversal potential. Such studies indicate that the channel carrying the current generated in response to ACh treatment of $\alpha_3$-$\beta_4$-injected oocytes is permeable to $Na^+$, $K^+$ and $Ca^{++}$.

b. Oocytes Injected with $\alpha_7$ Subunit Transcripts

As described in Example 2, two constructs were prepared for use in expressing the human neuronal nicotinic AChR $\alpha_7$ subunit. Plasmid pCMV-KEα7.3 contains the $\alpha_7$ subunit coding sequence with 72 nucleotides of 5' untranslated sequence upstream of the translation initiation codon. Plasmid pCMV-KEα7 contains the $\alpha_7$ subunit coding sequence devoid of any 5' untranslated sequence and further contains a consensus ribosome binding site immediately upstream of the coding sequence.

Oocytes injected with 125 ng of $\alpha_7$ transcript synthesized from pCMV-KEα7 displayed inward currents in response to 10 or 100 $\mu$M ACh. This response was blocked by 100 $\mu$M d-tubocurarine.

Oocytes injected with 125 ng of $\alpha_7$ transcript synthesized from pCMV-KEα7.3 exhibited ACh-induced currents that were substantially weaker than those of oocytes injected with $\alpha_7$ transcript synthesized from pCMV-KEα7. These results indicate that human neuronal nicotinic AChR $\alpha_7$ subunit transcripts generated from $\alpha_7$ subunit DNA containing a ribosome binding site in place of 5' untranslated sequence may be preferable for expression of the $\alpha_7$ receptor in oocytes.

c. Oocytes Injected with $\beta_3$ and $\beta_2$ Subunit Transcripts

As described in Example 2, two constructs were prepared for use in expressing the human neuronal nicotinic AChR $\beta_2$ subunit. Plasmid Hβ2.1F contains the $\beta_2$ subunit coding sequence with 266 nucleotides of 5' untranslated sequence upstream of the translation initiation codon. Plasmid pCMV-KEβ2 contains the $\beta_2$ subunit coding sequence and only 5 nucleotides of 5' untranslated sequence upstream of the translation initiation codon.

Oocytes injected with transcripts of pCMV-KEα3 and pCMV-KEβ2 displayed no current in response to nicotinic AChR $\alpha_3$ agonists. In contrast, oocytes injected with transcripts of pCMV-KEα3 and Hβ2.1F displayed ~20 nA inward currents in response to 100 $\mu$M ACh and ~80 nA inward currents in response to 300 $\mu$M ACh. The current response was blocked by 100 $\mu$M d-tubocurarine. These results indicate that human neuronal nicotinic AChR $\beta_2$ subunit transcripts generated from $\beta_2$ subunit DNA containing 5' untranslated sequence may be preferable to transcripts generated from $\beta_2$ DNA containing only a small portion of 5' untranslated sequence for expression of the $\alpha_3\beta_2$ receptors in oocytes.

EXAMPLE 4

Recombinant Expression of Human nNAChR Subunits in Mammalian Cells

1. Recombinant Expression of Human NAChR $\alpha_3$ and $\beta_4$ or $\alpha_7$ Subunits in HEK 293 Cells:

Human embryonic kidney (HEK) 293 cells were transiently and stably transfected with DNA encoding human neuronal nicotinic AChR $\alpha_3$ and $\beta_4$, or $\alpha_7$ subunits. Transient transfectants were analyzed for expression of nicotinic AChR using various assays, e.g., electrophysiological methods, $Ca^{2+}$-sensitive fluorescent indicator-based assays and [$^{125}$I]-$\alpha$-bungarotoxin-binding assays.

1. Transient Transfection of HEK Cells

Two transient transfection were performed. In one transfection, HEK cells were transiently co-transfected with DNA encoding $\alpha_3$ (plasmid pCMV-KE$\alpha$3) and $\beta_4$ (plasmid pCMV-KF$\beta$4) subunits. In the other transfection, HEK cells were transiently transfected with DNA encoding the $\alpha_7$ subunit (plasmid pCMV-KE$\alpha$7). In both transfections, ~2×10$^6$ HEK cells were transiently transfected with 18 $\mu$g of the indicated plasmid(s) according to standard CaPO$_4$ transfection procedures [Wigler et al. (1979) *Proc. Natl. Acad. Sci. U.S.A.* 76:1373–1376]. In addition, 2 $\mu$g of plasmid pCMV$\beta$gal (Clontech Laboratories, Palo Alto, Calif.), which contains the *Escherichia coli* $\beta$-galactosidase gene fused to the CMV promoter, were co-transfected as a reporter gene for monitoring the efficiency of transfection. The transfectants were analyzed for $\beta$-galactosidase expression by measurement of $\beta$-galactosidase activity [Miller (1972) Experiments in Molecular Genetics, pp. 352–355, Cold Spring Harbor Press]. Transfectants can also be analyzed for $\beta$-galactosidase expression by direct staining of the product of a reaction involving $\beta$-galactosidase and the X-gal substrate [Jones (1986) *EMBO* 5:3133–3142].

The efficiency of transfection of HEK cells with pCMV-KE$\alpha$ 3/pCMV-KE$\beta$4 was typical of standard efficiencies, whereas the efficiency of transfection of HEK cells with pCMV-KE$\alpha$7 was below standard levels.

2. Stable Transfection of HEK Cells

HEK cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEK cells were transfected with 1 ml of DNA/calcium phosphate precipitate containing 9.5 $\mu$g pCMV-KE$\alpha$3, 9.5 $\mu$g pCMV-KE$\beta$4 and 1 $\mu$g pSV2neo (as a selectable marker). After 14 days of growth in media containing 1 $\mu$g/ml G418, colonies had formed and were individually isolated by using cloning cylinders. The isolates were subjected to limiting dilution and screened to identify those that expressed the highest level of nicotinic AChR, as described below.

3. Analysis of Transfectants a. Fluorescent Indicator-based Assays

Activation of the ligand-gated nicotinic AChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator, therefore, an increase in the intracellular $Ca^{2+}$ concentration of cells containing the indicator can be expressed directly as an increase in fluorescence. An automated fluorescence detection system for assaying icotinic AChR has been described in commonly assigned pending U.S. patent application Ser. No. 07/812,254 and corresponding PCT Patent Application No. US92/11090.

HEK cells that were transiently or stably co-transfected with DNA encoding $\alpha$3 and $\beta$4 subunits were analyzed for expression of functional recombinant nicotinic AChR using the automated fluorescent indicator-based assay. The assay procedure was as follows.

Untransfected HEK cells (or HEK cells transfected with pCMV-T7-2) and HEK cells that had been co-transfected with pCMV-KE$\alpha$3 and pCMV-KE$\beta$4 were plated in the wells of a 96-well microtiter dish and loaded with fluo-3 by incubation for 2 hours at 20° C. in a medium containing 20 $\mu$M fluo-3, 0.2% Pluronic F-127 in HBS (125 mM NaCl, 5 mM KCl, 1.8 mM CaCl$_{2, 0.62}$ mM MgSO$_4$, 6 mM glucose, 20 mM HEPES, pH 7.4). The cells were then washed with assay buffer (i.e., HBS). The antagonist d-tubocurarine was added to some of the wells at a final concentration of 10 $\mu$M. The microtiter dish was then placed into a fluorescence plate reader and the basal fluorescence of each well was measured and recorded before addition of 200 $\mu$M nicotine to the wells. The fluorescence of the wells was monitored repeatedly during a period of approximately 60 seconds following addition of nicotine.

The fluorescence of the untransfected HEK cells (or HEK cells transfected with pCMV-T7-2) did not change after addition of nicotine. In contrast, the fluorescence of the co-transfected cells, in the absence of d-tubocurarine, increased dramatically after addition of nicotine to the wells. This nicotine-stimulated increase in fluorescence was not observed in co-transfected cells that had been exposed to the antagonist d-tubocurarine. These results demonstrate that the co-transfected cells express functional recombinant AChR that are activated by nicotine and blocked by d-tubocurarine.

b. $\alpha$-Bungarotoxin Binding Assays

HEK293 cells transiently transfected with pCMV-KE$\alpha$7 were analyzed for [$^{125}$I]-$\alpha$-bungarotoxin (BgTx) binding. Both whole transfected cells and membranes prepared from transfected cells were examined in these assays. Rat brain membranes were included in the assays as a positive control.

Rat brain membranes were prepared according to the method of Hampson et al. (1987) *J. Neurochem* 49:1209. Membranes were prepared from the HEK cells transfected with pCMV-KE$\alpha$7 and HEK cells transiently transfected with plasmid pUC19 only (negative control) according to the method of Perez-Reyes et al. (1989) *Nature* 340:233. Whole transfected and negative control cells were obtained by spraying the tissue culture plates with phosphate-buffered saline containing 0.1% (w/v) BSA. The cells were then centrifuged at low speed, washed once, resuspended in assay buffer (118 mM NaCl, 4.8 mM KCl, 2.5 mM CaCl$_2$, 1.2 mM MgSO$_4$, 20 mM HEPES, 0.1% (w/v)BSA, 0.05% (w/v) bacitracin and 0.5 mM PMSF, pH 7.5) and counted.

Specific binding of [$^{125}$I]-$\alpha$-BgTx to rat brain membranes was determined essentially as described by Marks et al. (1982) *Molec. Pharmacol.* 22:554–564, with several modifications. The membranes were washed twice in assay buffer. The assay was carried out in 12×75 mm polypropylene test tubes in a total volume of 0.5 ml assay buffer. The membranes were incubated with 10 nM [$^{125}$I]-$\alpha$-BgTx (New England Nuclear, Boston, Mass.) for one hour at 37° C. The assay mixtures were then centrifuged at 2300×g for 10 minutes at 4×C. The supernatant was decanted and the pellets were washed twice with 2 ml aliquots of ice-cold assay buffer. The supernatants were decanted again and the radioactivity of the pellets was measured in a γ-counter. Non-specific binding was determined in the presence of 1 µM unlabeled α-BgTx. Specific binding was determined by subtracting nonspecific binding from total binding. Specific binding of [$^{125}$I]-α-BgTx to membranes prepared from transfected and negative control cells was determined as described for determining specific binding to rat brain membranes except that the assay buffer did not contain BSA, bacitracin and PMSF. Specific binding of [$^{125}$I]-α-BgTx to transfected and negative control whole cells was determined basically as described for determining specific binding to rat brain membranes.

[$^{125}$I]-α-BgTx binding was evaluated as a function of membrane concentration and as a function of incubation time. [$^{125}$I]-α-BgTx binding to rat brain membranes increased in a linear fashion with increasing amounts of membrane (ranging between 25–500 µg). The overall signal-to-noise ratio of binding (i.e., ratio of total binding to non-specific binding) was 3:1. Although some binding of [$^{125}$I]-α-BgTx to transfected cell membranes was detected, it was mostly non-specific binding and did not increase with increasing amounts of membrane. [$^{125}$I]-α-BgTx binding to the transfectants and negative control cells appeared to be similar.

To monitor [$^{125}$I]-α-BgTx binding to rat brain membranes and whole transfected and negative control cells, 300 µg of membrane or 500,000 cells were incubated with 1 nM or 10 nM [$^{125}$I]-α-BgTx, respectively, at 37° C. for various times ranging from 0–350 min. Aliquots of assay mixture were transferred to 1.5 ml microfuge tubes at various times and centrifuged. The pellets were washed twice with assay buffer. [$^{125}$I]-α-BgTx binding to rat brain membranes increased with time and was maximal after three hours. The binding profiles of the transfected and negative control cells were the same and differed from that of rat brain membranes.

Recombinant Expression of Human nAChR Subunits (Multimeric Subunit Combinations) in Mammalian Cells II. (a) Preparation of Constructs for the Expression of Recombinant Human Neuronal Nicotinic nAChR Containing Multimeric Subunits.

Isolated cDNAs encoding human neuronal nAChRs were incorporated into vectors for use in expressing the subunits in mammalian host cells.

A. Construct for Expression of a Human nAChR α3 Subunit.

Construct pCMV-KEα3 (FIG. 12) is described in U.S. Pat. No. 5,837,489, the contents of which are incorporated by reference herein in ther entirety, was digested with HindIII and NotI to release a 1.7 kb DNA fragment containing the entire α3 coding region. The expression construct pcDNA3-KEα3 was prepared by ligating the 1.7 kb α3 DNA fragment from pCMV-KEα3 into vector HindIII and NotI digested pcDNA3 (Invitrogen).

B. Construct for Expression of a Human nAChR α5 Subunit.

DNA fragments encoding portions of a human nAChR $α_5$ subunit were ligated together to generate a full-length α5 subunit coding sequence contained in plasmid pcDNA1/Amp-KEα5.5F. This construct was modified by replacing the 5' untranslated sequence of the α5 subunit DNA with a consensus ribosome binding site, RBS, (5'-GCCACC-3', see Kozak (1987) Nucl. Acids Res. 15:8225–8148) to generate pcDNA1/Amp-KEα5RBS). Construct pcDNA1/Amp-KEα5RBS was digested with BamHI and EcoRI to release a 1.7 kb DNA fragment containing the consensus ribosome binding site immediately 5' to the translation initiation codon of α5 and also containing the entire α5 coding region. Construct pcDNA3-KEα5RBS was prepared by digestion of pcDNA3 with BamHI and EcoRI followed by ligation of the 1.7 kb α5 DNA fragment. The pcDNA3-KEα5RBS construct was then digested with Asp718I and BstX1 to release a 1.7 kb fragment containing the entire α 5 coding sequence with the RBS immediately 5' to the α5 sequence. This fragment was ligated into expression vector pHOOK3 (Invitrogen) which had been digested with Asp718I and BstXI to generate the expression construct pHOOK3-KEα5RBS (FIG. 13).

C. Construct for Expression of a Human nAChR β2 Subunit.

Construct pCMV-KEβ2 (described in U.S. Pat. No. 5,910,582) was modified by replacing the 5' untranslated sequence of the β2 subunit DNA with a consensus ribosome binding site (5'-GCCACC-3', see Kozak (1987) Nucl. Acids Res. 15:8225–8148) to generate pCMV-KEβ2RBS. The expression vector pCMV-KEβ2RBS was digested with BglII and EcoRI to release a 2.2 kb DNA fragment containing the consensus ribosome binding site immediately 5' to the translation initiation codon of β2 and also containing the entire β2 coding region. This 2.2 kb DNA fragment was ligated into expression vector pcDNA3 that had been digested with BamHI and EcoRI. The BamHI site is compatible with BglII and this ligation generated expression construct pcDNA3-KEβ2RBS (FIG. 14).

II (b) Recombinant Expression of the Human α3β2α5 nAChR in HEK293 Cells.

Human embryonic kidney cells (HEK 293) were stably co-transfected with DNA encoding human neuronal nAChR α3, β2 and α5 and analyzed for expression of nAChRs using various assays, for example, calcium sensitive fluorescent indicator-based assays and electrophysiological methods.

1. Stable Co-transfection of HEK293 Cells with Human α3, β2 and α5 nAChRs.

a. Expression Strategy.

The α 5 nAChR is non-functional when expressed with either another α subunit or another β subunit. In order to develop a functional 3-way nAChR that includes the α5 subunit, α5 was co-expressed with both α3 and β2. The antibiotic selection strategy was designed to take advantage of the lack of function of co-expression of either α3α5 or α5β2. Even though these combinations would survive the antibiotic selection, they would be non-functional. Using this expression strategy, the only possible nAChR subunit combination surviving antibiotic selection and having functional responses would be α3β2α5. The expression strategy for the generation of this subunit combination is described in detail below.

The α3 was cloned into pcDNA3 (Invitrogen) that encodes a neomycin resistance gene permitting tolerance to the antibiotic G418. The β2 subunit was also cloned into pcDNA3. The α5 subunit was cloned into the expression vector pHOOK3 (Invitrogen) which encodes the Zeocin™ (Invitrogen) resistance gene that allows tolerance to the antibiotic Zeocin™. By this strategy, cells stably expressing the α5 nAChR and α3 or α5 and β2 could survive in a selection culture medium containing both G418 and Zeocin™. However, stable expression of α3, α5 and β2 would be required for function.

b. Recombinant Expression of Human α3β2α5 nAChRs.

HEK293 cells were stably co-transfected with DNA encoding human neuronal nAChRs α3, β2 and α5 using the lipofection transfection procedure (Current Protocols in Molecular Biology, Volume 1, 9.4.1–9.4.5 and 9.5.1–9.5.6, the contents of which are incorporated by reference herein). HEK293 cells were harvested and plated onto 10 cm tissue culture plates that were coated with poly-D-lysine. The HEK293 cells were plated at a concentration of 1.2 million cells per plate, 24 hours prior to transfection. Two micrograms of DNA encoding α3 (mammalian expression vector pcDNA3-KEα3), 2 μg of DNA encoding β2 (pcDNA3-KEβ2RBS) and 2 μg of DNA encoding α5 (pHOOK3-KEα5RBS) were diluted in 300 μl of Dulbecco's Modified Eagle Medium (DMEM) and combined with 20 μl of LipofectAMINE™ Reagent (Gibco-BRL) for 15 minutes. The HEK293 cells were washed twice with DMEM. This DNA/LipofectAMINE mixture was further diluted into 5.3 ml of DMEM and overlaid onto the HEK293 cells. The overlaid cells were incubated for 5 hours in an incubator at 37° C., in a humidified atmosphere containing 5% carbon dioxide. Cell plates were washed twice with 5 mls of complete media (DMEM, 6% iron-supplemented calf serum, 2 mM glutamine, 100 units per ml of penicillin and 100 μg/ml streptomycin) then overlaid with 10 ml of complete medium and placed in an incubator for 48 hours.

Forty-eight hours post-transfection, cell plates were split at a 1:4 ratio, generating four culture plates. Twenty hours later, complete medium containing 100 μg/ml of G418 plus 40 μg/ml Zeocin™ was added to the cells for 14 days. Medium was replaced every 2 to 4 days. After this period, colonies had formed on the plates and were isolated using trypsin-soaked circles of sterile filter paper. 24 isolates were cultured, 20 survived and were expanded for functional assay using fluorescence-based measurements of internal calcium concentrations (Reference to analysis of transfectants, section 2). Two parental cell lines, 83-13 and 83-19 exhibited robust expression of the 3-way combination in functional calcium assays and both were subcloned by limiting dilution.

Thirty seven subclones from parental cell line 83-19 were screened in the fluorescence-based calcium assay. Sixteen subclones were positive in this assay and showed epibatidine-induced increases in internal calcium. Twelve subclones from parental cell line 83–13 were screened in the fluorescence-based calcium assay and five subclones were positive. Four subclones, including subclone 83-19-15 were selected based on activity in calcium assays.

83-19-15 was further subcloned by limiting dilution, and 18 subclones were screened for acetylcholine-induced increases in internal calcium. Four subclones (83-19-15-26, 83-19-15-27, 83-19-15-42 and 83-19-15-48 were selected based on a positive functional response in this assay. These subclones then entered a stability study where they were monitored for acetylcholine-induced increases in internal calcium at two-weekly intervals for approximately 15 weeks.

Subclone 83-19-15-27 was selected based on the stable functional response to low doses of acetylcholine (1 μM) observed during the stability study. This cell line was confirmed to have acceptable responses as a random screening target in the high throughput screening assay and renamed A3B2A5 after validation in this assay (example 5, protocol A).

2. Analysis of Transfectants a. Fluorescent Indicator-based Assays

Activation of the ligand-gated nicotinic AChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying icotinic AChR has been described in commonly assigned pending U.S. patent application Ser. No. 07/812,254 and corresponding PCT Patent Application No. US92/11090.

HEK293 cells that were stably transfected with DNA encoding the human α3β2α5 subunit were analyzed for expression of functional recombinant nAChRs using the automated fluorescent indicator-based assay.

Briefly, untransfected HEK293 cells and HEK293 cells that had been transfected with DNA encoding human α3, α5 and β2 nAChRs were plated in the wells of a poly-D-lysine coated 96-well microtiter dish at a cell density of 75,000 to 200,000 cells per well. Cells were grown in an incubator at 37° C. for 2–3 hours, then transferred to an incubator maintained at 28° C. Forty-eight hours after plating, cell culture medium was decanted and cells washed with an assay buffer (HBK) containing 155 mM NaCl, 4.6 mM KCl, 1.2 mM $MgSO_4$, 21.8 mM $CaCl_2$, 1 μM atropine, 6 mM glucose and 20 mM HEPES-NaOH pH7.4. Washed cells were incubated with 20 μM fluo-3-acetoxymethylester containing 0.16% pluronic F-127 at 22° C. for 2 hours in the dark. Dye not taken up by cells was removed by aspiration followed by washing with 250 μl HBK. Fluorescence measurements were performed at 0.33 sec intervals using a 96-well microtiter plate-reading fluorometer (Cambridge Technology, Inc.).

Ten basal fluorescence readings were recorded prior to addition of agonist (either 100 nM epibatidine, or 1 μM acetylcholine). Responses after the addition of epibatidine were recorded for approximately 60 sec. Maximal fluorescence ($F_{max}$) was determined after lysing the cells with 0.25% Triton X-100, and minimal fluorescence ($F_{min}$) was determined after subsequent quenching with 10 mM $MnCl_2$. Calculation of $[Ca^{2+}]_i$ was performed as described by Kao et al. (1989). Cellular responses were quantitated by calculating either the ratio of peak $[Ca^{2+}]_i$ after agonist addition to the basal $[Ca^{2+}]_i$ prior to agonist addition, or by the difference between peak $[Ca^{2+}]_i$ and basal $[Ca^{2+}]_i$.

The fluorescence of the untransfected HEK cells did not change after addition of nicotine. In contrast, the fluorescence of the co-transfected cells, in the absence of d-tubocurarine, increased dramatically after addition of nicotine to the wells. This nicotine-stimulated increase in fluorescence was not observed in co-transfected cells that had been exposed to the antagonist d-tubocurarine. These results demonstrate that the co-transfected cells express the above referenced functional recombinant multimeric AChR subunit combination that were activated by nicotine and blocked by d-tubocurarine.

b. Characeristics of the Stable Cell Line A3B2A5 that Expresses the Human α3β2α5 nAChR.

Pharmacological analysis of agonist-induced increases in internal calcium using the fura-2 calcium assay (Protocol A, infra, Reference to SpeedReader patent?) showed the expression of two populations of nAChRs in A3B2A5 cells: one population displayed high sensitivity to some nAChR agonists while the second showed a sensitivity to agonists indistinguishable from that observed in cell line A3B2 (which expresses human α3β2 nAChRs). The high affinity site in A3B2A5 cells displays a 200- to 6000-fold lower $EC_{50}$ value for the agonists acetylcholine (ACh), nicotine and cytisine compared to α3β2 nAChRs. FIGS. 9a and 9b illustrate some of the pharmacology of the A3B2A5 cell line. The changes in agonist sensitivity result in a rank order of agonist potency for A3B2A5 that differs from that of A3B2 and thus demonstrates the presence of a novel receptor (α3β2α5) in cell line A3B2A5. In whole-cell voltage-clamped A3B2A5 cells, we found that the desensitization kinetics of currents elicited by low doses of ACh are significantly slower in A3B2A5 cells than A3B2 cells (Protocol B) (FIG. 10). The differences in biophysical properties of A3B2A5 and A3B2 also indicate the expression of a novel receptor, the α3β2α5 nAChR, in cell line A3B2A5 and these are illustrated in FIG. 9b. The homogeneity of the cell line was verified by single-cell imaging of agonist-induced increases in intracellular free calcium concentration (Protocol C). Co-precipitation experiments demonstrated the co-assembly of the α5 nAChR with α3 and with β2 (protocol D, FIG. 11).

The protocols for the above referenced data is presented hereafter.

A. Fluorescence-based Calcium Assays Using Fura-2.

A cell line, A3B2A5, stably transfected with DNAs encoding human α3, α5, and β2 receptors is plated in black-walled 96-well plates, grown 2 to 3 hours at 37° C. and then 2 days at 28° C. At the start of the assay, assay the plates are washed with in HEPES buffered saline (HBS) containing 1 μM atropine (HBSA) (wash cycle=aspirate, dispense×3) to leave 180 μl residual HBSA per well. Then a background measurement of a sample plate is taken by the SpeedReader for 20 frames alternating the excitation light between 350 and 385 nm at four hertz. Twenty μl of 10 μM fura-2 dye containing is then added to each well and incubated with the cells at ambient temperature for one hour to two hours. After dye loading the free dye is washed from the wells with HBSA to leave 180 μl residual buffer per well. Two minutes after washing, a kinetic reading is taken while the test chemicals are added. The test compounds are prepared in HBSA containing 80 mM $CaCl_2$ and 1% DMSO. The kinetic reading is composed of 140 frames, alternating between 350 and 385 as in the 20 frame background reading. However, the first 20 frames of the kinetic reading are taken before test chemical addition. The difference between these 20 frames and the background give the fluorescence due to the Ca-indicating dye fura-2. After the first 20 frames are collected 20 μl of the test compound is dispensed from a 96-channel pipettor to the entire plate at once without halting the reading. The remainder of the 120 frames of data measure the response.

Absolute Ca concentrations are not calculated from these readings, rather the directly measured fluorescence ratio is used as a surrogate for Ca. The fluorescence ratio is calculated as dye fluorescence generated by excitation at 350 nm divided by dye fluorescence generated by excitation at 385 nm. The raw activity in a well is calculated as the maximum fluorescence ratio after compound addition divided by the average fluorescence ratio before compound addition.

B. Electrophysiological Analysis

Electrophysiological measurements may be used to assess the activity of recombinant receptors or to assess the ability of a test compound to potentiate, antagonize or otherwise modulate the magnitude and duration of the flow of cations through the ligand-gated recombinant AChR. The function of the expressed neuronal AChR can be assessed by a variety of electrophysiological techniques, including two-electrode voltage clamp and patch clamp methods. The cation-conducting channel intrinsic to the AChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques.

HEK293 cells stably transfected with DNA encoding the human α3, β2 and α5 subunits were analyzed electrophysiologically for the presence of nAChR agonist-dependent currents. HEK293 cells stably expressing human α3, β2 and α5 nAChRs were plated at a density of $1.5 \times 10^5$ cells/35-mm dish on poly-D-lysine-coated glass coverslips (0.1 mg/ml, SIGMA) and incubated at 37° C. for 2–3 hours, then for 48 hours at 28° C. Recordings were performed with an Axopatch 200A amplifier (Axon Instruments) using the whole-cell voltage-clamp configuration. Membrane potential was held at −100 mV. The standard external recording solution (mammalian Ringer's) consisted of (in mM) 160 NaCl, 5 KCl, 2 $CaCl_2$, 1 $MgCl_2$, 11 glucose, 0.001 atropine, and 5 HEPES, pH 7.3. Ringer's solution was superfused at a rate of ≈3.0 ml/min (110 μl recording chamber). The recording pipette solution was composed of 135 mM CsCl, 10 mM EGTA, 1 mM $MgCl_2$ and 10 mM HEPES, pH 7.3 (with or without 4 mM Mg-ATP). Experiments were performed at room temperature. Agonist, dissolved in Ringer's solution, was applied for 200–500 ms using a fast application system, consisting of a triple-barrel glass pipette attached to an electromechanical switching device (piezoelectric drive, Winston Electronics). The speed of solution exchange between control and nicotine-containing solutions, measured as the open-tip response, displays a time constant τ=0.7 ms, with steady state reached <3 ms. Data were digitized at 6.7 kHz and filtered at 2 kHz on line. Data analysis was performed using pClamp software (Axon Instruments).

B. Single Cell Calcium Imaging Assays Using Fura-2

Cells stably transfected with DNAs encoding human α3, β2 and α5 nAChR subunits were plated on poly-D-lysine-coated glass coverslips at a density of $3 \times 10^5$ cells/35 mm dish and grown at 28° C. Forty-eight hours later, imaging experiments were performed at room temperature, using a Nikon TE200 inverted microscope attached to a DeltaRAM imaging System (Photon Technology International). Cells were incubated with 1 μM fura-2-AM (Molecular Probes, Inc.) for 0.5–1 h and washed with mammalian Ringer's solution (see example 4, 2c for composition) to remove excess dye. Cells were transferred to a recording chamber (110 μl, Warner Instruments), and continuously superfused with HBK containing 21.8 mM $CaCl_2$ and 1 μM atropine at a rate of 8–10 ml/min. Agonist was applied by switching between reservoirs. Cells were alternatively excited at 360 and 381 nm (0.5 Hz) to determine ratio images.

C. Western Analysis and Immunoprecipitation to Demonstrate Co-expression of α3, β2 and α5 nAChR Subunit Proteins.

Cells stably transfected with DNA encoding human α3, β2 and α5 nAChR subunits were harvested from 10-cm plates and washed with phosphate-buffered saline (PBS; 140 mM NaCl, 3 mM KCl, 10 mM $Na_2HPO_4$, 2 mM $KH_2PO_4$, pH 7.4). Washed cells were resuspended in 50 mM Tris pH 7.4, 1 mM EDTA containing a cocktail of protease inhibitors (Complete™, Boehringer Mannheim, Indianapolis, Ind.) and homogenized with a Dounce homogenizer. The homogenate was centrifuged at 1000×g for 5 min to remove cellular debris, and the supernatant fraction was centrifuged at 100,000×g for 120 min to pellet the membranes. The membranes were resuspended in RIPA buffer (50 mM Tris pH 7.6, 150 mM NaCl, 0.5% deoxycholate, 1% Nonidet P-40, 1% SDS) containing protease inhibitor cocktail.

For immunoprecipitation experiments, 200 µg of membranes were immunoprecipitated with 20 µg of a sheep anti-rat α3 polyclonal antibody (Bethyl Laboratories, or 2 µg a rabbit anti-human β2 polyclonal antibody (MRL San Diego) overnight at 4° C. The antibody-antigen complexes were affinity-purified using Protein G sepharose, incubated overnight at 4° C. then solubilized in SDS sample buffer. For immunoblot analysis, membranes were solubilized in Tris-Glycine SDS Sample Buffer (Novex) containing 5% 2-mercaptoethanol and heated at 65° C. for 10 min. Solubilized proteins were separated by polyacrylamide gel electrophoresis under denaturing conditions (SDS-PAGE) and electroblotted onto nitrocellulose membranes (Hy-Bond ECL, Amersham, Arlington Heights, Ill.). Blots were rinsed once in PBS, 0.1% Tween-20 (wash buffer), then blocked for 3 h in 5% Carnation non-fat dry milk dissolved in wash buffer (blocking buffer).

The human α5 protein was detected with a sheep anti-rat α5 antibody (Bethyl Laboratories). The α5 antibody was diluted to 15 µg/ml in blocking buffer and incubated with the nitrocellulose membrane for 3 h at room temperature. The membranes were washed three times in wash buffer. The secondary antibody was peroxidase-conjugated donkey anti-sheep IgG (Cappell Antibodies) diluted 1:1000 in blocking buffer and incubated with membranes for 45 min at room temperature, followed by five changes of wash buffer. The antibody signal was visualized using the ECL developing system (Amersham) according to the manufacturer's directions.

The above strategy may be employed in expressing any one of the following multimeric subunit combinations of the alpha and beta subunit sof nAChR, especially when the nucleic acid molecule encoding each individual nAChR subunit is disclosed herein. In view of the above data, it is not seen why the proposed combinations appearing below would not act in a manner similar to the multimeric subunit combination discussed immediately above.

α2β4α6
α3β4α6
α4β4α5
α4β4α6
α4β2α5
α4β2β3
α3β2α6β3
α2β4α5
α2β2α5
αXβ2β4, where X refers to one or more of the α subunts disclosed herein.
αXβ2β3β4, where X refers to one or more of the α subunts disclosed herein
aXb2b3, where X refers to one or more of the α subunits disclosed herein
α2β2α6
α3β2α6
α4β2α6

Five-way combinations of subunits, represented by the general formula $\alpha_n\beta_m$, wherein n and m are each 0–5 (where the α subunit is one or more of $\alpha_1$ thru $\alpha_7$ and β is any one or more of $\beta_2$, $\beta_3$ or $\beta_4$ are also contemplated by the present invetion. Likewise, four-way combinations are also a feature of the invention.

III. Recombinant Expression of the Human α7 nAChR in a Non-human Cell Line

A. Construct for Expression of Recombinant Human nNAChR $\alpha_7$ in a Non-human Host Cell Line The isolated cDNA Encoding human neuronal α7 AChR was incorporated into the expression vector pcDNA3 (Invitrogen) for use in expressing the α7 subunit in the $GH_4C_1$ host cell line. The expression vector, pcDNA3-KEα7RBS was constructed as described below.

Construct pCMV-KEα7 was digested with BamHI and XhoI to release a 1.8 kb DNA fragment containing a consensus ribosome binding site (RBS) immediately 5' to the translation initiation codon of α7 and also containing the entire α7 coding region. pGEM/KEα7RBS was prepared by ligating this 1.8 kb DNA fragment into BamHI, XhoI digested pGEM-7Zf(+), (Promega). pGEM/KEα7RBS was digested with BamHI and XhoI to release the 1.8 kb DNA fragment containing the RBS and α7 coding region. pcDNA3-KEα7RBS was prepared by ligating the 1.8 kb fragment from pGEM/KEα7RBS into BamHI and XhoI digested pcDNA3.

B. Recombinant Expression of the Human α7 nAChR in $GH_4C_1$ cells.

$GH_4C_1$ cells, derived from rat pituitary tumor tissue, were stably transfected with DNA encoding human neuronal nAChR α7 and analyzed for expression of nAChRs using various assays, for example calcium sensitive fluorescent indicator-based assays, [$^{125}$I] bungarotoxin binding and electrophysiological methods.

1. Stable Transfection of $GH_4C_1$ Cells with the Human α7 nAChR.

$GH_4C_1$ cells were stably transfected with DNA encoding human neuronal nAChR α7 using the lipofection transfection procedure (Current Protocols in Molecular Biology, Volume 1, 9.4.1–9.4.5 and 9.5.1–9.5.6, incorporated herein by reference).

$GH_4C_1$ cells were harvested using Cell Dissociation Buffer (Sigma) and plated onto 10 cm tissue culture plates coated with poly-d-lysine at a concentration of 1.2 million cells per plate, 24 hours prior to transfection. Six micrograms of the α7 expression vector, pcDNA3-KEα7RBS were diluted in 300 µl of Dulbecco's Modified Eagle Medium (DMEM) and combined with 20 µl of LipofectAMINE™ Reagent (Gibco-BRL) for 15 minutes. The $GH_4C_1$ cells were washed twice with DMEM. This DNA/LipofectAMINE mixture was further diluted into 5.3 ml of DMEM and overlaid onto the $GH_4C_1$ cells. The overlaid cells were incubated for 5 hours in an incubator at 37° C., in a humidified atmosphere containing 6% carbon dioxide. Cell plates were washed twice with 5 mls of Ham's F-10 nutrient mixture (GibcoBRL) containing 10% fetal bovine serum, 100 units per ml of penicillin and 100 µg/ml streptomycin then overlaid with 10 ml of complete medium and placed in an incubator for 48 hours.

Forty-eight hours post-transfection, cell plates were split at a 1:4 ratio, generating four culture plates. Twenty hours later, complete medium containing 500 µg/ml of G418 was added to the cells for 14 days. Medium was replaced every 2 to 4 days. After this period, colonies had formed on the plates and were isolated using trypsin-soaked circles of sterile filter paper. 24 isolates were cultured, 18 survived and were expanded for functional assay using fluorescence-based measurements of internal calcium concentrations as descried in Example 4 above.

Clones were also screened in a radioligand binding assay using [$^{125}$I]-bungarotoxin. See example 4. Electrophysiological recordings (similar to the procedue outlined in Example 4) also demonstrated currents with biophysical properties characteristic of the α7 receptor. Parental cell line G1-9 exhited robust expression in both functional calcium and electrophysiological assays and in binding assays. The G1-9 parental cell line was subcloned by limiting dilution.

Twenty eight subclones from G1-9 were screened in the fluorescence-based calcium assay. Ten subclones were positive in this assay and showed epibatidine-induced increases in internal calcium. An additional binding assay, similar to that outlined above, identified thirteen positive subclones.

Five subclones, including subclone G1-19-15 were selected based on activity in both calcium and binding assays.

G1-9-15 was further subcloned by limiting dilution, subclones were screened for epibatidine-induced increases in internal calcium. Four subclones, G1-9-15-8, G1-9-15-18, G1-9-15-28 and G1-9-15-35 were selected based on a positive functional response in this assay. These subclones then entered a stability study where they were monitored for functional response in the calcium assay at two-weekly intervals for approximately 15 weeks.

Subclone G1-9-15-8 was selected based on the stable functional response observed during the stability study. This cell line was confirmed to have acceptable responses as a random screening target in the high throughput screening assay and renamed A7 after validation in this assay.

2. Analysis of Transfectants a. Fluorescence-based Measurements of Internal Calcium Concentrations.

$GH_4C_1$ cells that were stably transfected with DNA encoding the human α7 subunit were analyzed for expression of functional recombinant nAChRs using the automated fluorescent indicator-based assay.

Activation of the ligand-gated nicotinic AChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying icotinic AChR has been described in commonly assigned pending U.S. patent application Ser. No. 07/812,254 and corresponding PCT Patent Application No. US92/11090.

Untransfected $GH_4C_1$ cells and $GH_4C_1$ cells that had been transfected with pcDNA3-KEα7RBS were plated in the wells of a poly-D-lysine coated 96-well microtiter dish at a cell density of 75,000 to 200,000 cells per well. Twenty four hours after plating, cell culture medium was decanted and cells washed with an assay buffer (HBK) containing 155 mM NaCl, 4.6 mM KCl, 1.2 mM $MgSO_4$, 1.8 mM $CaCl_2$, 1 µM atropine, 6 mM glucose and 20 mM Hepes-NaOH pH7.4. Washed cells were incubated with 20 µM fluo-3-acetoxymethylester containing 0.16% pluronic F-127 at 22° C. for 2 hours in the dark. Dye not taken up by cells was removed by aspiration followed by washing with 250 µl HBK. Fluorescence measurements were performed at 0.33 sec intervals using a 96-well microtiter plate-reading fluorometer (Cambridge Technology, Inc.). Cells were incubated for 10 minutes with 3 µM FPL 64176 and ten basal fluorescence readings were recorded prior to addition of 1 µM epibatidine. Responses after the addition of epibatidine were recorded for approximately 60 sec. Alpha-bungarotoxin was tested after a preincubation period of 5–10 min. Maximal fluorescence ($F_{max}$) was determined after lysing the cells with 0.25% Triton X-100, and minimal fluorescence ($F_{min}$) was determined after subsequent quenching with 10 mM $MnCl_2$. Calculation of $[Ca^{2+}]_i$ was performed as described by Kao et al. (1989). Cellular responses were quantitated by calculating either the ratio of peak $[Ca^{2+}]_i$ after agonist addition to the basal $[Ca^{2+}]_i$ prior to agonist addition, or by the difference between peak $[Ca^{2+}]_i$ and basal $[Ca^{2+}]_i$.

b. α-Bungarotoxin Binding Assays

Untransfected $GH_4C_1$ cells and $GH_4C_1$ cells that were stably transfected with DNA encoding the human α7 subunit were analyzed for [$^{125}$I]-α-bungarotoxin binding. The assay procedure was as follows.

Cells were incubated with 1 nM [$^{125}$I]-α BTX in culture media for 2 hours at room temperature. Non-specific binding was determined in the presence of 1 µM unlabeled toxin. The assays were terminated by aspiration of the culture media and rapid filtration through Whatman GF/C filters using a Brandel Cell Harvester. Filters were washed with approximately 4×1 ml washes of ice cold binding assay buffer (50 mM tris, 140 mM NaCl, 5 nM KCl, 2 mM $CaCl_2$, 1 mM $MgCl_2$, pH 7.4). Filter disks were transferred to scintillation vials containing 5 ml Ecolume scintillation cocktail and radioactivity counted using a Beckman 6500 scintillation spectrometer.

c. Electrophysiological Analysis of $GH_4C_1$ Cells Transfected with Human Neuronal Nicotinic AChR Subunit-encoding DNA (Human α7 Subunit)

Electrophysiological measurements may be used to assess the activity of recombinant receptors or to assess the ability of a test compound to potentiate, antagonize or otherwise modulate the magnitude and duration of the flow of cations through the ligand-gated recombinant AChR. The function of the expressed neuronal AChR can be assessed by a variety of electrophysiological techniques, including two-electrode voltage clamp and patch clamp methods. The cation-conducting channel intrinsic to the AChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques.

$GH_4C_1$ cells stably transfected with DNA encoding the human $α_7$ subunit were analyzed electrophysiologically for the presence of nAChR agonist-dependent currents. GH4C1 cells stably expressing human α7 nAChRs were plated at a density of 1.5×10$^5$ cells/35-mm dish on collagen-coated glass coverslips (rat collagen I, Becton Dickinson) treated with an additional coating of poly-D-lysine (0.1 mg/ml, SIGMA). Recordings were performed with an Axopatch 200A amplifier (Axon Instruments) using the whole-cell voltage-clamp configuration. Membrane potential was held at −100 mV. The standard external recording solution (mammalian Ringer's) consisted of (in mM) 160 NaCl, 5 KCl, 2 CaCl$_2$, 1 MgCl$_2$, 11 glucose, 0.001 atropine, and 5 HEPES, pH 7.3. Ringer's solution was superfused at a rate of ≈3.0 ml/min (110 µl recording chamber). The recording pipette solution was composed of 135 mM CsCl, 10 mM EGTA, 1 mM MgCl$_2$ and 10 mM HEPES, pH 7.3 (with or without 4 mM Mg-ATP). Experiments were performed at room temperature. Nicotine (100–300 µM), dissolved in Ringer's solution, was applied for 200–500 ms using a fast application system, consisting of a triple-barrel glass pipette attached to an electromechanical switching device (piezoelectric drive, Winston Electronics). The speed of solution exchange between control and nicotine-containing solutions, measured as the open-tip response, displays a time constant τ=0.7 ms, with steady state reached <3 ms. Data were digitized at 6.7 kHz and filtered at 2 kHz on line. Data analysis was performed using pClamp software (Axon Instruments).

EXAMPLE 5

Characterization of Cell Lines Expressing nNAChRs

Recombinant cell lines generated by transfection with DNA encoding human neuronal nicotinic AChRs, such as those described in Example 3 can be further characterized using one or more of the following methods.

A. Northern or Slot Blot Analysis for Expression of α- and/or β-subunit Encoding Messages Total RNA is isolated from ~1×10$^7$ cells and 10–15 µg of RNA from each cell type is used for northern or slot blot hybridization analysis. The inserts from human neuronal NAChR-encoding plasmids can be nick-translated and used as probe. In addition, the β-actin gene sequence (Cleveland et al. (1980) Cell 20:95–105) can be nick-translated and used as a control probe on duplicate filters to confirm the presence or absence of RNA on each blot and to provide a rough standard for use in quantitating differences in α- or β-specific mRNA levels between cell lines. Typical northern and slot blot hybridization and wash conditions are as follows:

hybridization in 5×SSPE, 5× Denhardt's solution, 50% formamide, at 42° C. followed by washing in 0.2× SSPE, 0.1% SDS, at 65° C.

B. Nicotine-binding Assay

Cell lines generated by transfection with human neuronal nicotinic AChR α- or α- and β-subunit-encoding DNA can be analyzed for their ability to bind nicotine, for example, as compared to control cell lines: neuronally-derived cell lines PC12 (Boulter et al., (1986), supra; ATCC #CRL1721) and IMR32 (Clementi, et al. (1986); Int. J. Neurochem. 47:291–297; ATCC #CCL127), and muscle-derived cell line BC3H1 (Patrick, et al, (1977); J. Biol. Chem. 252:2143–2153. Negative control cells (i.e., host cells from which the transfectants were prepared) are also included in the assay. The assay is conducted as follows:

Just prior to being assayed, transfected cells are removed from plates by scraping. Positive control cells used are PC12, BC3H1, and IMR32 (which had been starved for fresh media for seven days). Control cell lines are removed by rinsing in 37° C. assay buffer (50 mM Tris/HCl, 1 mM MgCl$_2$, 2 mM CaCl$_2$, 120 mM NaCl 3 mM EDTA, 2 mg/ml BSA and 0.1% aprotinin at pH7.4). The cells are washed and resuspended to a concentration of 1×10$^6$/250 µl. To each plastic assay tube is added 250 µl of the cell solution, 15 nM $^3$H-nicotine, with or without 1 mM unlabeled nicotine, and assay buffer to make a final volume of 500 µl. The assays for the transfected cell lines are incubated for 30 min at room temperature; the assays of the positive control cells are incubated for 2 min at 1° C. After the appropriate incubation time, 450 µl aliquots of assay volume are filtered through Whatman GF/C glass fiber filters which has been pretreated by incubation in 0.05% polyethyleneimine for 24 hours at 4° C. The filters are then washed twice, with 4 ml each wash, with ice cold assay buffer. After washing, the filters are dried, added to vials containing 5 ml scintillation fluid and radioactivity is measured.

C. $^{86}$Rb ion-flux Assay

The ability of nicotine or nicotine agonists and antagonists to mediate the influx of $^{86}$Rb into transfected and control cells has been found to provide an indication of the presence of functional AChRs on the cell surface. The $^{86}$Rb ion-flux assay is conducted as follows:

1. The night before the experiment, cells are plated at 2×10$^6$ per well (i.e., 2 ml per well) in a 6-well polylysine-coatedplate.
2. The culture medium is decanted and the plate washed with 2 ml of assay buffer (50 mM HEPES, 260 mM sucrose, 5.4 mM KCl, 1.8 mM CaCl$_2$, 0.8 mM MgsO$_4$, 5.5. mM glucose) at room temperature.
3. The assay buffer is decanted and 1 ml of assay buffer, containing 3 µCi/ml $^{86}$Rb, with 5 mM ouabain and agonist or antagonist in a concentration to effect a maximum response, is added.
4. The plate is incubated on ice at 1° C. for 4 min.
5. The buffer is decanted into a waste container and each well was washed with 3 ml of assay buffer, followed by two washes of 2 ml each.
6. The cells are lysed with 2×0.5 ml of 0.2% SDS per well and transferred to a scintillation vial containing 5 ml of scintillation fluid.
7. The radioactivity contained in each vial is measured and the data calculated.

Positive control cells provided the following data in this assay:

|  | PC12 | | IMR32 | |
|---|---|---|---|---|
|  | EC$_{50}$ | Maximum response | EC$_{50}$ | Maximum response |
| Agonist |  |  |  |  |
| nicotine | 52 µM | 2.1 X[a] | 18 µM | 7.7 X[a] |
| CCh* | 35 µM | 3.3 X[b] | 230 µM | 7.6 X[c] |
| cytisine | 57 µM | 3.6 X[d] | 14 µM | 10 X[e] |
| Antagonist |  |  |  |  |
| d-tubocurarine | 0.81 µM |  | 2.5 µM |  |
| mecamylamine | 0.42 µM |  | 0.11 µM |  |
| hexamethonium | nd[f] |  | 22 µM |  |
| atropine | 12.5 µM |  | 43 µM |  |

*CCh = carbamylcholine
[a]200 µM nicotine
[b]300 µM CCh
[c]3 mM CCh
[d]1 mM cytisine
[e]100 µM cytisine
[f]nd = not determined D. Electrophysiological Analysis of Mammalian Cells Transfected with Human Neuronal Nicotinic AChR Subunit-encoding DNA Electrophysiological measurements may be used to assess the activity of recombinant receptors or to assess the ability of a test compound to potentiate, antagonize or otherwise modulate the magnitude and duration of the flow of cations through the ligand-gated recombinant AChR. The function of the expressed neuronal AChR can be assessed by a variety of electrophysiological techniques, including two-electrode voltage clamp and patch clamp methods. The cation-conducting channel intrinsic to the AChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques. In preferred embodiments, transfected mammalian cells or injected oocytes are analyzed electrophysiologically for the presence of AChR agonist-dependent currents.

EXAMPLE 6

Characterization of $GH_4C_1$ Cells Stably Expressing the Human α7 nAChR

The cell line A7 that stably expressed the human α7 nAChR was characterized in multiple assays that are described below.

Dose response curves to reference nicotinic agonists nicotine and acetylcholine were obtained for cell line A7 using the fura-2 based calcium assay. See protocol A infra.

Figure 3A:
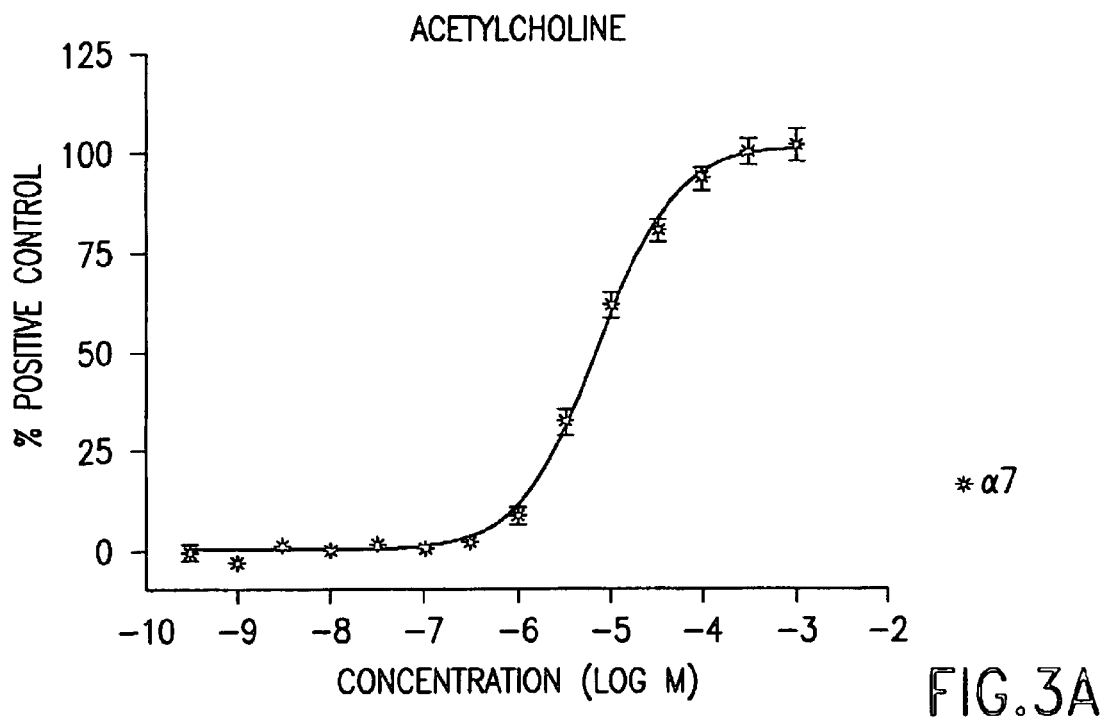
FIG. 3 depicts the nicotine and acetylcholine-induced dose-response curves foe the A7 cell line obtained from functional bulk calcium assays.
Figure 3B:
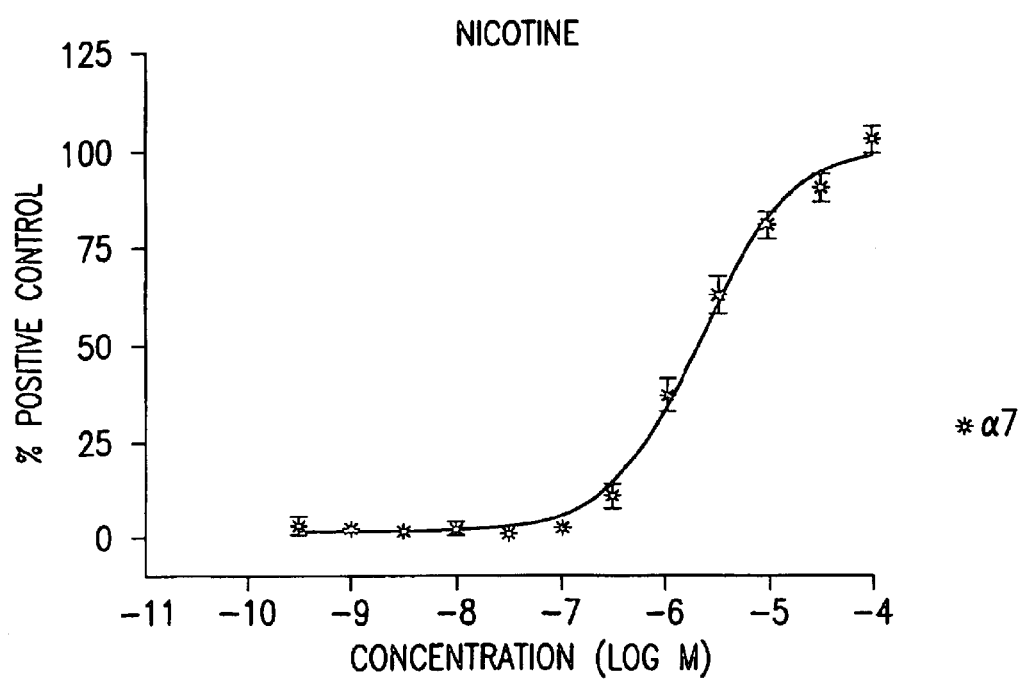

Refering to FIG. 3, the $EC_{50}$ for nicotine was 2 μM and for acetylcholine was 7 μM. This is in agreement with that reported for the α7 nAChR (Peng et al (1993) Mol Pharmacol. 45:546–554).

Figure 4:
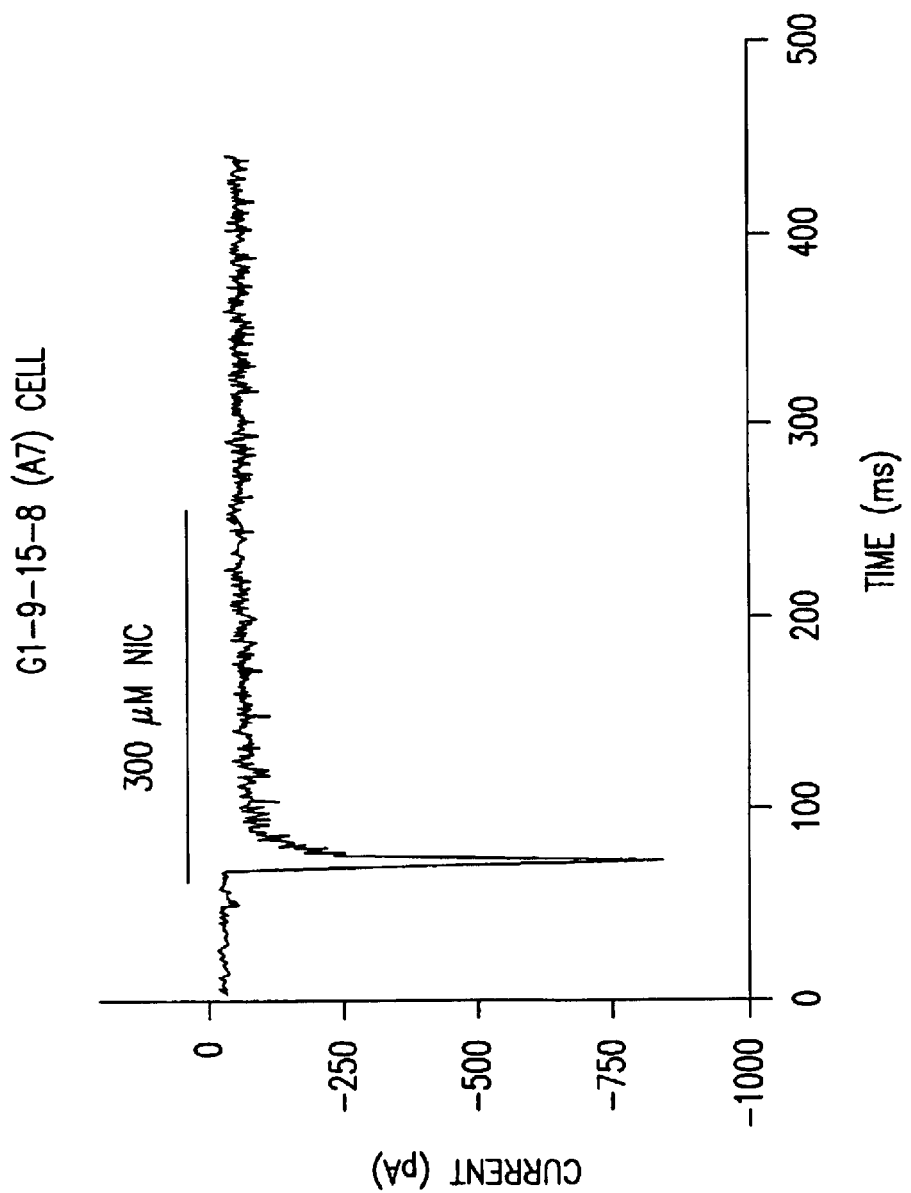
FIG. 4 depicts the kinetics of the A7 stable cell line obatined by electrophysiological analysis.

Data on electrophysiological characterization using whole-cell voltage-clamped A7 cells is depicted in FIG. 4, which show rapidly desensitizing currents that are consistent with those reported for α7 nAChRs. The protoclos for these experimenst were the same as those described in Examples 3 and 4 above. In these studies 90% to 100% of voltage-clamped A7 cells responded to the application of 300 μM nicotine.

Figure 6:
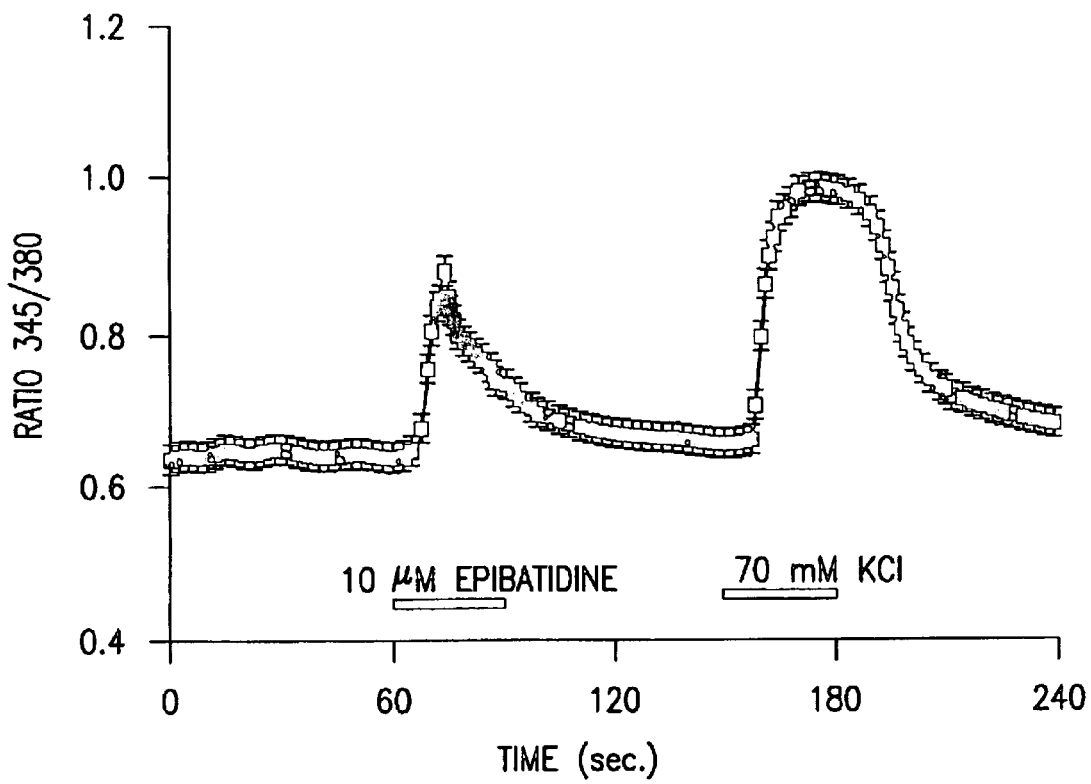
FIG. 6 depicts the results of a single cell calcium imaging of the A7 cell line, showing the homogeneity of the response of the A7 cell line to acetylcholine.

Single cell calcium imaging of the A7 cell line (FIG. 6) (protocol B, infra) supports the conclusion that individual cells in this cell line (A7) respond to 10 μM epibatidine in a homogenous manner.

Figure 5:
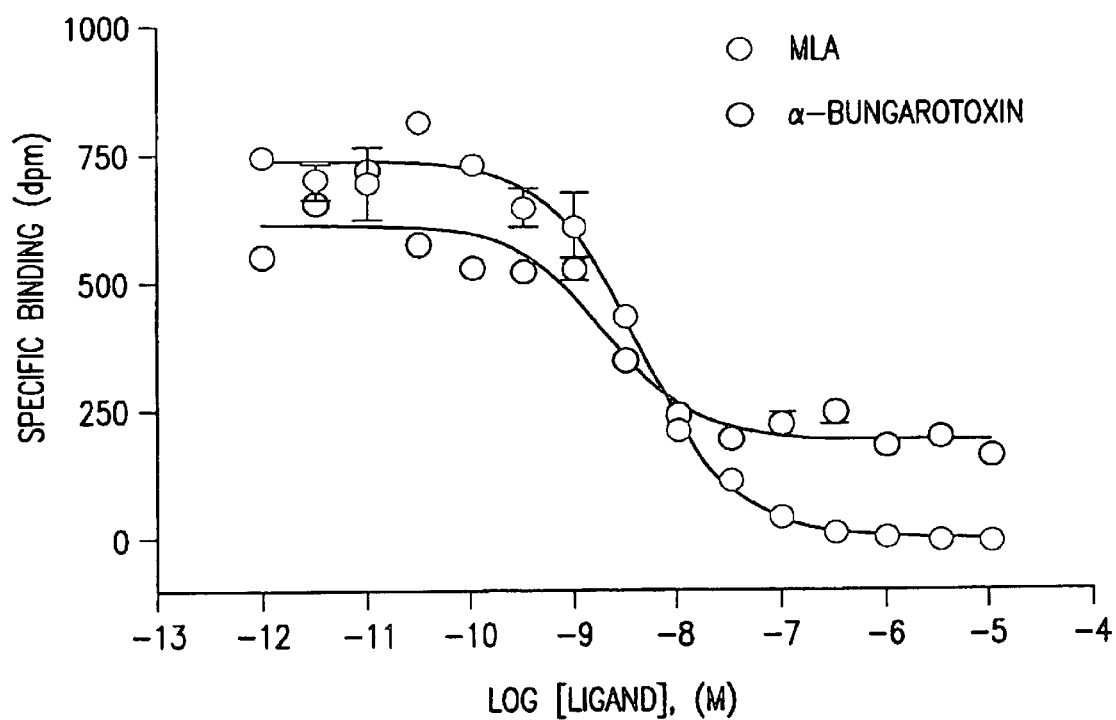
FIG. 5 depicts the MLA and α-bungarotoxin (ligands of A7) binding assay of A7.

In radioligand binding studies (protocol C, infra) methyllycaconitine (MLA) displaced [$^3$H]-MLA binding from the α7 nAChRs in cell line A7 with an $IC_{50}$ of 4 nM, similar to the $IC_{50}$ value obtained with α-bungarotoxin (3 nM). These $IC_{50}$ values are similar to published affinities (for example, Davies et al. 1999, Neuropharmacology 38:679). α-bungarotoxin displaced approximately 65% of the [$^3$H]-MLA binding in A7. Cells are permeable to MLA but not to α-bungarotoxin under these assay conditions. This therefore demonstrates that 65% of the α7 nAChRs in cell line A7 are expressed on the plasma membrane (i.e. at the cell surface). This data is illustrated in FIG. 5.

Figure 7:
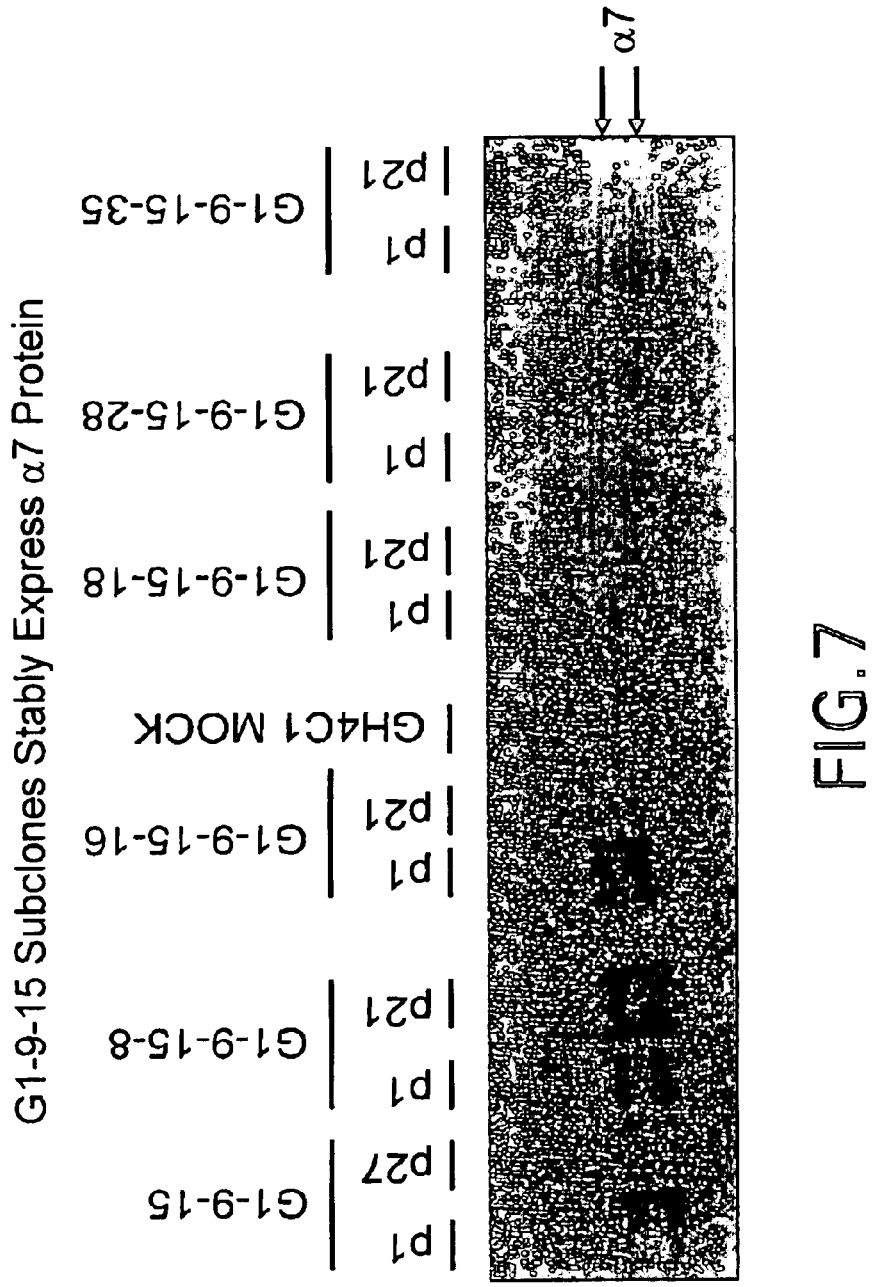
FIG. 7 depicts the results of a Western blot analysis using an A-7 specific antibody as a probe. The data specifically confirm expression of the $\alpha_7$ protein by the A7 cells.

A molecular characterization was undertaken to demonstrate the expression of α7 nAChR protein and α7 mRNA in the stable cell line A7. Western analysis using an α7-specific antibody demonstrated that cell line A7 expressed protein of approximately 54 kDa. Protein prepared from the untransfected $GH_4C_1$ cell line does not show any hybridization with this antibody. Refer to FIG. 7.

Figure 8:
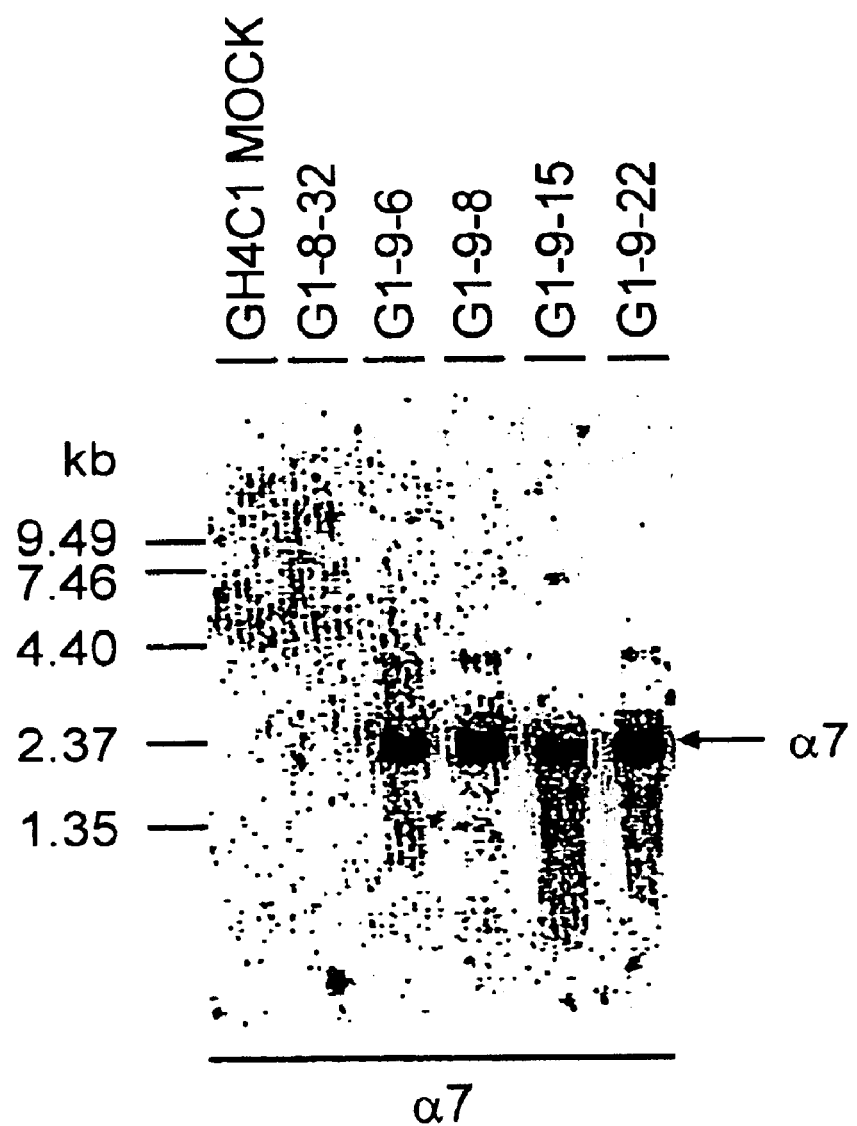
FIG. 8 shows the results of a Northen Blot analysis of total RNA prepared from A7 cells.

Northern analysis of total RNA prepared from A7 cells showed that these cells express an RNA species that hybridizes with a subunit specific DNA probe. The hybridizing band has a molecular weight of approximately 2.4 kb. No hybridizing species was detected in untransfected $GH_4C_1$ cells. Refer to FIG. 8.

The characterizations of stable cell line A7 described above were generated using the following protocols .

A. Fluorescence Based Calcium Assays using Fura-2

A cell line A7 stably transfected with the human α7 nAChR receptor is plated in black-walled 96-well plates and grown at 37° C. Twenty-four hours later, the plates are washed with in HEPES buffered saline (HBS) containing 1 μM atropine (HBSA) (wash cycle=aspirate, dispense×3) to leave 180 μl residual HBSA per well. At the start of the assay, a background measurement of a sample plate was taken by the SpeedReader for 20 frames alternating the excitation light between 350 and 385 nm at four hertz. See U.S. Pat. Nos. 5,670,113 and 6,057,114, each of which is incorportaed by reference herein in their entirety. Twenty μl of 10 μM fura-2 dye containing 3 μM FPL-64176 is then added to each well and incubated with the cells at ambient temperature for one to two hours. After dye loading the free dye is washed from the wells with HBSA containing 0.5 μM FPL-64176 to leave 180 μl residual buffer per well. Two minutes after washing, a kinetic reading is taken while the test chemicals are added. The test compounds are prepared in HBSA containing 80 mM $CaCl_2$ and 1% DMSO. The kinetic reading is composed of 140 frames, alternating between 350 and 385 as in the 20 frame background reading. However, the first 20 frames of the kinetic reading are taken before test chemical addition. The difference between these 20 frames and the background give the fluorescence due to the calcium-indicating dye fura-2. After the first 20 frames are collected 20 μl of the test compound is dispensed from a 96-channel pipettor to the entire plate at once without halting the reading. The remainder of the 120 frames of data measure the response.

Absolute calcium concentrations are not calculated from these readings, rather the directly measured fluorescence ratio is used as a surrogate for calcium. The fluorescence ratio is calculated as dye fluorescence generated by excitation at 350 nm divided by dye fluorescence generated by excitation at 385 nm. The raw activity in a well is calculated as the maximum fluorescence ratio after compound addition divided by the average fluorescence ratio before compound addition.

B. Single Cell Calcium Imaging Assays using Fura-2

Cells stably transfected with the human α7 nAChR were plated on poly-D-lysine-coated glass coverslips at a density of $3\times10^5$ cells/35 mm dish. Twenty four hours later, imaging experiments were performed at room temperature, using a Nikon TE200 inverted microscope attached to a DeltaRAM imaging System (Photon Technology International). Cells were incubated with 1 μM fura-2-AM (Molecular Probes, Inc.) for 0.5–1 h and washed with mammalian Ringer's solution (see example above re: the ephys composition of this buffer eg Ringers (in mM) 160 NaCl, 5 KCl, 1 MgCl etc.) to remove excess dye. Cells were transferred to a recording chamber (110 μl, Warner Instruments), and continuously superfused with HBK containing 1 μM atropine at a rate of 8–10 ml/min. 10 μM epibatidine was applied by switching between reservoirs. Cells were alternatively excited at 360 and 381 nm (0.5 Hz) to determine ratio images.

C. Radioligand Binding Studies

GH4C1 cells stably expressing α7 were plated in 96-well microtiter plates at a density of 200,000 cells per well. Twenty-four hours later, cells were washed in assay buffer (50 mM Tris, 140 mM NaCl, 5 mM KCl, 2 mM $CaCl_2$, 1 mM $MgCl_2$, pH 7.4), and incubated with 1 nM [$^3$H]-methyllycaconitine in the presence of increasing concentrations of either methyllycaconitine (MLA) or α-bungarotoxin. After 120 min, the assay was terminated by aspiration of the buffer and rapid filtration through Whatman GF/C filters using a Brandel Cell Harvester. Filters were washed with approximately 4×1 ml washes of ice cold assay buffer, and filter disks transferred to scintillation vials containing 5 ml Ecolume scintillation cocktail. Radioactivity was counted using a Beckman 6500 scintillation spectrometer. Specific binding was calculated by subtracting the non-specific binding, defined by 10 µM MLA.

D. Western Analysis for Expression of α7 Protein

Cells stably transfected with the human α7 nAChR were harvested from 10-cm plates and washed with phosphate-buffered saline (PBS; 140 mM NaCl, 3 mM KCl, 10 mM $Na_2HPO_4$, 2 mM $KH_2PO_4$, pH 7.4). Washed cells were resuspended in 50 mM Tris pH 7.4, 1 mM EDTA containing a cocktail of protease inhibitors (Complete™, Boehringer Mannheim, Indianapolis, Ind.) and homogenized with a Dounce homogenizer. The homogenate was centrifuged at 1000×g for 5 min to remove cellular debris, and the supernatant fraction was centrifuged at 100,000×g for 120 min to pellet the membranes. The membranes were resuspended in RIPA buffer (50 mM Tris pH 7.6, 150 mM NaCl, 0.5% deoxycholate, 1% Nonidet P-40, 1% SDS) containing protease inhibitor cocktail.

For immunoblot analysis, membranes were solubilized in Tris-Glycine SDS Sample Buffer (Novex, San Diego, Calif.) containing 5% 2-mercaptoethanol and heated at 65° C. for 10 min. Solubilized proteins were separated by polyacrylamide gel electrophoresis under denaturing conditions (SDS-PAGE) and electroblotted onto nitrocellulose membranes (Hy-Bond ECL, Amersham, Arlington Heights, Ill.). Blots were rinsed once in PBS, 0.1% Tween-20 (wash buffer), then blocked for 3 h in 5% Carnation non-fat dry milk dissolved in wash buffer (blocking buffer).

The human α7 protein was detected with an antibody raised in goat against a human α7-specific peptide (Santa Cruz Biotechnology). The primary antibody was diluted to 0.5 µg/ml in blocking buffer and incubated with the nitrocellulose membrane for 3 h at room temperature. The membranes were washed three times in wash buffer. The secondary antibody was peroxidase-conjugated donkey anti-goat IgG (Santa Cruz Biotechnology) diluted 1:2500 in blocking buffer and incubated with membranes for 45 min at room temperature, followed by five changes of wash buffer. The antibody signal was visualized using the ECL developing system (Amersham) according to the manufacturer's directions.

E. Northern Analysis for Expression of α7 Encoding Message.

Total RNA was isolated from approximately 1×10⁷ cells for northern hybridization analysis. Total RNA was size-fractionated on an agarose-formaldehyde gel and blotted to nylon by downward alkaline transfer. Blots were hybridized with digoxygenin-labeled DNA probes specific for human α7 subunits (nucleic acid numbers 1066–1533). Blots were hybridized overnight with 20 ng/ml probe and washed at high stringency in a wash buffer containing 0.1×SSPE (3 mM NaCl, 0.2 mM $NaH_2PO_4$, 0.02 mM EDTA) and 0.1% SDS at 65° C. Chemiluminescent detection was performed using the Genius 7 kit (Boehringer Mannheim) according to the manufacturer's instructions. Refer to FIG. 8.

While the invention has been described in detail with reference to certain preferred embodiments thereof, it will be understood that modifications and variations are within the spirit and scope of that which is described and claimed.

SUMMARY OF SEQUENCES

Sequence ID No. 1 is a nucleotide sequence encoding an $α_2$ subunit of human neuronal nicotinic acetylcholine receptor, and the deduced amino acid sequence thereof.

Sequence ID No. 2 is the amino acid sequence of the $α_2$ subunit of human neuronal nicotinic acetylcholine receptor set forth in Sequence ID No. 1.

Sequence ID No. 3 is a nucleotide sequence encoding an $α_3$ subunit of human neuronal nicotinic acetylcholine receptor, and the deduced amino acid sequence thereof.

Sequence ID No. 4 is the amino acid sequence of the $α_3$ subunit of human neuronal nicotinic acetylcholine receptor set forth in Sequence ID No. 3.

Sequence ID No. 5 is a nucleotide sequence encoding an $α_4$ subunit of a human neuronal nicotinic acetylcholine receptor, and the deduced amino acid sequence thereof Sequence ID No. 6 is the amino acid sequence of the $α_4$ subunit of a human neuronal nicotinic acetylcholine receptor set forth in Sequence ID No. 5.

Sequence ID No. 7 is a nucleotide sequence encoding an $α_5$ subunit of human neuronal nicotinic acetylcholine receptor, and the deduced amino acid sequence thereof.

Sequence ID No. 8 is the amino acid sequence of the $α_5$ subunit of human neuronal nicotinic acetylcholine receptor set forth in Sequence ID No. 7.

Sequence ID No. 9 is a nucleotide sequence encoding an $α_6$ subunit of human neuronal nicotinic acetylcholine receptor, and the deduced amino acid sequence thereof.

Sequence ID No. 10 is the amino acid sequence of the $α_6$ subunit of human neuronal nicotinic acetylcholine receptor set forth in Sequence ID No. 9.

Sequence ID No. 11 is a nucleotide sequence encoding an $α_7$ subunit of human neuronal nicotinic acetylcholine receptor, and the deduced amino acid sequence thereof.

Sequence ID No. 12 is the amino acid sequence of the $α_7$ subunit of human neuronal nicotinic acetylcholine receptor set forth in Sequence ID No. 11.

Sequence ID No. 13 is a nucleotide sequence encoding a $β_2$ subunit of human neuronal nicotinic acetylcholine receptor, and the deduced amino acid sequence thereof.

Sequence ID No. 14 is the amino acid sequence of the $β_2$ subunit of human neuronal nicotinic acetylcholine receptor set forth in Sequence ID No. 13.

Sequence ID No. 15 is a nucleotide sequence encoding $β_3$ subunit of human neuronal nicotinic acetylcholine receptor, and the deduced amino acid sequence thereof Sequence ID No. 16 is the amino acid sequence of the $β_3$ subunit of human neuronal nicotinic acetylcholine receptor, set forth in Sequence ID No. 15.

Sequence ID No. 17 is a nucleotide sequence encoding a $β_4$ subunit of human neuronal nicotinic acetylcholine receptor, and the deduced amino acid sequence thereof.

Sequence ID No. 18 is the amino acid sequence of the $β_4$ subunit of human neuronal nicotinic acetylcholine receptor set forth in Sequence ID No. 17.

We claim:

1. A stably transfected rodent cell line which has been engineered to express a heterologous protein, said cell line comprising a host cell transformed or transfected with a heterologous nucleic acid molecule comprising a sequence of nucleotides or ribonucleotides that inducibly express an $\alpha_7$ subunit of a human neuronal nicotinic acetylcholine receptor, wherein said $\alpha_7$ subunit comprises a sequence of nucleotides selected from the group consisting of:

(a) a sequence of nucleotides as set forth in SEQ ID No: 11 which encode a human $\alpha_7$ subunit, (b) a sequence of nucleotides that encode a polypeptide as set forth in SEQ ID No: 12;

(c) a sequence of nucleotides degenerate with the human $\alpha_7$ subunit polypeptide encoding sequence of (a) or (b).

2. The cell line according to claim 1, wherein the heterologous protein is a functional human neuronal nicotinic acetylcholine receptor.

3. The cell line according to claim 1, further comprising a marker gene, wherein expression of the marker gene indicates expression of the heterologous protein.

4. The cell line according to claim 1, wherein the heterologous nucleic acid molecule is confined within an expression vector.

5. The stable transfected cell line according to claim 1, wherein the polypeptide of SEQ ID NO: 12 is the only heterologous acetylcholine receptor subunit expressed by the cell.

6. A recombinant host cell comprising a heterologous nicotinic acetylcholine receptor that comprises a subunit encoded by a heterologous nucleic acid molecule comprising a sequence of nucleotides or ribonucleotides as set forth in SEQ ID No: 11.

7. A recombinant host cell comprising a heterologous nicotinic acetylcholine receptor that comprises a subunit encoded by a heterologous nucleic acid molecule wherein said nucleic acid molecule encodes a polypeptide comprising the sequence of amino acids as set forth in SEQ ID No: 12.

8. The host cell according to claim 7, wherein the polypeptide of SEQ ID NO: 12 is the only heterologous acetylcholine receptor subunit expressed by the cell.

* * * * *